United States Patent
Jin et al.

(10) Patent No.: US 10,570,467 B1
(45) Date of Patent: Feb. 25, 2020

(54) RECOMBINANT MICROORGANISMS FOR CONVERSION OF OLIGOSACCHARIDES INTO FUNCTIONAL SWEETENERS

(71) Applicants: The Board of Trustees of the University of Illinois, Urbana, IL (US); ZIMITECH, Berkeley, CA (US)

(72) Inventors: Yong-Su Jin, Champaign, IL (US); Jingjing Liu, Urbana, IL (US); Kulika Chomvong, Berkeley, CA (US); Jamie H. D. Cate, Berkeley, CA (US); Guochang Zhang, Urbana, IL (US)

(73) Assignees: THE BOARD OF TRUSTEES OF THE UNIVERSITY OF ILLINOIS, Urbana, IL (US); ZIMITECH, Berkeley, CA (US)

( * ) Notice: Subject to any disclaimer, the term of this patent is extended or adjusted under 35 U.S.C. 154(b) by 0 days.

(21) Appl. No.: 15/716,621

(22) Filed: Sep. 27, 2017

Related U.S. Application Data

(60) Provisional application No. 62/400,424, filed on Sep. 27, 2016.

(51) Int. Cl.

| | | |
|---|---|---|
| *C12N 1/20* | (2006.01) | |
| *C12R 1/865* | (2006.01) | |
| *C12N 1/16* | (2006.01) | |
| *C12N 15/52* | (2006.01) | |
| *C12P 19/02* | (2006.01) | |
| *C12N 9/40* | (2006.01) | |

(52) U.S. Cl.
CPC .............. *C12R 1/865* (2013.01); *C12N 1/16* (2013.01); *C12N 9/2465* (2013.01); *C12N 15/52* (2013.01); *C12P 19/02* (2013.01); *C12N 2330/50* (2013.01); *C12N 2510/02* (2013.01); *C12N 2511/00* (2013.01)

(58) Field of Classification Search
CPC ............. C12N 9/90; C12P 19/14; C12P 19/34
USPC ..................... 435/183, 193, 252.3
See application file for complete search history.

(56) References Cited

U.S. PATENT DOCUMENTS 6,057,135 A  5/2000 Ibrahim
8,227,595 B2 7/2012 Vagnoli

FOREIGN PATENT DOCUMENTS

WO   2000068397        11/1999
WO   2009157736 A2      6/2009
WO   2013155481 A1     10/2013

OTHER PUBLICATIONS

Liu et al., "Overcoming the thermodynamic equilibrium of an isomerization reaction through oxidoreductive reactions for biotransformation", Nature Communications, p. 1-8 (2019).
Wanarska et al., "A method for the production of D-tagatose using a recombinant Pichia pastoris strain secreting beta-D-galactosidase from Arthrobacter chlorophenolicus and a recombinant L-arabinose isomerase from *Arthrobacter* sp. 22c.", Microb Cell Fact 11:113 (2012).
Cheng et al., "Thermostable L-arabinose isomerase from Bacillus stearothermophilus IAM 11001 for D-tagatose production: gene cloning, purification and characterisation", J Sci Food Agric 90(8):1327-1333 (2010).
Kim B-C et al., "Cloning, expression and characterization of L-arabinose isomerase from Thermotoga neapolitana: bioconversion of D-galactose to D-tagatose using the enzyme", FEMS Microbiology Letters 212(1):121-126 (2002).
Lim et al., "High production of D-tagatose by the addition of boric acid", Biotechnol Prog 23(4):824-828 (2007).
Seiboth et al., "The D-xylose reductase of Hypocrea jecorina is the major aldose reductase in pentose and D-galactose catabolism and necessary for beta-galactosidase and cellulase induction by lactose", Mol Microbiol 66(4):890-900 (2007).
Jagtap et al., "Cloning and characterization of a galactitol 2-dehydrogenase from Rhizobium legumenosarum and its application in D-tagatose production", Enzyme Microb Technol 58-59:44-51 (2014).

*Primary Examiner* — Tekchand Saidha
(74) *Attorney, Agent, or Firm* — DLA Piper LLP (US)

(57) ABSTRACT

The present disclosure provides genetically engineered microorganisms for tagatose production comprising one or more heterologous polynucleotides encoding polypeptides selected from cellodextrin transporter (Cdt-1), intracellular β-glucosidase (Gh1-1), xylose reductase (XR), galactitol 2-dehydrogenase (Gdh) and an AraA polypeptide, wherein any biological activity of endogenous Gal1 is attenuated or eliminated. Also provided are genetically engineered microorganism for psicose production comprising one or more heterologous polynucleotides encoding polypeptides selected from alpha-glucoside permease (Agt1) and psicose epimerase (Dpe), wherein any biological activity of endogenous sucrose invertase (Suc2), hexose kinase 1 (Hxk1), hexose kinase 2 (Hxk2), or combinations thereof are attenuated or eliminated. Methods of converting lactose to tagatose and sucrose to psicose is also provided.

16 Claims, 8 Drawing Sheets
(4 of 8 Drawing Sheet(s) Filed in Color)
Specification includes a Sequence Listing.

US 10,570,467 B1

RECOMBINANT MICROORGANISMS FOR CONVERSION OF OLIGOSACCHARIDES INTO FUNCTIONAL SWEETENERS

PRIORITY

This application claims the benefit of U.S. Ser. No. 62/400,424, filed on Sep. 27, 2016, which is incorporated by reference herein in its entirety.

SEQUENCE LISTING

This document incorporates by reference herein an electronic sequence listing text file, which is filed in electronic format via EFS-Web. The text file is named "17-1294-US_SequenceListing_ST25.txt" is 71.2 KB, and was created on Sep. 26, 2017.

BACKGROUND

Thermodynamic equilibrium is a fundamental and inherent feature of reactions catalyzed by isomerase enzymes. During industrial production of chemicals of interest involving isomerization reactions, this feature always leads to not only incomplete conversion of upstream substrates, but also difficulties and extra cost on downstream product separation and purification. One typical example is the rare sugar industry which by far has been using isomerization reactions (1-4) and thus cannot outcompete other sweetener industries due to the significantly higher production cost, even though rare sugars exhibit numerous beneficial traits. Specifically, tagatose, a naturally occurring functional sweetener with 92% of the sweetness as sucrose in 10% (w/w) solution, but with only 1.5 kcal/g compared with table sugar's 4 kcal/g (1, 2), has been widely produced through isomerization reaction from galactose. Its conversion rate is always low due to the thermodynamic equilibrium problems (3, 4). For example, the thermodynamic equilibrium between galactose and tagatose is 7:3 based on L-arabinose isomerase (L-AI) reaction (5, 6). Maximum conversion rate of 35% for L-AI from *Lactobacillus reuteri* was achieved by increasing the temperature to 60° C. (7). The bioconversion yield of galactose to tagatose by the purified thermostable L-AI from *Bacillus stearothermophilus* reached 36% after 12 h at 65° C. (8). The conversion rate of 68% was achieved using L-AI from *Thermotoga* neapolitana at 80° C. (9). The addition of boric acid increased the conversion rate to 74% using L-AI mutant enzyme purified from *Geobacillus thermodenitrificans* at 60° C. (10).

As such, although galactose-tagatose conversion rate can be improved when high temperature is used, it is not cost-effective and still cannot achieve complete substrate conversion. In addition, to obtain galactose, the direct substrate for tagatose production, an enzymatic hydrolysis of lactose and a follow-up separation of glucose and galactose are required, leading to substantial extra cost. Moreover, the industrial scale-up cost increases sharply when purified enzymes instead of a self-sustaining bioconversion system are used. Therefore, the current tagatose has industry encountered a bottleneck on reducing production cost. Cost effective methods of producing rare sugars via fermentation are needed in the art.

SUMMARY

An embodiment provides a recombinant microorganism comprising heterologous polynucleotides encoding a cellodextrin transporter (Cdt-1) polypeptide; a β-galactosidase (Gh1-1) polypeptide; a xylose reductase (XR) polypeptide; and a galactitol 2-dehydrogenase (Gdh) polypeptide or a L-arabinose isomerase (AraA) polypeptide, wherein any biological activity of an endogenous Gal1 polypeptide is attenuated or eliminated.

Another embodiment provide a recombinant microorganism comprising an operative metabolic pathway for producing tagatose, wherein the recombinant microorganism expresses: a) a heterologous cellodextrin transporter (Cdt-1) polypeptide for transport of lactose into the recombinant microorganism; b) a heterologous β-galactosidase (Gh1-1) polypeptide for converting lactose to glucose and galactose; c) a heterologous xylose reductase (XR) polypeptide for conversion of galactose into galactitol; d) a heterologous galactitiol-2-dehydrogenase (Gdh) polypeptide to convert galactitol to tagatose, or a heterologous L-arabinose isomerase (AraA) polypeptide to convert L-arabinose to L-ribulose, or both a heterologous Gdh polypeptide and an heterologous AraA polypeptide; and wherein any biological activity of an endogenous Gal1 polypeptide is attenuated or eliminated. The heterologous Cdt-1 polypeptide can have at least 90% sequence identity to SEQ ID NO:5 and can have cellodextrin transporter activity, the heterologous Gh1-1 polypeptide can have at least 90% sequence identity to SEQ ID NO:6 and can have β-galactosidase activity, the heterologous xylose reductase polypeptide can have at least 90% sequence identity to SEQ ID NO:7 and can have xylose reductase activity, and the heterologous Gdh polypeptide can have at least 90% sequence identity to SEQ ID NO:8 and can have galactitiol-2-dehydrogenase activity. Any biological activity of an endogenous hexose kinase 1 (Hxk1), an endogenous hexose kinase 2 (Hxk2), or combinations thereof can be attenuated or eliminated. The Cdt-1 polypeptide can be encoded by a polynucleotide as set forth in SEQ ID NO: 1, the Gh1-1 polypeptide can be encoded by a polynucleotide as set forth in SEQ ID NO:2, the XR polypeptide can be encoded by a polynucleotide as set forth in SEQ ID NO:3, and the Gdh polypeptide can be encoded by a polynucleotide as set forth in SEQ ID NO:4, SEQ ID NO:30, or SEQ ID NO:31. A polynucleotide encoding the Cdt-1 polypeptide can have at least 90% sequence identity to SEQ ID NO:1, wherein a polynucleotide encoding the Gh1-1 polypeptide can have at least 90% sequence identity to SEQ ID NO:2, wherein a polynucleotide encoding the XR polypeptide can have at least 90% sequence identity to SEQ ID NO:3, and a polynucleotide encoding the Gdh polypeptide can have at least 90% sequence identity to SEQ ID NO:4, SEQ ID NO:30, or SEQ ID NO:31. The Cdt-1 polypeptide can have the amino acid sequence set forth in SEQ ID NO:5, the Gh1-1 polypeptide can have the amino acid sequence set forth in SEQ ID NO:6, the XR polypeptide can have the amino acid sequence set forth in SEQ ID NO:7, and the Gdh polypeptide can have the amino acid sequence set forth in SEQ ID NO:8.

The recombinant microorganism can be selected from Saccharomyceraceae sp., *Saccharomyces cerevisiae*, *Saccharomyces pastorianus*, *Saccharomyces beticus*, *Saccharomyces fermentati*, *Saccharomyces paradoxus*, *Saccharomyces uvarum Saccharomyces bay anus*; *Schizosaccharomyces* sp., *Schizosaccharomyces pombe*, *Schizosaccharomyces japonicus*, *Schizosaccharomyces octosporus*, *Schizosaccharomyces cryophilus*, *Torulaspora* sp., *Torulaspora delbrueckii*, *Kluyveromyces* sp., *Kluyveromyces marxianus*, *Pichia* sp., *Pichia stipitis*, *Pichia pastoris*, *Pichia angusta*, *Zygosaccharomyces* sp., *Zygosaccharomyces bailii*, *Brettanomyces* sp., *Brettanomyces inter medius*, *Brettanomyces* bruxellensis, Brettanomyces anomalus, Brettanomyces custersianus, Brettanomyces naardenensis, Brettanomyces nanus, Dekkera bruxellensis, Dekkera anomala; Metschmkowia sp., Issatchenkia sp., Issatchenkia orientalis, Kloeckera sp. Kloeckera apiculate, Aureobasidium sp., Aureobasidium pullulans, and Corynebacterium glutamicum.

Yet another embodiment provides a method for producing tagatose comprising culturing the recombinant microorganisms with a substrate under suitable fermentation conditions to produce the tagatose. The substrate can comprise lactose.

Still another embodiment provides a method of treating acid whey comprising contacting the recombinant microorganisms with the acid whey under suitable fermentation conditions such that the acid whey is treated.

Another embodiment provides a recombinant microorganism comprising an operative metabolic pathway for producing psicose, wherein the recombinant microorganism expresses: a) a heterologous alpha-glucoside permease (Agt1) polypeptide for sucrose transport; b) a heterologous psicose epimerase (Dpe) polypeptide for production of psicose; and wherein any biological activity of an endogenous sucrose invertase (Suc2), endogenous hexose kinase 1 (Hxk1), endogenous hexose kinase 2 (Hxk2), or combinations thereof are attenuated or eliminated. The heterologous Agt1 polypeptide can have at least 90% sequence identity to the amino acid sequence set forth in SEQ ID NO:11 and can have alpha-glucoside permease activity, and the heterologous Dpe polypeptide can have at least 90% sequence identity to the amino acid sequence set forth in SEQ ID NO:12 and have psicose epimerase activity.

Still another embodiment provides a recombinant microorganism comprising one or more heterologous polynucleotides encoding an alpha-glucoside permease (Agt1) polypeptide, and a psicose epimerase (Dpe), and wherein any biological activity of an endogenous Gal1 polypeptide, an endogenous sucrose invertase (Suc2) polypeptide, an endogenous hexose kinase 1 (Hxk1) polypeptide, an hexose kinase 2 (Hxk2) polypeptide, or combinations thereof is attenuated or eliminated. The recombinant microorganism can further comprise a heterologous polynucleotide sequence encoding a GroES polypeptide, a GroEL chaperonin polypeptide, or combinations thereof. The Agt1 polypeptide can be encoded by a polynucleotide set forth in SEQ ID NO:9, and the Dpe polypeptide can be encoded by a polynucleotide set forth in SEQ ID NO:10. The GroEL polypeptide can be encoded by a polynucleotide set forth in SEQ ID NO:16 and the GroES polypeptide can be encoded by a polynucleotide set forth in SEQ ID NO:14. A polynucleotide encoding the Agt1 polypeptide can have at least 90% sequence identity to SEQ ID NO:9, and a polynucleotide encoding the Dpe polypeptide can have at least 90% sequence identity to SEQ ID NO:10. A polynucleotide encoding the GroEL polypeptide can have at least 90% sequence identity to SEQ ID NO:16 and a polynucleotide encoding the GroES polypeptide can have at least 90% sequence identity to SEQ ID NO:14. The Agt1 polypeptide can have the amino acid sequence set forth in SEQ ID NO:11, and the Dpe polypeptide can have the amino acid sequence set forth in SEQ ID NO:12. The Agt1 polypeptide can have at least 90% sequence identity to the amino acid sequence set forth in SEQ ID NO:11, and the Dpe polypeptide can have at least 90% sequence identity to the amino acid sequence set forth in SEQ ID NO:12. The microorganism can be selected from Saccharomyceraceae sp., Saccharomyces cerevisiae, Saccharomyces pastorianus, Saccharomyces beticus, Saccharomyces fermentati, Saccharomyces paradoxus, Saccharomyces uvarum Saccharomyces bay anus; Schizosaccharomyces sp., Schizosaccharomyces pombe, Schizosaccharomyces japonicus, Schizosaccharomyces octosporus, Schizosaccharomyces cryophilus, Torulaspora sp., Torulaspora delbrueckii, Kluyveromyces sp., Kluyveromyces marxianus, Pichia sp., Pichia stipitis, Pichia pastoris, Pichia angusta, Zygosaccharomyces sp., Zygosaccharomyces bailii, Brettanomyces sp., Brettanomyces inter medius, Brettanomyces bruxellensis, Brettanomyces anomalus, Brettanomyces custersianus, Brettanomyces naardenensis, Brettanomyces nanus, Dekkera bruxellensis, Dekkera anomala; Metschmkowia sp., Issatchenkia sp., Issatchenkia orientalis, Kloeckera sp. Kloeckera apiculate, Aureobasidium sp., Aureobasidium pullulans, and Corynebacterium glutamicum.

Another embodiment provides a method for producing psicose comprising culturing the recombinant microorganism with a substrate under suitable fermentation conditions to produce the psicose.

Still another embodiment provides a method of converting sucrose to psicose, the method comprising contacting the recombinant microorganism with a substrate comprising sucrose under suitable fermentation conditions such that psicose is produced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein.

Figure 1:
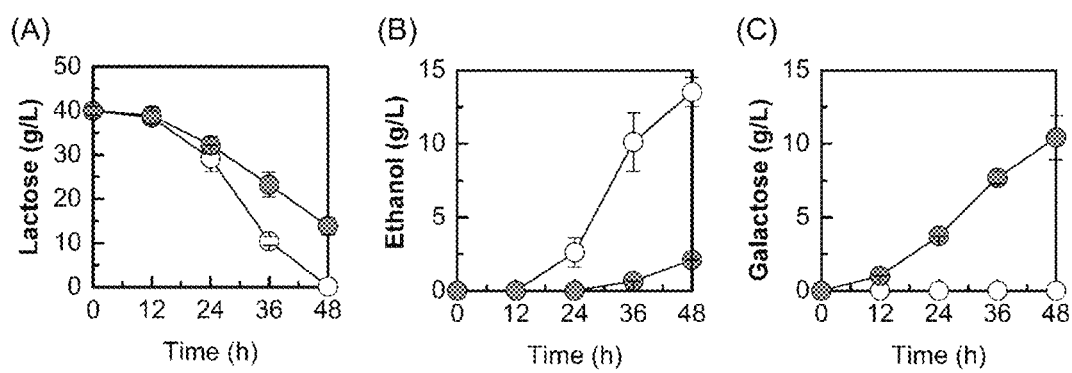
FIG. 1 panels A-C. Galactose is accumulated in lactose consuming strain EJ2 with GAL1 deletion. A: The fermentation profile of yeast strain expressing CDT-1 and gh1-1 on YP with 40 g/L of lactose under micro-aerobic condition; B: The fermentation profile of yeast strain expressing CDT-1 and gh1-1 with GAL1 deletion on YP with 40 g/L of lactose under micro-aerobic condition. Data are presented as mean value and standard deviations of three independent biological replicates.

While the present embodiments are susceptible to various modifications and alternative forms, exemplary embodiments thereof are shown by way of example in the drawings and are herein described in detail. It should be understood, however, that the description of exemplary embodiments is not intended to limit the compositions and methods to the particular forms disclosed, but on the contrary, the intention is to cover all modifications, equivalents and alternatives falling within the spirit and scope of the methods and compositions as defined by the embodiments above and the claims below. Reference should therefore be made to the embodiments above and claims below for interpreting the scope of the compositions and methods.

DETAILED DESCRIPTION

This compositions and method are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

Likewise, many modifications and other embodiments of the genetically modified microorganisms and methods described herein will come to mind to one of skill in the art having the benefit of the teachings presented in the foregoing descriptions and the associated drawings. Therefore, it is to be understood that the methods and compositions are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art.

Overview

The present disclosure provides a novel strategy for sustainable and cost-effective tagatose and psicose production. Specifically, for tagatose production, instead of an isomerization reaction using L-arabinose isomerase, a two-step oxidoreductive pathway comprising an aldose reductase and a galactitol-2-dehydrogenase were employed in the engineered yeast S. cerevisiae strain. To enable continuous tagatose production through self-sustained bioconversion, a delicate carbon partition strategy was developed using lactose instead of galactose as the substrate. Upon introduction of the lactose pathway containing lactose transporter CDT-1 and β-galactosidase GH1-1 into a yeast strain lacking galactose kinase (Gal1) expression. The carbon partition strategy allowed the hydrolyzed glucose moiety to serve as energy source for cell growth and maintenance, and the galactose moiety to be converted to tagatose simultaneously. Efficient and rapid tagatose production was achieved through one-step lactose fermentation by an engineered yeast strain. Around 80% of the hydrolyzed galactose was easily converted to tagatose during the fermentation process due to the breakup of the thermodynamic equilibrium by the oxidoreductive pathway.

The bioconversion strategy can convert an abundant sugar (lactose) in dairy by—product into a functional sweetener (D-tagatose) by engineered yeast. Existing strategies include the use of multiple enzyme reactions and separation steps for the conversion of lactose into tagatose as follows. First, lactose is hydrolyzed to produce glucose and galactose using beta-galactosidase. Second, galactose is separated from a mixture of glucose and galactose. Third, galactose is converted into tagatose by arabinose isomerase. Fourth, tagatose is separated from a mixture of 70% galactose and 30% tagatose. In contrast, engineered microorganisms described herein can produce tagatose from lactose via one-step fermentation. The feasibility of overcoming the thermodynamic limit of isomerization reaction using oxidoreductases for value-added bioconversion is demonstrated.

Compositions and methods are described that will enable economic production of rare sugars, such as psicose and tagatose, which can be used as a sugar substitute. They have similar sweetness of sucrose but are not metabolized efficiently in the human body, i.e. are low-calorie or zero-calorie sugar substitutes. They also are suitable for establishing food matrix properties. Therefore, these rare sugars can be used as functional food ingredients. Tagatose, for example, can be used for drug purposes and as an "appetite suppressor," since unlike other low/zero calorie sweeteners, it is partially absorbed in the small intestine and metabolized like fructose, so it can help signaling sugar intake and could help prevent weight gain from using the zero calorie sweetener. There have been methods of producing psicose and tagatose from fructose and galactose, respectively, by enzymatic processes that have limitations on scalability and economic production. Large-scale production is feasible because the methods rely on engineered microorganisms instead of purified enzymes and it allows the use of inexpensive sucrose and lactose as substrates. Currently Greek yogurt companies struggle to dispose of acid whey by-product, generated at three times the amount of Greek yogurt produced. The by-product, which contains significant amounts of lactose, cannot be discarded without treatment because it is hazardous to water quality. The present disclosure offers the Greek yogurt companies the ability to economically treat acid whey on-site. The present disclosure differs from its competing technologies because it captures and enhances the value of lactose in acid whey.

Figure 7:
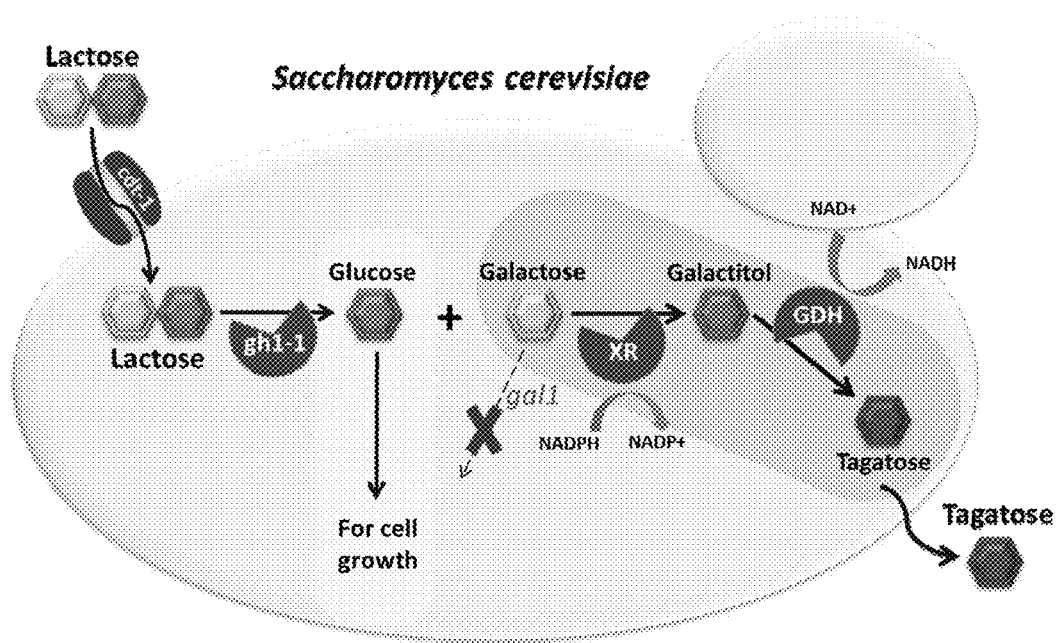
FIG. 7. The schematic diagram of the production of tagatose from lactose in S. cerevisiae.
Figure 8:
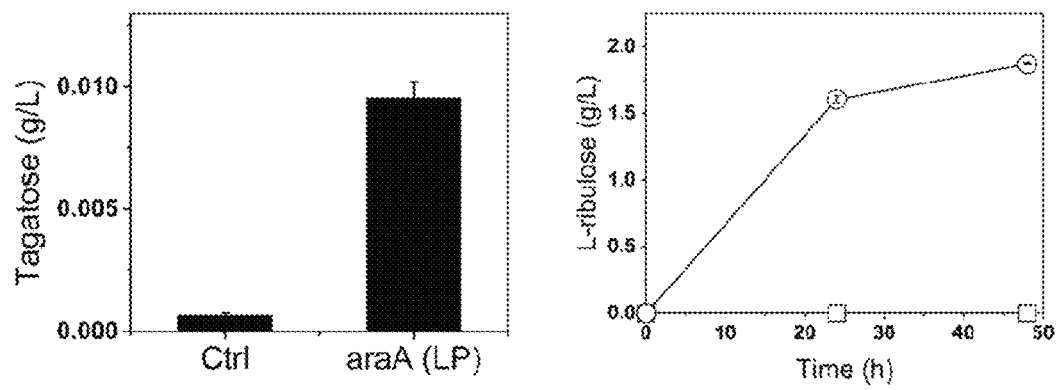
FIG. 8. The in vivo production of tagatose using isomerase reaction. Tagatose can be detected after 72 hours of fermentation using engineered yeast strain with L-arabinose isomerase. The right figure is in vitro reaction using L-arabinose as a substrate showing that L-arabinose isomerase is functionally working in yeast by introducing GroE (21).
Figure 9:
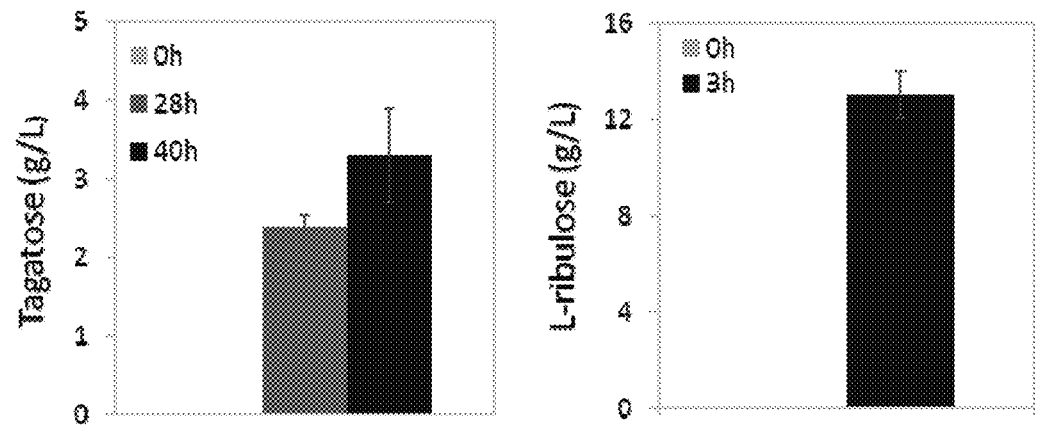
FIG. 9. The conversion of galactose to tagatose and L-arabinose to L-ribulose in vitro using L-arabinose isomerase from *Lactobacillus plantarum* using high cell density of engineered yeast cells under 60° C. The catalytic efficiency was 10-fold higher for the physiological substrate I-arabinose (15.5 mM$^{-1}$ min$^{-1}$) than D-galactose (1.6 mM$^{-1}$ min$^{-1}$) (6).
Figure 10:
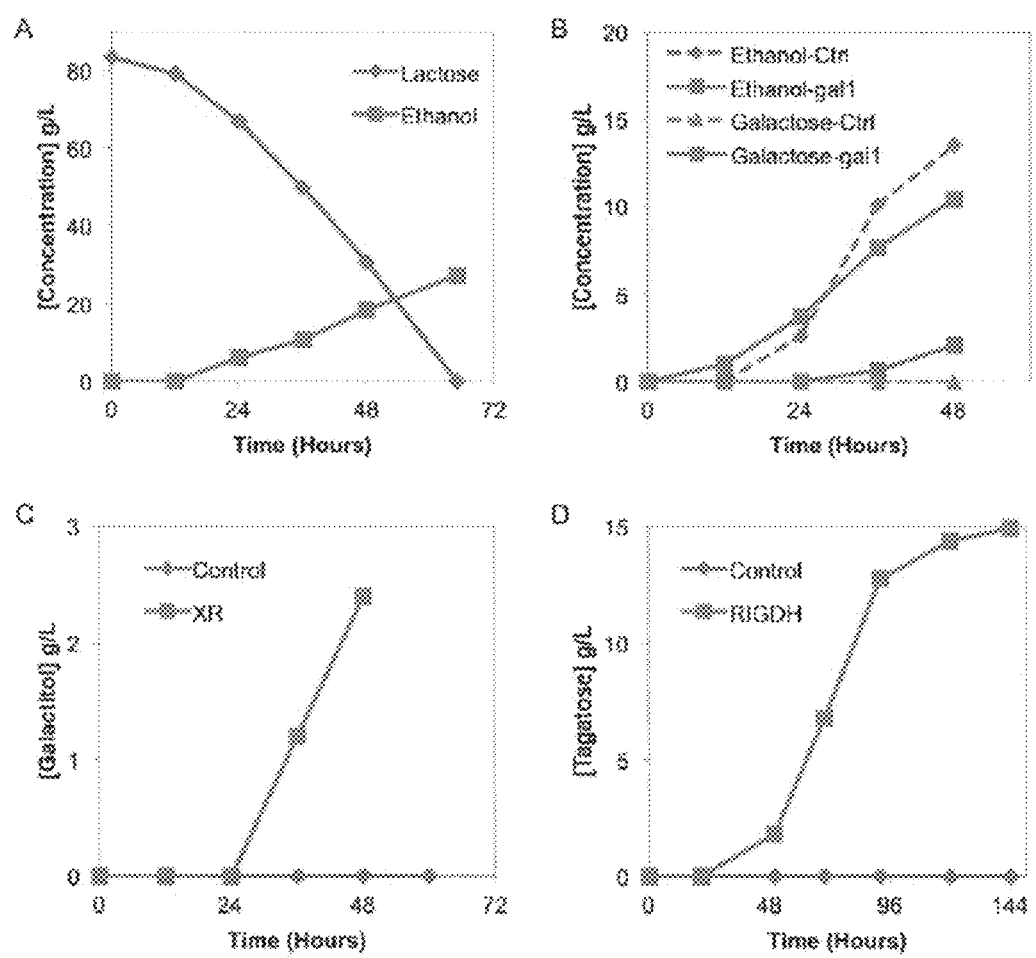
FIG. 10 panels A-D. Consumption and production profiles of the engineered yeasts. (A) Extracellular concentration of lactose and ethanol of the yeast strain expressing Cdt-1 and Gh1-1. (B) Ethanol and galactose concentrations of yeast strains expressing cdt-1 and Gh1-1, with (denoted, gal) or without (denoted, Ctrl) GAL I deletion. (C) Galactitol concentrations of strains expressing CDT-1, GH1-1, GAL1Δ, with (denoted, XR) or without (denoted Control) xylose reductase expression. (D) Tagatose concentrations of strains expressing Cdt-1, Gh1-1, GAL1Δ, XR, with (denoted RIG DH) or without (denoted Control) polyol dehydrogenase expression.

The core technology for tagatose production includes genetically engineered microorganisms, for example, a *S. cerevisiae* strain capable of producing tagatose from lactose. Lactose is imported into the cells by Cdt-1 before being hydrolyzed intracellularly by Gh1-1, yielding glucose and galactose as products. Glucose is used for cell maintenance purposes while galactose is reduced to galactitol by aldose reductase and hydrogenated by polyol dehydrogenase or L-arabinose isomerase, producing tagatose as a final product (FIG. 7). First, a cellodextrin utilization pathway derived from, for example, *N. crassa* is relevant to the use of lactose in acid whey. Lactose, a dimer of galactose linked to glucose, is structurally similar to cellobiose, a dimer of glucose. Both have glucose monomers at the reducing ends and their monomers are linked by 13-1,4 linkage. *S. cerevisiae* expressing Cdt-1 and Gh1-1 was shown to utilize lactose, a substrate which cannot be metabolized by wild-type *S. cerevisiae* (FIG. 1). Second, the ability of the engineered yeast strain to partition the imported lactose was shown by disrupting the galactose utilization pathway. GAL1 coding for galactokinase, responsible for phosphorylation of galactose to galactose 1-phosphate, was deleted. Ethanol production and galactose accumulation were concurrently observed in this strain, suggesting that the strain lacking GAL1 was still capable of cell maintenance even though galactose could not be metabolized (FIG. 1). Last, a synthetic pathway comprised of xylose reductase (XR) and polyol dehydrogenase (Gdh) was introduced to convert galactose to galactitol and tagatose, respectively. Galactitol accumulation was observed in the engineered strain (EJ2g X), suggesting that XR is capable of reducing galactose to galactitol (FIG. 2C). The previous strain was further engineered by introducing galactitol 2-dehydrogenase, resulting in a tagatose producing yeast (FIG. 3D). The best engineered strain with minimal optimization already produces 40% of the theoretical yield of tagatose from lactose. Despite this oxidoreductase pathway of XR-Gdh, direct conversion of galactose to tagatose through arabinose isomerase is an alternative pathway. In the tagatose production industry, isomerase reaction has been adopted. L-arabinose isomerase (araA). In an embodiment, a heterologous polypeptide can be added to a recombinant microorganism described herein such that a biologically active araA polypeptide is expressed by the recombinant microorganism.

The present disclosure provides genetically engineered microorganisms for tagatose production expressing heterologous polynucleotides selected from CDT-1, GH1-1, XR, GDH and ARAA or expression of a mutant form having increased Cdt-1, Gh1-1, XR, Gdh, and AraA activity, and lacking or having reduced expression of galactokinase (Gal1). The present disclosure also provides genetically engineered microorganisms for production of psicose expressing heterologous polynucleotides selected from AGT1 and DPE, or expression of a mutant form having increased Agt1 and Dpe activity, and lacking or having reduced expression of Suc2, Hxk1, Hxk2 polypeptides, or expression of a mutant or deleted form lacking or having reduced activity of these polypeptides. The reduced or deleted expression, or expression of mutated, inactive, or reduced activity polypeptides can be accomplished by deletion of a polynucleotide encoding Suc2, Hxk1, Hxk2, and Gal1, by replacement of the wild-type polynucleotides with mutated forms, by deletion of a portion of the polynucleotide to cause expression of an inactive form of the polypeptides, or manipulation of the regulatory elements (e.g. promoter) to prevent or reduce expression of wild-type Suc2, Hxk1, Hxk2, and Gal1. The promoter could also be replaced with a weaker promoter or an inducible promoter that leads to reduced expression of the polypeptides. Any method of genetic manipulation that leads to a lack of, or reduced expression and/or activity of Suc2, Hxk1, Hxk2 and Gal1 can be used in the present compositions, including expression of inhibitor RNAs (e.g. shRNA, siRNA, and the like). Increased activity or heterologous expression of Cdt-1, Gh1-1, XR, Gdh and AraA can be accomplished by introducing the heterologous polynucleotides to the microorganism by methods well known in the art, by manipulating the promoters, or by introducing a more active promoter to endogenous CDT-1, GH1-1, XR, GDH and ARAA genes to increase expression and/or activity.

Recombinant Microorganisms

A recombinant, transgenic, or genetically engineered microorganism is a microorganism, e.g., bacteria, fungus, or yeast that has been genetically modified from its native state. Thus, a "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast or yeast cell, or on a plasmid in the yeast or yeast cell. Recombinant cells disclosed herein can comprise exogenous polynucleotides on plasmids. Alternatively, recombinant cells can comprise exogenous polynucleotides stably incorporated into their chromosome.

A heterologous or exogenous polypeptide or polynucleotide refers to any polynucleotide or polypeptide that does not naturally occur or that is not present in the starting target microorganism. For example, a polynucleotide from bacteria that is transformed into a yeast cell that does naturally or otherwise comprise the bacterial polynucleotide is a heterologous or exogenous polynucleotide. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target microorganism and is from a different genus or species than the starting target microorganism.

A homologous or endogenous polypeptide or polynucleotide refers to any polynucleotide or polypeptide that naturally occurs or that is otherwise present in a starting target microorganism. For example, a polynucleotide that is naturally present in a yeast cell is a homologous or endogenous polynucleotide. In an embodiment, a homologous or endogenous polypeptide or polynucleotide is naturally present in a starting target microorganism.

A recombinant microorganism can comprise one or more polynucleotides not present in a corresponding wild-type cell, wherein the polynucleotides have been introduced into that microorganism using recombinant DNA techniques, or which polynucleotides are not present in a wild-type microorganism and is the result of one or more mutations.

A genetically modified or recombinant microorganism can be, for example, Saccharomyceraceae, such as *Saccharomyces cerevisiae, Saccharomyces cerevisiae* strain S8, *Saccharomyces pastorianus, Saccharomyces beticus, Saccharomyces fermentati, Saccharomyces paradoxus, Saccharomyces uvarum* and *Saccharomyces bayanus; Schizosaccharomyces* such as *Schizosaccharomyces pombe, Schizosaccharomyces japonicus, Schizosaccharomyces octosporus* and *Schizosaccharomyces cryophilus; Torulaspora* such as *Torulaspora delbrueckii; Kluyveromyces* such as *Kluyveromyces marxianus; Pichia* such as *Pichia stipitis, Pichia pastoris* or *Pichia angusta, Zygosaccharomyces* such as *Zygosaccharomyces bailii; Brettanomyces* such as *Brettanomyces inter medius, Brettanomyces bruxellensis, Brettanomyces anomalus, Brettanomyces custersianus, Brettanomyces naardenensis, Brettanomyces nanus, Dekkera bruxellensis* and *Dekkera anomala; Metschmkowia, Issatchenkia,* such as *Issatchenkia orientalis, Kloeckera* such as *Kloeckera apiculata; Aureobasidium* such as *Aureobasidium pullulans*. Yeast and bacteria, such as *Corynebacterium glutamicum* can be used in the methods described herein.

In an embodiment a genetically engineered or recombinant microorganism comprises one or more heterologous or exogenous polynucleotides, optionally operably linked to one or more heterologous, exogenous, or endogenous regulatory elements such that one or more heterologous or exogenous biologically active polypeptides are expressed by the microorganism. A genetically engineered microorganism can comprise one or more heterologous polynucleotides encoding a cellodextrin transporter (Cdt-1) polypeptide, a β-galactosidase (Gh1-1) polypeptide, a xylose reductase (XR) polypeptide, a galactitol 2-dehydrogenase (Gdh) polypeptide, an L-arabinose-isomerase polypeptide (AraA), an alpha-glucoside permease (Agt1) polypeptide, a psicose epimerase (Dpe) polypeptide, a GroEL polypeptide, a GroES polypeptide or combinations thereof.

Cdt-1 polypeptides include, for example *Neurospora crassa* CDT-1 (UniProt: Q7SCU1 (SEQ ID NO:5) or the polypeptide encoded by GenBank: XM_958708.2 (SEQ ID NO:1); additional Cdt-1 transporters can be found in, for example, U.S. Pat. Nos. 8,431,360; 8,765,410, and 9,012,177, which are incorporated herein by reference).

Gh1-1 polypeptides include, for example, *Neurospora crassa* Gh1-1 (UniProt U9W8B8; SEQ ID NO:6) or the polypeptide encoded by GenBank XM_011395457.1 (SEQ ID NO:2)). XR polypeptides include, for example, Scheffersomyces stipites XR (UniProt: P31867; SEQ ID NO:7) or the polypeptide encoded by GenBank XM_0013851441.1 (SEQ ID NO:03). Gdh polypeptides include, for example, the polypeptide of SEQ ID NO:8 or the polypeptide encoded by SEQ ID NO:4, SEQ ID NO:30; or SEQ ID NO:31. AraA polypeptides include, for example, GenBank UniParc P08202-1 (SEQ ID NO:32)(from *E. coli*); EMBL-EBI ACM22585.1 (from *Thermotoga neapolitana*); EMBL-EBI AEH51205.1 (from *Psedothermotoga thermarum*); UniParc P94523-1 (from *B. subtilis*); UniProtKB Q48433 (from *Klebsiella pneumoniae*). Other AraA polypeptides are known and are produced by, for example, *M. smegmatis, B. licheniformis, L. plantarum, Arthrobacter aurescens, Clavibacter michiganensis, Gramella forsetii. B. thetaiotamicron,* and *Thermotoga neapolitana*. Polynucleotides encoding these AraA proteins can be used herein. Variants of AraA are taught in US Publ. No. 20170137856 and can be used herein. Agt1 polypeptides include, for example, *S. cerevisiae* Agt1 (UniProt: P53048; SEQ ID NO:11) or the polypeptide encoded by NM_001181418.3 (SEQ ID NO:9). Dpe polypeptides include, for example, *Agrobacterium tumefaciens* Dpe (GenBank WP_010974125.1; SEQ ID NO:12) or the polypeptide encoded by GenBank KX098480.1 (SEQ ID NO:10)). GroEL polypeptides include, for example, *E. coli* GroEL (UniProt: P0A6F5; SEQ ID NO:15) or the polypeptide encoded by CP022466.1 (SEQ ID NO:16)). GroES polypeptides include, for example, *E. coli* GroES (UniProt: P0A6F9 (SEQ ID NO:13) or the polypeptide encoded by CP023142.1 (SEQ ID NO:14)).

The term "overexpression" or "overexpressed" as used herein refers to a level of enzyme or polypeptide expression that is greater than what is measured in a wild-type cell of the same species as the host cell that has not been genetically altered. The overexpression of the enzymes can be achieved by constructing inducible overexpression vectors encoding for the desired polypeptide. Strong promoters can be used to induce overexpression of a polypeptide as can the use of multiple copies of a polynucleotide in the recombinant microorganism. In an embodiment a Cdt-1, Gh1-1, XR, Gdh, AraA, Dpe, Agt1 polypeptide, or combinations thereof can be overexpressed.

In an embodiment a genetically engineered microorganism comprises one or more heterologous polynucleotides encoding a cellodextrin transporter (Cdt-1) polypeptide, a β-galactosidase (Gh1-1) polypeptide, a xylose reductase (XR) polypeptide, an L-arabinose isomerase (AraA), and a galactitol 2-dehydrogenase (Gdh) polypeptide. Optionally, any biological activity of endogenous Gal1 polypeptide can be attenuated or eliminated. Any biological activity of an endogenous polypeptide is attenuated or eliminated means that if a microorganism has biological activity of a polypeptide (e.g., Gal1 activity), then the biological activity is attenuated or eliminated.

In an embodiment, a recombinant microorganism comprises an operative metabolic pathway for producing tagatose. The recombinant microorganism can express: a) a heterologous cellodextrin transporter (Cdt-1) polypeptide for transport of lactose into the recombinant microorganism; b) a heterologous β-galactosidase (Gh1-1) polypeptide for converting lactose to glucose and galactose; c) a heterologous xylose reductase (XR) polypeptide for conversion of galactose into galactitol; and d) a heterologous galactitiol-2-dehydrogenase (Gdh) polypeptide to convert galacititol to tagatose and/or a heterologous L-arabinose isomerase polypeptide to convert L-arabinose to L-ribulose. Optionally, any biological activity of an endogenous Gal1 polypeptide can be attenuated or eliminated.

In an embodiment a heterologous Cdt-1 polypeptide has at least about 80, 85, 90, 95, 98, 99, or 100% sequence identity to SEQ ID NO:5 and has cellodextrin transporter activity, a heterologous Gh1-1 polypeptide has at least about 80, 85, 90, 95, 98, 99, or 100% sequence identity to SEQ ID NO:6 and has β-galactosidase activity, a heterologous xylose reductase polypeptide has at least about 80, 85, 90, 95, 98, 99, or 100% sequence identity to SEQ ID NO:7 and has xylose reductase activity, and a heterologous Gdh polypeptide has at least about 80, 85, 90, 95, 98, 99, or 100% sequence identity to SEQ ID NO:8 and has galactitiol-2- dehydrogenase activity. Optionally, a heterologous AraA polypeptide can additionally be included or can be used in place of a Gdh polypeptide. The AraA polypeptide can have at least about 80, 85, 90, 95, 98, 99, or 100% sequence identity to GenBank UniParc P08202-1; EMBL-EBI ACM22585.1; or EMBL-EBI AEH51205.1. The AraA polypeptide can convert L-arabinose to L-ribulose. Optionally, any biological activity of an endogenous hexose kinase 1 (Hxk1), an endogenous hexose kinase 2 (Hxk2), or combinations thereof are attenuated or eliminated.

In an embodiment, a Cdt-1 polypeptide comprises at least 90% amino acid sequence identity to SEQ ID NO:5, a Gh1-1 polypeptide comprises at least 90% amino acid sequence identity to SEQ ID NO:6, a XR polypeptide comprises at least 90% amino acid sequence identity to SEQ ID NO:7, and a Gdh polypeptide comprises at least 90% amino acid sequence identity to SEQ ID NO:8. In an embodiment an AraA polypeptide has 90% sequence identity to GenBank UniParc P08202-1; EMBL-EBI ACM22585.1; or EMBL-EBI AEH51205.1.

In an embodiment the genetically engineered microorganism comprises a Cdt-1 polypeptide that can have the amino acid sequence set forth in SEQ ID NO:5, a Gh1-1 polypeptide that can have the amino acid sequence set forth in SEQ ID NO:6, a XR polypeptide that can have the amino acid sequence set forth in SEQ ID NO:7, and a Gdh polypeptide that can have the amino acid sequence set forth in SEQ ID NO:8.

A Cdt-1 polypeptide can be encoded by a polynucleotide having about at least 80, 85, 90, 95, 98, 99, or 100% sequence identity to SEQ ID NO:1, a Gh1-1 polypeptide can be encoded by a polynucleotide having at least about 80, 85, 90, 95, 98, 99, or 100% sequence identity to SEQ ID NO:2, a XR polypeptide can be encoded by a polynucleotide having about at least 80, 85, 90, 95, 98, 99, or 100% sequence identity to SEQ ID NO:3, and a Gdh polypeptide can be encoded by a polynucleotide having at least about 80, 85, 90, 95, 98, 99, or 100% sequence identity to SEQ ID NO:4, SEQ ID NO:30, or SEQ ID NO:31. An AraA polypeptide can be encoded by polynucleotide having at least about 80, 85, 90, 95, 98, 99, or 100% sequence identity to UniParc P08202-1, EMBL-EBI CP000916.1 or EMBL-EPI CP002351.

An embodiment comprises a genetically engineered microorganism comprising one or more heterologous polynucleotides encoding an alpha-glucoside permease (Agt1) polypeptide, and a psicose epimerase (Dpe). Optionally, any biological activity of an endogenous Gal1 polypeptide, an endogenous sucrose invertase (Suc2) polypeptide, an endogenous hexose kinase 1 (Hxk1) polypeptide, an endogenous hexose kinase 2 (Hxk2) polypeptide, or combinations thereof can be attenuated or eliminated. The genetically engineered microorganism can further comprise a heterologous nucleotide sequence encoding a GroES polypeptide, a GroEL chaperonin polypeptide, or both a GroES polypeptide and a GroEL polypeptide. The Agt1 polypeptide can be encoded by a polynucleotide set forth in SEQ ID NO:9, and the Dpe polypeptide can be encoded by a polynucleotide set forth in SEQ ID NO:10. The GroEL polypeptide can be encoded by a polynucleotide set forth in SEQ ID NO:15. A polynucleotide encoding an Agt1 polypeptide can have at least about 80, 85, 90, 95, 98, 99 or 100% sequence identity to SEQ ID NO:9. A polynucleotide encoding a Dpe polypeptide can have at least about 80, 85, 90, 95, 98, 99, or 100% sequence identity to SEQ ID NO:10. A polynucleotide encoding a GroEL polypeptide can have at least about 80, 85, 90, 95, 98, 99, or 100% sequence identity to SEQ ID NO:16. A polynucleotide encoding a GroES polypeptide can have at least about 80, 85, 90, 95, 98, 99, or 100% sequence identity to SEQ ID NO:14. An Agt1 polypeptide can have the amino acid sequence set forth in SEQ ID NO:11, and a Dpe polypeptide can have the amino acid sequence set forth in SEQ ID NO:12. A GroEL polypeptide can have an amino acid sequence set forth in SEQ ID NO:15. A GroES polypeptide can have an amino acid sequence set forth in SEQ ID NO:13. An Agt1 polypeptide can comprise at least about 80, 85, 90, 95, 98, 99, or 100% amino acid sequence identity to SEQ ID NO:11, and a Dpe polypeptide can comprise at least about 80, 85, 90, 95, 98, 99, or 100% amino acid sequence identity to SEQ ID NO:12. The GroEL polypeptide can comprise at least about 80, 85, 90, 95, 98, 99, or 100% amino acid sequence identity to SEQ ID NO:15. The GroES polypeptide can comprise at least about 80, 85, 90, 95, 98, 99, or 100% amino acid sequence identity to SEQ ID NO:13.

In an embodiment, a genetically engineered or recombinant microorganism has attenuated expression of a polynucleotide encoding a Gal1 polypeptide, a Suc2 polypeptide, an Hxk1 polypeptide, an Hxk2 polypeptide, or a combination thereof. Attenuated means reduced in amount, degree, intensity, or strength. Attenuated gene or polynucleotide expression can refer to a reduced amount and/or rate of transcription of the gene or polynucleotide in question. As nonlimiting examples, an attenuated gene or polynucleotide can be a mutated or disrupted gene or polynucleotide (e.g., a gene or polynucleotide disrupted by partial or total deletion, truncation, frameshifting, or insertional mutation) or that has decreased expression due to alteration or disruption of gene regulatory elements. An attenuated gene may also be a gene targeted by a construct that reduces expression of the gene or polynucleotide, such as, for example, an antisense RNA, microRNA, RNAi molecule, or ribozyme.

Attenuate also means to weaken, reduce, or diminish the biological activity of a gene product or the amount of a gene product expressed (e.g., Gal1, Hxk1, Hxk2, or Suc2 proteins) via, for example a decrease in translation, folding, or assembly of the protein. In an embodiment attenuation of a gene product (a Gal1, Hxk1, Hxk2, or Suc2 protein) means that the gene product is expressed at a rate or amount about 5, 10, 20, 30, 40, 50, 60, 70, 80, 90, 95, or 99% less (or any range between about 5 and 99% less; about 5 and 95% less; about 20 and 50% less, about 10 and 40% less, or about 10 and 90% less) than occurs in a wild-type or control organism. In an embodiment, attenuation of a gene product (e.g., a Gal1, Hxk1, Hxk2, or Suc2 protein) means that the biological activity of the gene product is about 5, 10, 20, 30, 40, 50, 60, 70, 80, 90, 95, or 99% less (or any range between about 5 and 99% less; about 5 and 95% less, about 10 and 90% less) than occurs in a wild-type or control organism.

In an embodiment a genetically engineered or recombinant microorganism expresses a polynucleotide encoding a Gal1 polypeptide, a Suc2 polypeptide, an Hxk1 polypeptide, an Hxk2 polypeptide, or combination thereof at an attenuated rate or amount (e.g., amount and/or rate of transcription of the gene or polynucleotide). An attenuated rate or amount is about 5, 10, 20, 30, 40, 50, 60, 70, 80, 90, 95, or 99% less than the rate of a wild-type or control microorganism. The result of attenuated expression of polynucleotide encoding an Hxk1 polypeptide, an Hxk2 polypeptide, a Gal1 polypeptide, a Suc2 polypeptide or combination thereof is attenuated expression of an Hxk1 polypeptide, an Hxk2 polypeptide, a Gal1 polypeptide or a Suc2 polypeptide.

Attenuated expression requires at least some expression of a biologically active wild-type or mutated Hx1 polypeptide, wild-type or mutated Hxk2 polypeptide, wild-type or mutated Gal1 polypeptide, Suc2 polypeptide, or combinations thereof.

Deleted or eliminated gene or polynucleotide expression can be gene or polynucleotide expression that is eliminated, for example, reduced to an amount that is insignificant or undetectable. Deleted or eliminated gene or polynucleotide expression can also be gene or polynucleotide expression that results in an RNA or protein that is nonfunctional, for example, deleted gene or polynucleotide expression can be gene or polynucleotide expression that results in a truncated RNA and/or polypeptide that has substantially no biological activity.

In an embodiment, a genetically engineered or recombinant microorganism has no expression of a polynucleotide encoding an Hxk1 polypeptide, an Hxk2 polypeptide, a Gal1 polypeptide, a Suc2 polypeptide, or combination thereof. The result is that substantially no Hxk1 polypeptides, Hxk2 polypeptides, Gal1 polypeptides, Suc2 polypeptides, or combinations are present in the cell.

The lack of expression can be caused by at least one gene disruption or mutation of a HXK1 gene, a HXK2 gene, a GAL1 gene, a SUC2 gene, or combinations thereof which results in no expression of the HXK1 gene, the HXK2 gene, the GAL1 gene, the SUC2 gene, or combinations thereof. For example, the lack of expression can be caused by a gene disruption in a HXK1 gene, a HXK2 gene, a GAL1 gene, or a SUC2 gene which results in attenuated or eliminated expression of the HXK1 gene, the HXK2 gene, the GAL1 gene or the SUC2 gene. Alternatively, a HXK1 gene, a HXK2 gene, a GAL1 gene, SUC2 gene, or combinations thereof can be transcribed but not translated, or the genes can be transcribed and translated, but the resulting Hxk1 polypeptide, Hxk2 polypeptide, Gal1 polypeptide, Suc2 polypeptide, or combinations thereof have substantially no biological activity.

In an embodiment, a recombinant microorganism is mutated or otherwise genetically altered such that there is substantially no expression of Gal1 polypeptides in the cell. In an embodiment, a recombinant microorganism is mutated or otherwise genetically altered such that there is substantially no expression of Hxk1, Hxk2, Suc2 polypeptides, or combinations thereof in the cell.

The polynucleotides encoding an Hxk1 polypeptide, an Hxk2 polypeptide, a Gal1 polypeptide, and a Suc2 polypeptide can be deleted or mutated using a genetic manipulation technique selected from, for example, TALEN, Zinc Finger Nucleases, and CRSPR-Cas9.

One or more regulatory elements controlling expression of the polynucleotides encoding a Hxk1 polypeptide, a Hxk2 polypeptide, a Gal1 polypeptide, a Suc2 polypeptide, or combinations thereof can be mutated or replaced to prevent or attenuate expression of a Hxk1 polypeptide, a Hxk2 polypeptide, a Gal1 polypeptide, a Suc2 polypeptide, or combinations thereof as compared to a control or wild-type microorganism. For example, a promoter can mutated or replaced such that the gene expression or polypeptide expression is attenuated or such that the HXK1, HXK2, GAL1, or SUC2 polynucleotides are not transcribed. In one embodiment, one or more promoters for HXK1, HXK2, GAL1, SUC2, or combinations thereof are replaced with a promoter that has weaker activity (e.g., TEF1p, CYC1p, ADH1p, ACT1p, HXT7p, PGI1p, TDH2p, PGK1p) than the wild-type promoter. A promoter with weaker activity transcribes the polynucleotide at a rate about 5, 10, 20, 30, 40, 50, 60, 70, 80, or 90% less than the wild-type promoter for that polynucleotide. In another embodiment, one or more promoters for HXK1, HXK2, GAL1, SUC2 or combinations thereof are replaced with an inducible promoter (e.g., TetO promoters such as TetO3, TetO7, and CUP1p) that can be controlled to attenuate expression of HXK1, HXK2, GAL1, SUC2, or combinations thereof.

The present disclosure provides genetically engineered microorganisms lacking expression or having attenuated or reduced expression of Hxk1, Hxk2, Gal1, Suc2 polypeptides or combinations thereof, or expression of mutant Hxk1, Hxk2, Gal1, Suc2 polypeptides or combinations thereof that have reduced activity. A genetically engineered or recombinant microorganism can comprise an Hxk1 polypeptide that has a T89A mutation or an Hxk2 polypeptide that has a P455F mutation. For example, in the case of Hxk1 a T89A mutation means that the T at position of the Hxk1 polypeptide is substituted with an A.

A genetically engineered or recombinant microorganism can comprise a polynucleotide encoding at least one mutant polypeptide selected from Hxk1 T89A and Hxk2 P455F.

The reduced expression, non-expression, or expression of mutated, inactive, or reduced activity polypeptides can be affected by deletion of the polynucleotide or gene encoding Hxk1, Hxk2, Gal1, and Suc2, replacement of the wild-type polynucleotide or gene with mutated forms, deletion of a portion of a HXK1, HXK2, GAL1, or SUC2 polynucleotide or gene or combinations thereof to cause expression of an inactive form of the polypeptides, or manipulation of the regulatory elements (e.g. promoter) to prevent or reduce expression of wild-type Hxk1, Hxk2, Gal1, and Suc2 polypeptides. The promoter could also be replaced with a weaker promoter or an inducible promoter that leads to reduced expression of the polypeptides. Any method of genetic manipulation that leads to a lack of, or reduced expression and/or activity of Hxk1, Hxk2, Gal1, and Suc2 polypeptides and can be used, including expression of inhibitor RNAs (e.g. shRNA, siRNA, and the like).

In an embodiment expression of SUC2 can be attenuated or eliminated by deleting the N-terminal signal sequence of SUC2 encoding sucrose invertase.

Wild-type refers to a microorganism that is naturally occurring or which has not been recombinantly modified to increase or decrease transport or utilization of specific sugars. A control microorganism is a microorganism that lacks genetic modifications of a test microorganism and that can be used to test altered biological activity of genetically modified microorganisms.

Gene Disruptions and Mutations

A genetic mutation comprises a change or changes in a nucleotide sequence of a gene or related regulatory region or polynucleotide that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be 2, 3, 4, 5, 6, 7, 8, 9, 10, or more nucleotide changes. Mutations can occur within the coding region of the gene or polynucleotide as well as within the non-coding and regulatory elements of a gene. A genetic mutation can also include silent and conservative mutations within a coding region as well as changes which alter the amino acid sequence of the polypeptide encoded by the gene or polynucleotide. A genetic mutation can, for example, increase, decrease, or otherwise alter the activity (e.g., biological activity) of the polypeptide product. A genetic mutation in a regulatory element can increase, decrease, or otherwise alter the expression of sequences operably linked to the altered regulatory element.

A gene disruption is a genetic alteration in a polynucleotide or gene that renders an encoded gene product (e.g., Hxk1, Hxk2, Gal1, Suc2) inactive or attenuated (e.g., produced at a lower amount or having lower biological activity). A gene disruption can include a disruption in a polynucleotide or gene that results in no expression of an encoded gene product, reduced expression of an encoded gene product, or expression of a gene product with reduced or attenuated biological activity. The genetic alteration can be, for example, deletion of the entire gene or polynucleotide, deletion of a regulatory element required for transcription or translation of the polynucleotide or gene, deletion of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an inactive or partially active gene product, replacement of a gene's promoter with a weaker promoter, replacement or insertion of one or more amino acids of the encoded protein to reduce its activity, stability, or concentration, or inactivation of a gene's transactivating factor such as a regulatory protein. A gene disruption can include a null mutation, which is a mutation within a gene or a region containing a gene that results in the gene not being transcribed into RNA and/or translated into a functional gene product. An inactive gene product has no biological activity.

Zinc-finger nucleases (ZFNs), Talens, and CRSPR-Cas9 allow double strand DNA cleavage at specific sites in yeast chromosomes such that targeted gene insertion or deletion can be performed (Shukla et al., 2009, Nature 459:437-441; Townsend et al., 2009, Nature 459:442-445). This approach can be used to modify the promoter of endogenous genes or the endogenous genes themselves to modify expression of Hxk1, Hxk2, Gal1, and Suc2 which can be present in the genome of yeast of interest. ZFNs, Talens or CRSPR/Cas9 can be used to change the sequences regulating the expression of the polypeptides to increase or decrease the expression or alter the timing of expression beyond that found in a non-engineered or wild-type yeast, or to delete the wild-type polynucleotide, or replace it with a deleted or mutated form to alter the expression and/or activity of Hxk1, Hxk2, Gal1, Suc2.

Polynucleotides and Genes

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragment thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., Hxk1, Hxk2, Gal1, Suc2, Cdt-1, Gh1-1, XR, Agt1, and Dpe and mutants or variants thereof).

Polynucleotides can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides can be codon optimized for expression in yeast.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein. Any process that deletes, reduces, or attenuates the expression of Hxk1, Hxk2, Gal1, and Suc2 protein expression can be used to make a microorganism described herein.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

As used herein, the term "polypeptide of interest" or "polypeptides of interest", "protein of interest", "proteins of interest" includes any or a plurality of any of the Hxk1, Hxk2, Gal1, Suc2, Cdt-1, Gh1-1, XR, Gdh, AraA, Agt1, Dpe polypeptides or other polypeptides described herein.

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et al., Molecular Cloning—A Laboratory Manual, 2nd ed., Vol. 1-3 (1989).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar Variants will be sufficiently similar to the amino acid sequence of the polypeptides described herein. Such variants generally retain the functional activity of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Polypeptides and polynucleotides that are sufficiently similar to polypeptides and polynucleotides described herein (e.g., Hxk1, Hxk2, Gal1, Suc2, Cdt-1, Gh1-1, XR, Gdh, AraA, Agt1, Dpe) can be used herein. Polypeptides and polynucleotides that about 85, 90, 95, 96, 97, 98, 99% or more homology or identity to polypeptides and polynucleotides described herein (e.g., Hxk1, Hxk2, Gal1, Suc2, Cdt-1, Gh1-1, XR, Gdh, AraA, Agt1, Dpe) can also be used herein.

Constructs and Cassettes

A recombinant construct is a polynucleotide having heterologous polynucleotide elements. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence as well.

An "expression cassette" refers to a fragment of DNA comprising a coding sequence of a selected gene (e.g. HXK1, HXK2, Glk1, SUC2, CDT-1, GH1-1, XR, GDH, ARAA, AGT1, DPE) and regulatory elements preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette is usually included within a vector, to facilitate cloning and transformation. Different expression cassettes can be transformed into different organisms including bacteria, yeast, plants and mammalian cells, as long as the correct regulatory elements are used for each host.

A recombinant construct or expression cassette can be contained within a vector. In addition to the components of the recombinant construct, the vector can include, one or more selectable markers, a signal which allows the vector to exist as single-stranded DNA (e.g., a M13 origin of replication), at least one multiple cloning site, and a origin of replication (e.g., a SV40 or adenovirus origin of replication).

Generally, a polynucleotide or gene that is introduced into a genetically engineered organism is part of a recombinant construct. A polynucleotide can comprise a gene of interest, e.g., a coding sequence for a protein, or can be a sequence that is capable of regulating expression of a gene, such as a regulatory element, an antisense sequence, a sense suppression sequence, or a miRNA sequence. A recombinant construct can include, for example, regulatory elements operably linked 5' or 3' to a polynucleotide encoding one or more polypeptides of interest. For example, a promoter can be operably linked with a polynucleotide encoding one or more polypeptides of interest when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, and translational termination regions) and/or the polynucleotide encoding a signal anchor can be native/analogous to the host cell or to each other. Alternatively, the regulatory elements can be heterologous to the host cell or to each other. See, U.S. Pat. No. 7,205,453 and U.S. Patent Application Publication Nos. 2006/0218670 and 2006/0248616. The expression cassette or recombinant construct can additionally contain one or more selectable marker genes.

Methods for preparing polynucleotides operably linked to a regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of the regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or may be partially or totally synthetic. Guidance for the design of promoters is derived from studies of promoter structure, such as that of Harley and Reynolds, *Nucleic Acids Res.,* 15, 2343-61 (1987). In addition, the location of the promoter relative to the transcription start can be optimized. Many suitable promoters for use in microorganisms and yeast are well known in the art, as are polynucleotides that enhance expression of an associated expressible polynucleotide.

A selectable marker can provide a means to identify microorganisms that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol.* (*Life Sci. Adv.*) 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase which allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, N Y (1992); Guthrie and Fink, *Guide to Yeast Genetics and Molecular Biology*, Academic Press, N Y (1991); Harlow and Lane, Antibodies, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology,* 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference (RNAi): The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

Vectors

Vectors for stable transformation of microorganisms and yeast are well known in the art and can be obtained from commercial vendors or constructed from publicly available sequence information. Expression vectors can be engineered to produce heterologous and/or homologous protein(s) of interest (e.g., Hxk1, Hxk2, Gal1, Suc2, Cdt-1, Gh1-1, XR, Gdh, AraA, Agt1, Dpe). Such vectors are useful for recombinantly producing a protein of interest and for modifying the natural phenotype of host cells.

If desired, polynucleotides can be cloned into an expression vector comprising expression control elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus vectors, retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay. Once recombinant organisms have been obtained, they may be grown in cell culture.

Methods of Use

Embodiments provide methods of fermenting compositions comprising sugars with genetically modified microorganisms described herein. A genetically modified organism is contacted with the substrates containing sugars under fermentation conditions such that the sugars are fermented.

Substrates containing sugars can be, for example, feedstocks such as terrestrial biomass feedstock (e.g., lignocellulosic biomass feedstock) or marine biomass feedstock. Feedstocks such as acid whey can also be used in the methods described herein. Feedstocks are substance used as a raw material for the growth of an organism, including an industrial growth process. A feedstock can be the raw material used to supply a carbon or other energy source for a recombinant microorganism.

In fermentation processes a genetically modified microorganism is cultivated in a fermentation medium or substrate that includes, for example sugars. A batch or continuous fermentation process can be used. The sugars can be, for example, pentose or hexose sugars, the sugars can be, for example, glucose, galactose, lactose, sucrose, arabinose, mannose, fructose, xylobiose, cellobiose, xylose, rhamnose, maltose, cellodextrins, or 4-deoxy-L-erythro-5-hexoseulose uronate. In an embodiment, two or more sugars are fermented. The fermentation medium or substrate can contain nutrients as required by the particular microorganism, including a source of nitrogen (such as amino acids proteins, inorganic nitrogen sources such as ammonia or ammonium salts, and the like), and various vitamins, minerals and the like.

Fermentation conditions, such as temperature, cell density, selection of substrate(s), selection of nutrients, and can be determined by those of skill in the art. Temperatures of the medium during each of the growth phase and the production phase can range from above about 1° C. to about 50° C. The optimal temperature can depend on the particular microorganism used. In an embodiment, the temperature is about 30, 35, 40, 45, 50° C.

During the production phase, the concentration of cells in the fermentation medium can be in the range of about 1 to about 150, about 3 to about 10, or about 3 to about 6 g dry cells/liter of fermentation medium.

A fermentation can be conducted aerobically, microaerobically or anaerobically. Fermentation medium can be buffered during the fermentation so that the pH is maintained in a range of about 5.0 to about 9.0, or about 5.5 to about 7.0. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like. The fermentation methods can be conducted continuously, batch-wise, or some combination thereof.

A fermentation reaction can be conducted over about 1, 2, 5, 10, 15, 20, 24, 25, 30, 36, 48, 50, 60, 70, 80, 90, or more or hours. Determinations of sugar consumption can be conducted after about 1, 2, 5, 10, 15, 20, 24, 25, 30, 36, 48, 50, 60, 70, 80, 90, or more or hours of fermentation by recombinant microorganisms. Determinations of product formation (e.g., amount of tagatose or psicose) can be conducted after about 1, 2, 5, 10, 15, 20, 24, 25, 30, 36, 48, 50, 60, 70, 80, 90, or more or hours of fermentation by recombinant microorganisms.

An embodiment is provided for a method for producing tagatose comprising culturing a recombinant microorganism described herein with a substrate under conditions to produce the tagatose. In an embodiment the recombinant microorganism comprises one or more heterologous polynucleotides encoding a cellodextrin transporter (Cdt-1) polypeptide, a β-galactosidase (Gh1-1) polypeptide, a xylose reductase (XR) polypeptide, and a galactitol 2-dehydrogenase (Gdh) polypeptide, wherein any biological activity of endogenous Gal1 polypeptide is attenuated or eliminated. Optionally, a heterologous AraA polypeptide can additionally be included or can be used in place of a Gdh polypeptide. The AraA polypeptide can convert L-arabinose to L-ribulose. In an embodiment, the substrate contains about 2, 5, 10, 20, 30, 40, 50% or more lactose. The lactose can be transported in the cell and then converted to glucose and galactose. In an embodiment about 50, 60, 70, 80, 90, 95, 99% or more of the hydrolyzed galactose is converted to tagatose. The bioconversion yield of tagatose from lactose can be about 20, 30, 40, 50, 60, 70, 80, 90, 95% or more. About 5, 10, 15, 20, 30, 40, 50 g/L or more tagatose can be produced from about 50 g/L of lactose. In an embodiment, 90% or more of the lactose in the fermentation medium or substrate can be converted to tagatose in about 24, 48, 60, 70, 80, or 90 hours. In an embodiment, about 30, 40, 50, 60, 70, 80, 90, 95, 99% or more of the lactose in the fermentation medium or substrate can be consumed or fermented in about 24, 48, 50, 60, 70, 80, or 90 hours.

An embodiment is provided for a method of treating acid whey comprising contacting a genetically engineered microorganism described herein with the acid whey such that the acid whey is treated. The treatment can include the conversion or consumption of lactose and/or galactose in the acid whey such that after treatment, the acid whey comprises about 2, 5, 10, 20, 30, 40, 50, 60, 70% 80%, or 90% less lactose and/or galactose than the acid whey contained prior to treatment. In an embodiment, the treatment can include the reduction in acidity of the acid whey by about 2, 5, 10, 20, 30, 40, 50, 60, 70% 80%, 90% as compared to the acidity prior to treatment. The treatment of acid whey can include the production of tagatose. In an embodiment the recombinant microorganism comprises one or more heterologous polynucleotides encoding a cellodextrin transporter (Cdt-1) polypeptide, a β-galactosidase (Gh1-1) polypeptide, a xylose reductase (XR) polypeptide, and a galactitol 2-dehydrogenase (Gdh) polypeptide, wherein any biological activity of endogenous Gal1 polypeptide is attenuated or eliminated. Optionally, a heterologous AraA polypeptide can additionally be included or can be used in place of a Gdh polypeptide.

An embodiment is provided for producing psicose comprising culturing a recombinant microorganism with a substrate under conditions to produce the psicose. The substrate can comprise, for example, about 2, 5, 10, 20, 30, 40, 50, 60, 70, 80, 90% or more sucrose. The recombinant microorganism can express: a) a heterologous alpha-glucoside permease (Agt1) polypeptide for sucrose transport; b) a heterologous psicose epimerase (Dpe) polypeptide for production of psicose; and wherein biological activity of an endogenous sucrose invertase (Suc2), endogenous hexose kinase 1 (Hxk1), endogenous hexose kinase 2 (Hxk2), or combinations thereof are attenuated or eliminated. In an embodiment about 50, 60, 70, 80, 90% or more of the sucrose is converted to psicose. The bioconversion yield of psicose from sucrose can be about 20, 30, 40, 50, 60, 70% or more. About 2, 5, 10, 15, 20, 30, 40, 50 g/L or more psicose can be produced from about 50 g/L of sucrose.

The basic techniques used for transformation and expression in yeast are known in the art. Exemplary methods have been described in a number of texts for standard molecular biological manipulation (see Sambrook et al. (1989)). These methods include, for example, biolistic devices (See, for example, Sanford, Trends In Biotech., 6: 299-302, (1988)); U.S. Pat. No. 4,945,050; use of a laser beam, electroporation, microinjection or any other method capable of introducing DNA into a host cell (e.g., an NVPO).

Sequences

SEQ ID NO: 1 nucleotide sequence of CDT-1
(Neurospora crassa, GenBank XM_958708.2).
ATGTCGTCTCACGGCTCCCATGACGGGGCCAGCACCGAGAAGCATCTTGC

TACTCATGACATTGCGCCCACCCACGACGCCATCAAGATAGTGCCCAAGG

GCCATGGCCAGACAGCCACAAAGCCCGGTGCCCAAGAGAAGGAGGTCCGC

AACGCCGCCCTATTTGCGGCCATCAAGGAGTCCAATATCAAGCCCTGGAG

CAAGGAGTCCATCCACCTCTATTTCGCCATCTTCGTCGCCTTTTGTTGTG

CATGCGCCAACGGTTACGATGGTTCACTCATGACCGGAATCATCGCTATG

GACAAGTTCCAGAACCAATTCCACACTGGTGACACTGGTCCTAAAGTCTC

TGTCATCTTTTCTCTCTATACCGTTGGTGCCATGGTTGGAGCTCCCTTCG

CTGCTATCCTCTCTGATCGTTTTGGCCGTAAGAAGGGCATGTTCATCGGT

GGTATCTTTATCATTGTCGGCTCCATTATTGTTGCTAGCTCCTCCAAGCT

CGCTCAGTTTGTCGTTGGCCGCTTCGTTCTTGGCCTCGGTATCGCCATCA

TGACCGTTGCTGCCCCGGCCTACTCCATCGAAATCGCCCTCCTCACTGG

CGCGGCCGCTGCACTGGCTTCTACAACTGCGGTTGGTTCGGAGGTTCGAT

TCCTGCCGCCTGCATCACCTATGGCTGCTACTTCATTAAGAGCAACTGGT

CATGGCGTATCCCCTTGATCCTTCAGGCTTTCACGTGCCTTATCGTCATG

TCCTCCGTCTTCTTCCTCCCAGAATCCCCTCGCTTCCTATTTGCCAACGG

CCGCGACGCTGAGGCTGTTGCCTTTCTTGTCAAGTATCACGGCAACGGCG

ATCCCAATTCCAAGCTGGTGTTGCTCGAGACTGAGGAGATGAGGGACGGT

ATCAGGACCGACGGTGTCGACAAGGTCTGGTGGGATTACCGCCCGCTCTT

CATGACCCACAGCGGCCGCTGGCGCATGGCCCAGGTGCTCATGATCTCCA

```
TCTTTGGCCAGTTCTCCGGCAACGGTCTCGGTTACTTCAATACCGTCATC
TTCAAGAACATTGGTGTCACCAGCACCTCCCAACAGCTCGCCTACAACAT
CCTCAACTCCGTCATCTCCGCTATCGGTGCCTTGACCGCCGTCTCCATGA
CTGATCGTATGCCCCGCCGCGGTGCTCATTATCGGTACCTTCATGTGC
GCCGCTGCTCTTGCCACCAACTCGGGTCTTTCGGCTACTCTCGACAAGCA
GACTCAAAGAGGCACGCAAATCAACCTGAACCAGGGTATGAACGAGCAGG
ATGCCAAGGACAACGCCTACCTCCACGTCGACAGCAACTACGCCAAGGGT
GCCCTGGCCGCTTACTTCCTCTTCAACGTCATCTTCTCCTTCACCTACAC
TCCCCTCCAGGGTGTTATTCCCACCGAGGCTCTCGAGACCACCATCCGTG
GCAAGGGTCTTGCCCTTTCCGGCTTCATTGTCAACGCCATGGGCTTCATC
AACCAGTTCGCTGGCCCCATCGCTCTCCACAACATTGGCTACAAGTACAT
CTTTGTCTTTGTCGGCTGGGATCTTATCGAGACCGTCGCTTGGTACTTCT
TTGGTGTCGAATCCCAAGGCCGTACCCTCGAGCAGCTCGAATGGGTCTAC
GACCAGCCCAACCCCGTCAAGGCCTCCCTAAAAGTCGAAAAGGTCGTCGT
CCAGGCCGACGGCCATGTGTCCGAAGCTATCGTTGCTTAG

SEQ ID NO: 2 GH1-1 nucleotide sequence (Neurospora
crassa; GenBank XM_011395457.1).
ATGTCTCTTCCTAAGGATTTCCTCTGGGGCTTCGCTACTGCGGCCTATCA
GATTGAGGGTGCTATCCACGCCGACGCCGTGGCCCCTCTATCTGGGATA
CTTTCTGCAACATTCCCGGTAAAATCGCCGACGGCAGCTCTGGTGCCGTC
GCCTGCGACTCTTACAACCGCACCAAGGAGGACATTGACCTCCTCAAGTC
TCTCGGCGCCACCGCCTACCGCTTCTCCATCTCCTGGTCTCGCATCATCC
CCGTTGGTGGTCGCAACGACCCCATCAACCAGAAGGGCATCGACCACTAT
GTCAAGTTTGTCGATGACCTGCTCGAGGCTGGTATTACCCCCTTTATCAC
CCTCTTCCACTGGGATCTTCCCGATGGTCTCGACAAGCGCTACGGCGGTC
TTCTGAACCGTGAAGAGTTCCCCCTCGACTTTGAGCACTACGCCCGCACT
ATGTTCAAGGCCATTCCCAAGTGCAAGCATGGATCACCTTCAACGAGCCC
TGGTGCAGCTCCATCCTCGGCTACAACTCGGGCTACTTTGCCCCTGGCCA
CACCTCCGACCGTACCAAGTCACCCGTTGGTGACAGCGCTCGCGAGCCCT
GGATCGTCGGCCATAACCTGCTCATCGCTCACGGGCGTGCCGTCAAGGTG
TACCGAGAAGACTTCAAGCCCACGCAGGGCGGCGAGATCGGTATCACCTT
GAACGGCGACGCCACTCTTCCCTGGGATCCAGAGGACCCCTTGGACGTCG
AGGCGTGCGACCGCAAGATTGAGTTCGCCATCAGCTGGTTCGCAGACCCC
ATCTACTTTGGAAAGTACCCCGACTCGATGCGCAAACAGCTCGGTGACCG
GCTGCCCGAGTTTACGCCCGAGGAGGTGGCGCTTGTCAAGGGTTCCAACG
ACTTCTACGGCATGAACCACTACACAGCCAACTACATCAAGCACAAGAAG
GGCGTCCCTCCCGAGGACGACTTCCTCGGCAACCTCGAGACGCTCTTCTA
CAACAAGAAGGGTAACTGCATCGGGCCCGAGACCAGTCGTTCTGGCTCC
GGCCGCACGCCCAGGGCTTCCGCGACCTGCTCAACTGGCTCAGCAAGCGC
TACGGATACCCCAAGATCTACGTGACCGAGAACGGGACCAGTCTCAAGGG CGAGAACGCCATGCCGCTCAAGCAAATTGTCGAGGACGACTTCCGCGTCA
AGTACTTCAACGACTACGTCAACGCCATGGCCAAGGCGCATAGCGAGGAC
GGCGTCAACGTCAAGGGATATCTTGCCTGGAGCTTGATGGACAACTTTGA
GTGGGCCGAGGGCTATGAGACGCGGTTCGGCGTTACCTATGTCGACTATG
AGAACGACCAGAAGAGGTACCCCAAGAAGAGCGCCAAGAGCTTGAAGCCG
CTCTTTGACTCTTTGATCAAGAAGGACTAA SEQ ID NO: 3. Nucleotide sequence of XR
(Scheffersomyces stipites; GenBank XM_001385144.1).
ATGCCTTCTATTAAGTTGAACTCTGGTTACGACATGCCAGCCGTCGGTTT
CGGCTGTTGGAAAGTCGACGTCGACACCTGTTCTGAACAGATCTACCGTG
CTATCAAGACCGGTTACAGATTGTTCGACGGTGCCGAAGATTACGCCAAC
GAAAAGTTAGTTGGTGCCGGTGTCAAGAAGGCCATTGACGAAGGTATCGT
CAAGCGTGAAGACTTGTTCCTTACCTCCAAGTTGTGGAACAACTACCACC
ACCCAGACAACGTCGAAAAGGCCTTGAACAGAACCCTTTCTGACTTGCAA
GTTGACTACGTTGACTTGTTCTTGATCCACTTCCCAGTCACCTTCAAGTT
CGTTCCATTAGAAGAAAAGTACCCACCAGGATTCTACTGTGGTAAGGGTG
ACAACTTCGACTACGAAGATGTTCCAATTTTAGAGACCTGGAAGGCTCTT
GAAAAGTTGGTCAAGGCCGGTAAGATCAGATCTATCGGTGTTTCTAACTT
CCCAGGTGCTTTGCTCTTGGACTTGTTGAGAGGTGCTACCATCAAGCCAT
CTGTCTTGCAAGTTGAACACCACCCATACTTGCAACAACCAAGATTGATC
GAATTCGCTCAATCCCGTGGTATTGCTGTCACCGCTTACTCTTCGTTCGG
TCCTCAATCTTTCGTTGAATTGAACCAAGGTAGAGCTTTGAACACTTCTC
CATTGTTCGAGAACGAAACTATCAAGGCTATCGCTGCTAAGCACGGTAAG
TCTCCAGCTCAAGTCTTGTTGAGATGGTCTTCCCAAAGAGGCATTGCCAT
CATTCCAAAGTCCAACACTGTCCCAAGATTGTTGGAAAACAAGGACGTCA
ACAGCTTGACTTGGACGAACAAGATTTCGCTGACATTGCCAAGTTGGAC
ATCAACTTGAGATTCAACGACCCATGGGACTGGGACAAGATTCCTATCTT
CGTCTAA SEQ ID NO: 4 Nucleotide sequence of GDH (Rhizobium
legumenosarum)
ATGTCTTATCAGCAAAAGTTTCGTTTAGATGGTGAAAGGGCTGTGGTTAC
AGGAGGCGGCAGAGCAATTGGTCTTTGTTGTACTGAGGCTTTGGCTGAAG
CAGGTGCCGCTGTTGTTGTAATAGAGAGGTCTGAAGCTGACGCTGAACAA
GCTCTAGCACTTAGAAACAGAGGATACGATGTTGAAGTCAGAGTTGGTGA
TGTTACTGATGCGGCAAGGATGGACGCTATAGCTACTGAATTAGCTGACG
GTGGTCGTCCAGCAACAATCCTGGTTAACAACGCTGGTATCGGTCAGAGT
GGGATTCCTGCGCAAGATCTAACAGACGCAGATTGGTTGAGAATGATGGA
TGTTAATCTGAATGGTGTTTTTTGGTGTTCCCGTGCTTTCGGAAGAAGTA
TGATTTCCATGAAACGTGGTGCGATTGTCAACTTAGGGTCAATGTCAGGT
ACGATCTGCAACAGACCACAACCACAAACTGCATATAACGTAAGTAAGGC
```

```
TGCGGTCCATCATTTGACCAGATCCTTAGCTGCTGAGTGGGCACATCATG

GAATCAGGGTGAATGCTGTCGCTCCTACATACATCGAGACCCCTATGGTG

GTCGCTGTTGAAGCAAATAGGGAAAGGATTCCTTTATGGTTAGCCGATAC

TCCAATGGCACGTATGGGCACACCCGAAGAGGTAGCCTCCGCGGTACTAT

TTCTGGCATCAGGTGCTGCATCTTTAATGACGGGAGCCATAGTTAATGTT

GACGCAGGCTTCACATGTTGGTAA
```

SEQ ID NO: 5 Cdt-1 amino acid sequence (*Neurospora crassa*; UniProt: Q7SCU1).
```
MSSHGSHDGASTEKHLATHDIAPTHDAIKIVPKGHGQTATKPGAQEKEVR
NAALFAAIKESNIKPWSKESIHLYFAIFVAFCCACANGYDGSLMTGIIAM
DKFQNQFHTGDTGPKVSVIFSLYTVGAMVGAPFAAILSDRFGRKKGMFIG
GIFIIVGSIIVASSSKLAQFVVGRFVLGLGIAIMTVAAPAYSIEIAPPHW
RGRCTGFYNCGWFGGSIPAACITYGCYFIKSNWSWRIPLILQAFTCLIVM
SSVFFLPESPRFLFANGRDAEAVAFLVKYHGNGDPNSKLVLLETEEMIRD
GIRTDGVDKVWWDYRPLFMTHSGRWRMAQVLMISIFGQFSGNGLGYFNTV
IFKNIGVTSTSQQLAYNILNSVISAIGALTAVSMTDRMPRRAVLIIGTFM
CAAALATNSGLSATLDKQTQRGTQINLNQGMNEQDAKDNAYLHVDSNYAK
GALAAYFLFNVIFSFTYTPLQGVIPTEALETTIRGKGLALSGFIVNAMGF
INQFAGPIALHNIGYKYIFVFVGWDLIETVAWYFFGVESQGRTLEQLEWV
YDQPNPVKASLKVEKVVVQADGHVSEAIVA
```

SEQ ID NO: 6 Gh1-1 amino acid sequence (*Neurospora crassa*; UniProt U9W8B8).
```
MSLPKDFLWGFATAAYQIEGAIHADGRGPSIWDTFCNIPGKIADGSSGAV
ACDSYNRTKEDIDLLKSLGATAYRFSISWSRIIPVGGRNDPINQKGIDHY
VKFVDDLLEAGITPFITLFHWDLPDGLDKRYGGLLNREEFPLDFEHYART
MFKAIPKCKHWITFNEPWCSSILGYNSGYFAPGHTSDRTKSPVGDSAREP
WIVGHNLLIAHGRAVKVYREDFKPTQGGEIGITLNGDATLPWDPEDPLDV
EACDRKIEFAISWFADPIYFGKYPDSMRKQLGDRLPEFTPEEVALVKGSN
DFYGMNHYTANYIKHKKGVPPEDDFLGNLETLFYNKKGNCIGPETQSFWL
RPHAQGFRDLLNWLSKRYGYPKIYVTENGTSLKGENAMPLKQIVEDDFRV
KYFNDYVNAMAKAHSEDGVNVKGYLAWSLMDNFEWAEGYETRFGVTYVDY
ENDQKRYPKKSAKSLKPLFDSLIKKD
```

SEQ ID NO: 7 XR amino acid sequence (*Scheffersomyces stipites*; UniProt: P31867)
```
MPSIKLNSGYDMPAVGFGCWKVDVDTCSEQIYRAIKTGYRLFDGAEDYAN
EKLVGAGVKKAIDEGIVKREDLFLTSKLWNNYHHPDNVEKALNRTLSDLQ
VDYVDLFLIHFPVTFKFVPLEEKYPPGFYCGKGDNFDYEDVPILETWKAL
EKLVKAGKIRSIGVSNFPGALLLDLLRGATIKPSVLQVEHHPYLQQPRLI
EFAQSRGIAVTAYSSFGPQSFVELNQGRALNTSPLFENETIKAIAAKHGK
SPAQVLLRWSSQRGIAIIPKSNTVPRLLENKDVNSFDLDEQDFADIAKLD
INLRFNDPWDWDKIPIFV
```

SEQ ID NO: 8 The polypeptide sequence of Gdh; NCBI WP_011650422.1).
```
MSYQQKFRLDGERAVVTGGGRAIGLCCTEALAEAGAAVVVIERSEADAEQ
ALALRNRGYDVEVRVGDVTDAARMDAIATELADGGRPATILVNNAGIGQS
GIPAQDLTDADWLRMMDVNLNGVFWCSRAFGRSMISMKRGAIVNLGSMSG
TICNRPQPQTAYNVSKAAVHHLTRSLAAEWAHHGIRVNAVAPTYIETPMV
VAVEANRERIPLWLADTPMARMGTPEEVASAVLFLASGAASLMTGAIVNV
DAGFTCW
```

SEQ ID NO: 30 Yeast codon optimized sequence of GDH
```
ATGTCCTATCAACAGAAGTTCAGGCTTGATGGTGAAAGGGCTGTTGTTAC
TGGTGGTGGAAGAGCAATTGGGTTGTGCTGCACCGAAGCTTTAGCTGAAG
CGGGCGCCGCTGTTGTAGTTATAGAAAGGTCCGAAGCGGACGCCGAACAA
GCTCTTGCCCTGAGAAATAGGGGCTATGACGTTGAGGTTCGTGTCGGGGA
CGTTACTGATGCGGCTAGGATGGATGCAATTGCTACCGAATTGGCGGATG
GAGGAAGACCTGCTACAATTCTGGTGAACAACGCAGGTATTGGCCAAAGT
GGTATACCAGCACAAGACTTAACGGACGCAGATTGGCTTAGAATGATGGA
TGTAAATCTAAACGGCGTCTTTTGGTGTTCCAGAGCTTTTGGACGTTCCA
TGATTTCCATGAAGAGAGGCGCCATCGTTAATCTAGGTTCAATGTCTGGT
ACAATTTGCAATAGGCCCCAACCTCAAACCGCGTATAATGTATCTAAGGC
TGCAGTCCATCATCTTACCAGAAGTTTGGCTGCCGAATGGGCTCATCACG
GCATTCGTGTGAATGCTGTTGCCCCAACTTATATTGAGACTCCTATGGTA
GTCGCCGTAGAAGCCAACAGAGAAAGGATTCCCCTATGGTTGGCAGACAC
TCCTATGGCTAGAATGGGAACTCCAGAAGAGGTGGCCAGTGCTGTTCTAT
TTCTTGCTAGTGGAGCGGCTTCCTTGATGACGGGGGCAATTGTCAACGTC
GATGCCGGGTTCACGTGTTGGTAA
```

SEQ ID NO: 31 Wild-type Nucleotide sequence of GDH
```
ATGAGCTACCAGCAGAAATTTCGCCTCGACGGCGAACGTGCGGTGGTCAC
AGGCGGAGGGCGGGCGATCGGTCTCTGCTGCACCGAGGCGCTGGCGGAGG
CGGGCGCCGCCGTCGTCGTCATCGAACGCAGCGAGGCCGACGCTGAGCAA
GCGCTTGCTCTCCGGAATAGAGGCTACGACGTCGAAGTCCGGGTCGGTGA
TGTCACCGACGCGGCCCGAATGGACGCGATCGCAACCGAGCTTGCCGATG
GCGGGCGGCCGGCGACCATCCTGGTCAACAATGCCGGAATTGGCCAGAGC
GGCATCCCGGCGCAGGATCTCACTGACGCCGATTGGCTGCGCATGATGGA
CGTCAATCTCAACGGCGTCTTCTGGTGCTCGCGCGCCTTTGGTCGTTCCA
TGATTTCGATGAAACGCGGCGCCATCGTCAACCTCGGCTCGATGTCGGGG
ACGATCTGCAACCGGCCCCAACCTCAGACGGCCTATAACGTCTCCAAGGC
```

-continued
GGCGGTCCATCACCTCACGCGCTCGTTGGCCGCCGAGTGGGCCCATCACG
GCATCAGGGTAAACGCCGTCGCGCCCACCTACATCGAGACGCCGATGGTG
GTGGCCGTCGAAGCCAATCGGGAGCGTATCCCGCTCTGGCTCGCCGACAC
GCCGATGGCGCGGATGGGAACGCCGGAAGAGGTTGCAAGCGCCGTCCTCT
TCCTCGCATCGGGCGCCGCCAGCCTCATGACCGGGGCGATCGTCAACGTC
GATGCTGGGTTCACCTGCTGG SEQ ID NO: 9 Nucleotide sequence of AGT1 1851 nt (S. cerevisiae; NM_001181418.3).
ATGAAAAATATCATTTCATTGGTAAGCAAGAAGAAGGCTGCCTCAAAAA
ATGAGGATAAAAACATTTCTGAGTCTTCAAGAGATATTGTAAACCAACA
GGAGGTTTTCAATACTGAAGATTTTGAAGAAGGGAAAAAGGATAGTGCC
TTTGAGCTAGACCACTTAGAGTTCACCACCAATTCAGCCCAGTTAGGAG
ATTCTGACGAAGATAACGAGAATGTGATTAATGAGATGAACGCTACTGA
TGATGCAAATGAAGCTAACAGCGAGGAAAAAAGCATGACTTTGAAGCAG
GCGTTGCTAAAATATCCAAAAGCAGCCCTGTGGTCCATATTAGTGTCTA
CTACCCTGGTTATGGAAGGTTATGATACCGCACTACTGAGCGCACTGTA
TGCCCTGCCAGTTTTTCAGAGAAAATTCGGTACTTTGAACGGGGAGGGT
TCTTACGAAATTACTTCCCAATGGCAGATTGGTTTAAACATGTGTGTCC
TTTGTGGTGAGATGATTGGTTTGCAAATCACGACTTATATGGTTGAATT
TATGGGGAATCGTTATACGATGATTACAGCACTTGGTTTGTTAACTGCT
TATATCTTTATCCTCTACTACTGTAAAAGTTTAGCTATGATTGCTGTGG
GACAAATTCTCTCAGCTATACCATGGGGTTGTTTCCAAAGTTTGGCTGT
TACTTATGCTTCGGAAGTTTGCCCTTTAGCATTAAGATATTACATGACC
AGTTACTCCAACATTTGTTGGTTATTTGGTCAAATCTTCGCCTCTGGTA
TTATGAAAAACTCACAAGAGAATTTAGGGAACTCCGACTTGGGCTATAA
ATTGCCATTTGCTTTACAATGGATTTGGCCTGCTCCTTTAATGATCGGT
ATCTTTTTCGCTCCTGAGTCGCCCTGGTGGTTGGTGAGAAAGGATAGGG
TCGCTGAGGCAAGAAAATCTTTAAGCAGAATTTTGAGTGGTAAAGGCGC
CGAGAAGGACATTCAAGTTGATCTTACTTTAAAGCAGATTGAATTGACT
ATTGAAAAGAAAGACTTTTAGCATCTAAATCAGGATCATTCTTTAATT
GTTTCAAGGGAGTTAATGGAAGAAGAACGAGACTTGCATGTTTAACTTG
GGTAGCTCAAAATAGTAGCGGTGCCGTTTTACTTGGTTACTCGACATAT
TTTTTTGAAAGAGCAGGTATGGCCACCGACAAGGCGTTTACTTTTTCTC
TAATTCAGTACTGTCTTGGGTTAGCGGGTACACTTTGCTCCTGGGTAAT
ATCTGGCCGTGTTGGTAGATGGACAATACTGACCTATGGTCTTGCATTT
CAAATGGTCTGCTTATTTATTATTGGTGGAATGGGTTTTGGTTCTGGAA
GCAGCGCTAGTAATGGTGCCGGTGGTTTATTGCTGGCTTTATCATTCTT
TTACAATGCTGGTATCGGTGCAGTTGTTTACTGTATCGTTGCTGAAATT
CCATCAGCGGAGTTGAGAACTAAGACTATAGTGCTGGCCCGTATTTGCT
ACAATCTCATGGCCGTTATTAACGCTATATTAACGCCCTATATGCTAAA SEQ ID NO: 10
DPE nucleotide sequence (Agrobacterium tumefaciens; KX098480.1)
ATGAAACACG GCATCTATTA TTCCTACTGG GAACATGAGT
GGAGCGCCAA GTTCGGTCCC TATATCGAGA AGGTCGCCAA
GCTCGGTTTC GACATCATCG AAGTCGCCGC CCACCATATC
AACGAATACA GCGACGCCGA ACTCGCGACC ATCAGGAAGA
GCGCGAAGGA TAACGGCATC ATCCTCACCG CCGGCATCGG
TCCGTCGAAA ACCAAGAACC TGTCGTCGGA AGATGCTGCG
GTGCGTGCGG CCGGCAAGGC GTTCTTTGAA AGAACCCTTT
CGAACGTCGC CAAGCTCGAT ATCCACACCA TCGGCGGCGC
ATTGCATTCC TATTGGCCAA TCGATTATTC GCAGCCCGTC
GACAAGGCAG GCGATTATGC GCGCGGCGTC GAGGGTATCA
ACGGCATTGC CGATTTCGCC AATGATCTCG GCATCAACCT
GTGCATCGAA GTCCTCAACC GCTTTGAAAA CCACGTCCTC
AACACGGCGG CGGAAGGCGT CGCTTTTGTG AAGGATGTCG
GCAAGAACAA TGTGAAAGTC ATGCTGGATA CCTTCCACAT
GAACATCGAG GAAGACAGTT TCGGTGACGC CATCCGCACG
GCCGGCCCGC TTCTGGGGCA CTTCCATACC GGTGAAAGCA
ATCGCCGCGT ACCGGGCAAG GCAGAATGCC CGTGGCACGA
AATCGGCCTT GCGCTGCGTG ATATCAACTA CACCGGCGCG
GTAATCATGG AGCCTTTCGT CAAGACAGGC GGCACCATCG
GCTCGGATAT CAAGGTGTGG CGCGACCTGA GCGGTGGCGC
CGACATCGCG AAAATGGATG AAGATGCCCG CAATGCGCTG
GCATTCTCCC GTTTCGTCCT TGGCGGCTGA SEQ ID NO: 11
Agt1 amino acid sequence (S. cerevisiae UniProt: P53048).
MKNIISLVSKKKAASKNEDKNISESSRDIVNQQEVFNTEDFEEGKKDSAF
ELDHLEFTTNSAQLGDSDEDNENVINEMNATDDANEANSEEKSMTLKQAL
LKYPKAALWSILVSTTLVMEGYDTALLSALYALPVFQRKFGTLNGEGSYE
ITSQWQIGLNMCVLCGEMIGLQITTYMVEFMGNRYTMITALGLLTAYIFI
LYYCKSLAMIAVGQILSAIPWGCFQSLAVTYASEVCPLALRYYMTSYSNI
CWLFGQIFASGIMKNSQENLGNSDLGYKLPFALQWIWPAPLMIGIFFAPE
SPWWLVRKDRVAEARKSLSRILSGKGAEKDIQVDLTLKQIELTIEKERLL -continued
ASKSGSFFNCFKGVNGRRTRLACLTWVAQNSSGAVLLGYSTYFFERAGMA

TDKAFTFSLIQYCLGLAGTLCSWVISGRVGRWTILTYGLAFQMVCLFIIG

GMGFGSGSSASNGAGGLLLALSFFYNAGIGAVVYCIVAEIPSAELRTKTI

VLARICYNLMAVINAILTPYMLNVSDWNWGAKTGLYWGGFTAVTLAWVII

DLPETTGRTFSEINELFNQGVPARKFASTVVDPFGKGKTQHDSLADESIS

SEQ ID NO: 12
Dpe amino acid sequence (*Agrobacterium turnefaciens*: WP_010974125.1).
MKHGIYYSYW EHEWSAKFGP YIEKVAKLGF DIIEVAAHHI

NEYSDAELAT IRKSAKDNGI ILTAGIGPSK TKNLSSEDAA

VRAAGKAFFE RTLSNVAKLD IHTIGGALHS YWPIDYSQPV

DKAGDYARGV EGINGIADFA NDLGINLCIE VLNRFENHVL

NTAAEGVAFV KDVGKNNVKV MLDTFHMNIE EDSFGDAIRT

AGPLLGHFHT GESNRRVPGK GRMPWHEIGL ALRDINYTGA

VIMEPFVKTG GTIGSDIKVW RDLSGGADIA KMDEDARNAL

AFSRFVLGG

SEQ ID NO: 13
GroES amino acid sequence (*E. coli*; UniProt: P0A6F9).
MNIRPLHDRV IVKRKEVETKSAGGIVLTGSAAAKSTRGEVLAVGNGRIL

ENGEVKPLDVKVGDIVIFNDGYGVKSEKIDNEEVLIMSESDILAIVEA

SEQ ID NO: 14
GroES nucleotide sequence (*E. coli*; CP023142.1.)
ATGAATATTCGTCCATTGCATGATCGCGTGATCGTCAAGCGTAAAGAAGT

TGAAACTAAATCTGCTGGCGGCATCGTTCTGACCGGCTCTGCAGCGGCTA

AATCCACCCGCGGCGAAGTGCTGGCTGTCGGCAATGGCCGTATCCTTGAA

AATGGCGAAGTGAAGCCGCTGGATGTGAAAGTTGGCGACATCGTTATTTT

CAACGATGGCTACGGTGTGAAATCTGAGAAGATCGACAATGAAGAAGTGT

TGATCATGTCCGAAAGCGACATTCTGGCAATTGTTGAAGCGTAA

SEQ ID NO: 15
GroEL amino acid sequence (*E.coli*; UniProt: P0A6F5).
MAAKDVKFGNDARVKMLRGVNVLADAVKVTLGPKGRNVVLDKSFGAPTIT

KDGVSVAREIELEDKFENMGAQMVKEVASKANDAAGDGTTTATVLAQAII

TEGLKAVAAGMNPMDLKRGIDKAVTAAVEELKALVPCSDSKAIAQVGTIS

ANSDETVGKLIAEAMDKVGKEGVITVEDGTGLQDELDVVEGMQFDRGYLS

PYFINKPETGAVELESPFILLADKKISNIREMLPVLEAVAKAGKPLLIIA

EDVEGEALATLVVNTMRGIVKVAAVKAPGFGDRRKAMLQDIATLTGGTVI

SEEIGMELEKATLEDLGQAKRVVINKDTTTIIDGVGEEAAIQGRVAQIRQ

QIEEATSDYDREKLQERVAKLAGGVAVIKVGAATEVEMKEKKARVEDALH

ATRAAVEEGVVAGGGVALIRVASKLADLRGQNEDQNVGIKVALRAMEAPL

RQIVLNCGEEPSVVANTVKGGDGNYGYNAATEEYGNMIDMGILDPTKVTR

SALQYAASVAGLMITTECMVTDLPKNDAADLGAAGGMGGMGGMGGMM

SEQ ID NO: 16
GroEL nucleotide sequence (*E. coli*; CP022466.1).
ATGGCAGCTAAAGACGTAAAATTCGGTAACGACGCTCGTGTGAAAATGCT

GCGCGGCGTAAACGTACTGGCAGATGCAGTGAAAGTTACCCTCGGTCCAA

AAGGCCGTAACGTAGTTCTGGATAAATCTTTCGGTGCACCGACCATCACC

AAAGATGGTGTTTCCGTTGCTCGTGAAATCGAACTGGAAGACAAGTTCGA

AAATATGGGTGCGCAGATGGTGAAAGAAGTTGCCTCTAAAGCAAACGACG

CTGCAGGCGACGGTACCACCACTGCAACCGTACTGGCTCAGGCTATCATC

ACTGAAGGTCTGAAAGCTGTTGCTGCGGGCATGAACCCGATGGACCTGAA

ACGTGGTATCGACAAAGCGGTTACCGCTGCAGTTGAAGAACTGAAAGCGC

TGTCCGTACCATGCTCTGACTCTAAAGCGATTGCTCAGGTTGGTACCATC

TCCGCTAACTCCGACGAAACCGTAGGTAAACTGATCGCTGAAGCGATGGA

CAAAGTCGGTAAAGAAGGCGTTATCACCGTTGAAGACGGTACCGGTCTGC

AGGACGAACTGGACGTGGTTGAAGGTATGCAGTTCGACCGTGGCTACCTG

TCTCCTTACTTCATCAACAAGCCGGAAACTGGCGCAGTAGAACTGGAAAG

CCCGTTCATCCTGCTGGCTGACAAGAAAATCTCCAACATCCGCGAAATGC

TGCCGGTTCTGGAAGCTGTTGCCAAAGCAGGCAAACCGCTGCTGATCATC

GCTGAAGATGTAGAAGGCGAAGCGCTGGCAACTCTGGTTGTTAACACCAT

GCGTGGCATCGTGAAAGTCGCTGCGGTTAAAGCACCGGGCTTCGGCGATC

GTCGTAAAGCTATGCTGCAGGATATCGCAACCCTGACTGGCGGTACCGTG

ATCTCTGAAGAGATCGGTATGGAGCTGGAAAAAGCAACCCTGGAAGACCT

GGGTCAGGCTAAACGTGTTGTGATCAACAAAGACACCACCACTATCATCG

ATGGCGTGGGTGAAGAAGCTGCAATCCAGGGCCGTGTTGCTCAGATCCGT

CAGCAGATTGAAGAAGCAACTTCTGACTACGACCGTGAAAAACTGCAGGA

ACGCGTAGCGAAACTGGCAGGCGGCGTTGCAGTTATCAAAGTGGGTGCTG

CTACCGAAGTTGAAATGAAAGAGAAAAAAGCACGCGTTGAAGATGCCCTG

CACGCGACCCGTGCTGCGGTAGAAGAAGGCGTGGTTGCTGGTGGTGGTGT

TGCGCTGATCCGCGTAGCGTCTAAACTGGCTGACCTGCGTGGTCAGAACG

AAGACCAGAACGTGGGTATCAAAGTTGCACTGCGTGCAATGGAAGCTCCG

CTGCGTCAGATCGTATTGAACTGCGGCGAAGAACCGTCTGTTGTTGCTAA

CACCGTTAAAGGCGGCGACGGCAACTACGGTTACAACGCAGCAACCGAAG

AATACGGCAACATGATCGACATGGGTATCCTGGATCCAACCAAAGTAACT

CGTTCTGCTCTGCAGTACGCAGCTTCTGTGGCTGGCCTGATGATCACCAC

CGAATGCATGGTTACCGACCTGCCGAAAAACGATGCAGCTGACTTAGGCG

CTGCTGGCGGTATGGGCGGCATGGGTGGCATGGGCGGCATGATGTAA

SEQ ID NO: 17
HXK1 nucleotide sequence (S. cerevisiae; NM_001180018.3).
ATGGTTCATTTAGGTCCAAAGAAACCACAGGCTAGAAAGGGTTCCATGGC
TGATGTGCCCAAGGAATTGATGGATGAAATTCATCAGTTGGAAGATATGT
TTACAGTTGACAGCGAGACCTTGAGAAAGGTTGTTAAGCACTTTATCGAC
GAATTGAATAAAGGTTTGACAAAGAAGGGAGGTAACATTCCAATGATTCC
CGGTTGGGTCATGGAATTCCCAACAGGTAAAGAATCTGGTAACTATTTGG
CCATTGATTTGGGTGGTACTAACTTAAGAGTCGTGTTGGTCAAGTTGAGC
GGTAACCATACCTTTGACACCACTCAATCCAAGTATAAACTACCACATGA
CATGAGAACCACTAAGCACCAAGAGGAGTTATGGTCCTTTATTGCCGACT
CTTTGAAGGACTTTATGGTCGAGCAAGAATTGCTAAACACCAAGGACACC
TTACCATTAGGTTTCACCTTCTCGTACCCAGCTTCCCAAAACAAGATTAA
CGAAGGTATTTTGCAAAGATGGACCAAGGGTTTCGATATTCCAAATGTCG
AAGGCCACGATGTCGTCCCATTGCTACAAAACGAAATTTCCAAGAGAGAG
TTGCCTATTGAAATTGTAGCATTGATTAATGATACTGTTGGTACTTTAAT
TGCCTCATACTACACTGACCCAGAGACTAAGATGGGTGTGATTTTCGGTA
CTGGTGTCAACGGTGCTTTCTATGATGTTGTTTCCGATATCGAAAAGTTG
GAGGGCAAATTAGCAGACGATATTCCAAGTAACTCTCCAATGGCTATCAA
TTGTGAATATGGTTCCTTCGATAATGAACATTTGGTCTTGCCAAGAACCA
AGTACGATGTTGCTGTCGACGAACAATCTCCAAGACCTGGTCAACAAGCT
TTTGAAAAGATGACCTCCGGTTACTACTTGGGTGAATTGTTGCGTCTAGT
GTTACTTGAATTAAACGAGAAGGGCTTGATGTTGAAGGATCAAGATCTAA
GCAAGTTGAAACAACCATACATCATGGATACCTCCTACCCAGCAAGAATC
GAGGATGATCCATTTGAAAACTTGGAAGATACTGATGACATCTTCCAAAA
GGACTTTGGTGTCAAGACCACTCTGCCAGAACGTAAGTTGATTAGAAGAC
TTTGTGAATTGATCGGTACCAGAGCTGCTAGATTAGCTGTTTGTGGTATT
GCCGCTATTTGCCAAAAGAGAGGTTACAAGACTGGTCACATTGCCGCTGA
CGGTTCTGTCTATAACAAATACCCAGGTTTCAAGGAAGCCGCCGCTAAGG
GTTTGAGAGATATCTATGGATGGACTGGTGACGCAAGCAAAGATCCAATT
ACGATTGTTCCAGCTGAGGATGGTTCAGGTGCAGGTGCTGCTGTTATTGC
TGCATTGTCCGAAAAAAGAATTGCCGAAGGTAAGTCTCTTGGTATCATTG
GCGCTTAA SEQ ID NO: 18
Hxk1 amino acid sequence (S. cerevisiae; UniProt: P04806).
MVHLGPKKPQARKGSMADVPKELMDEIHQLEDMFTVDSETLRKVVKHFIDE
LNKGLTKKGGNIPMIPGWVMEFPTGKESGNYLAIDLGGTNLRVVLVKLSGN
HTFDTTQSKYKLPHDMIRTTKHQEELWSFIADSLKDFMVEQELLNTKDTLP
LGFTFSYPASQNKINEGILQRWTKGFDIPNVEGHDVVPLLQNEISKRELPI
EIVALINDTVGTLIASYYTDPETKMGVIFGTGVNGAFYDVVSDIEKLEGKL
ADDIPSNSPMAINCEYGSFDNEHLVLPRTKYDVAVDEQSPRPGQQAFEKMT
SGYYLGELLRLVLLELNEKGLMLKDQDLSKLKQPYIMDTSYPARIEDDPFE
NLEDTDDIFQKDFGVKTTLPERKLIRRLCELIGTRAARLAVCGIAAICQKR
GYKTGHIAADGSVYNKYPGFKEAAAKGLRDIYGWTGDASKDPITIVPAEDG
SGAGAAVIAALSEKRIAEGKSL SEQ ID NO: 19
HXK2 nucleotide sequence (S. cerevisiae; NM_001181119.1).
ATGGTTCATTTAGGTCCAAAAAAACCACAAGCCAGAAAGGGTTCCATGGC
CGATGTGCCAAAGGAATTGATGCAACAAATTGAGAATTTTGAAAAAATTT
TCACTGTTCCAACTGAAACTTTACAAGCCGTTACCAAGCACTTCATTTCC
GAATTGGAAAAGGGTTTGTCCAAGAAGGGTGGTAACATTCCAATGATTCC
AGGTTGGGTTATGGATTTCCCAACTGGTAAGGAATCCGGTGATTTCTTGG
CCATTGATTTGGGTGGTACCAACTTGAGAGTTGTCTTAGTCAAGTTGGGC
GGTGACCGTACCTTTGACACCACTCAATCTAAGTACAGATTACCAGATGC
TATGAGAACTACTCAAAATCCAGACGAATTGTGGGAATTTATTGCCGACT
CTTTGAAAGCTTTTATTGATGAGCAATTCCCACAAGGTATCTCTGAGCCA
ATTCCATTGGGTTTCACCTTTTCTTTCCCAGCTTCTCAAAACAAAATCAA
TGAAGGTATCTTGCAAAGATGGACTAAAGGTTTTGATATTCCAAACATTG
AAAACCACGATGTTGTTCCAATGTTGCAAAAGCAAATCACTAAGAGGAAT
ATCCCAATTGAAGTTGTTGCTTTGATAAACGACACTACCGGTACTTTGGT
TGCTTCTTACTACACTGACCCAGAAACTAAGATGGGTGTTATCTTCGGTA
CTGGTGTCAATGGTGCTTACTACGATGTTGTTCCGATATCGAAAAGCTA
CAAGGAAAACTATCTGATGACATTCCACCATCTGCTCCAATGGCCATCAA
CTGTGAATACGGTTCCTTCGATAATGAACATGTCGTTTTGCCAAGAACTA
AATACGATATCACCATTGATGAAGAATCTCCAAGACCAGGCCAACAAACC
TTTGAAAAATGTCTTCTGGTTACTACTTAGGTGAAATTTTGCGTTTGGC
CTTGATGGACATGTACAAACAAGGTTTCATCTTCAAGAACCAAGACTTGT
CTAAGTTCGACAAGCCTTTCGTCATGGACACTTCTTACCCAGCCAGAATC
GAGGAAGATCCATTCGAGAACCTAGAAGATACCGATGACTTGTTCCAAAA
TGAGTTCGGTATCAACACTACTGTTCAAGAACGTAAATTGATCAGACGTT
TATCTGAATTGATTGGTGCTAGAGCTGCTAGATTGTCCGTTTGTGGTATT
GCTGCTATCTGTCAAAAGAGAGGTTACAAGACCGGTCACATCGCTGCAGA
CGGTTCCGTTTACAACAGATACCCAGGTTTCAAAGAAAAGGCTGCCAATG
CTTTGAAGGACATTTACGCTGGACTCAAACCTCACTAGACGACTACCCA
ATCAAGATTGTTCCTGCTGAAGATGGTTCCGGTGCTGGTGCCGCTGTTAT
TGCTGCTTTGGCCCAAAAAAGAATTGCTGAAGGTAAGTCCGTTGGTATCA
TCGGTGCTTAA SEQ ID NO: 20
Hxk2 amino acid sequence (*S. cerevisiae*;
AAA34699.1).
MVHLGPKKPQARKGSMADVPKELMQQIENFEKIFTVPTETLQAVTKHFIS

ELEKGLSKKGGNIPMIPGWVMDFPTGKESGDFLAIDLGGTNLRVVLVKLG

GDRTFDTTQSKYRLPDAMRTTQNPDELWEFIADSLKAFIDEQFPQGISEP

IPLGFTFSFPASQNKINEGILQRWTKGFDIPNIENHDVVPMLQKQITKRN

IPIEVVALINDTTGTLVASYYTDPETKMGVIFGTGVNGAYYDVCSDIEKL

QGKLSDDIPPSAPMAINCEYGSFDNEHVVLPRTKYDITIDEESPRPGQQT

FEKMSSGYYLGEILRLALMDMYKQGFIFKNQDLSKFDKPFVMDTSYPARI

EEDPFENLEDTDDLFQNEFGINTTVQERKLIRRLSELIGARAARLSVCGI

AAICQKRGYKTGHIAADGSVYNRYPGFKEKAANALKDIYGWTQTSLDDYP

IKIVPAEDGSGAGAAVIAALAQKRIAEGKSVGIIGA

SEQ ID NO: 21
SUC2 nucleotide sequence (*S. cerevisiae*;
NM_001179510.1).
ATGCTTTTGCAAGCTTTCCTTTTCCTTTTGGCTGGTTTTGCAGCCAAAAT

ATCTGCATCAATGACAAACGAAACTAGCGATAGACCTTTGGTCCACTTCA

CACCCAACAAGGGCTGGATGAATGACCCAAATGGGTTGTGGTACGATGAA

AAAGATGCCAAATGGCATCTGTACTTTCAATACAACCCAAATGACACCGT

ATGGGGTACGCCATTGTTTTGGGGCCATGCTACTTCCGATGATTTGACTA

ATTGGGAAGATCAACCCATTGCTATCGCTCCCAAGCGTAACGATTCAGGT

GCTTTCTCTGGCTCCATGGTGGTTGATTACAACAACACGAGTGGGTTTTT

CAATGATACTATTGATCCAAGACAAAGATGCGTTGCGATTTGGACTTATA

ACACTCCTGAAAGTGAAGAGCAATACATTAGCTATTCTCTTGATGGTGGT

TACACTTTTACTGAATACCAAAAGAACCCTGTTTTAGCTGCCAACTCCAC

TCAATTCAGAGATCCAAAGGTGTTCTGGTATGAACCTTCTCAAAAATGGA

TTATGACGGCTGCCAAATCACAAGACTACAAAATTGAAATTTACTCCTCT

GATGACTTGAAGTCCTGGAAGCTAGAATCTGCATTTGCCAATGAAGGTTT

CTTAGGCTACCAATACGAATGTCCAGGTTTGATTGAAGTCCCAACTGAGC

AAGATCCTTCCAAATCTTATTGGGTCATGTTTATTTCTATCAACCCAGGT

GCACCTGCTGGCGGTTCCTTCAACCAATATTTTGTTGGATCCTTCAATGG

TACTCATTTTGAAGCGTTTGACAATCAATCTAGAGTGGTAGATTTTGGTA

AGGACTACTATGCCTTGCAAACTTTCTTCAACACTGACCCAACCTACGGT

TCAGCATTAGGTATTGCCTGGGCTTCAAACTGGGAGTACAGTGCCTTTGT

CCCAACTAACCCATGGAGATCATCCATGTCTTTGGTCCGCAAGTTTTCTT

TGAACACTGAATATCAAGCTAATCCAGAGACTGAATTGATCAATTTGAAA

GCCGAACCAATATTGAACATTAGTAATGCTGGTCCTGGTCTCGTTTTGC

TACTAACACAACTCTAACTAAGGCCAATTCTTACAATGTCGATTTGAGCA

ACTCGACTGGTACCCTAGAGTTTGAGTTGGTTTACGCTGTTAACACCACA

CAAACCATATCCAAATCCGTCTTTGCCGACTTATCACTTTGGTTCAAGGG

TTTAGAAGATCCTGAAGAATATTTGAGAATGGGTTTTGAAGTCAGTGCTT

CTTCCTTCTTTTTGGACCGTGGTAACTCTAAGGTCAAGTTTGTCAAGGAG

AACCCATATTTCACAAACAGAATGTCTGTCAACAACCAACCATTCAAGTC

TGAGAACGACCTAAGTTACTATAAAGTGTACGGCCTACTGGATCAAAACA

TCTTGGAATTGTACTTCAACGATGGAGATGTGGTTTCTACAAATACCTAC

TTCATGACCACCGGTAACGCTCTAGGATCTGTGAACATGACCACTGGTGT

CGATAATTTGTTCTACATTGACAAGTTCCAAGTAAGGGAAGTAAAATAG

SEQ ID NO: 22
Suc2 amino acid sequence (*S. cerevisiae*;
UniProt: P00724).
MLLQAFLFLLAGFAAKISASMTNETSDRPLVHFTPNKGWMNDPNGLWYD

EKDAKWHLYFQYNPNDTVWGTPLFWGHATSDDLTNWEDQPIAIAPKRNDS

GAFSGSMVVDYNNTSGFFNDTIDPRQRCVAIWTYNTPESEEQYISYSLDG

GYTFTEYQKNPVLAANSTQFRDPKVFWYEPSQKWIMTAAKSQDYKIEIYS

SDDLKSWKLESAFANEGFLGYQYECPGLIEVPTEQDPSKSYWVMFISINP

GAPAGGSFNQYFVGSFNGTHFEAFDNQSRVVDFGKDYYALQTFFNTDPT

YGSALGIAWASNWEYSAFVPTNPWRSSMSLVRKFSLNTEYQANPETELIN

LKAEPILNISNAGPWSRFATNTTLTKANSYNVDLSNSTGTLEFELVYAVN

TTQTISKSVFADLSLWFKGLEDPEEYLRMGFEVSASSFFLDRGNSKVKFV

KENPYFTNRMSVNNQPFKSENDLSYYKVYGLLDQNILELYFNDGDVVSTN

TYFMTTGNALGSVNMTTGVDNLFYIDKFQVREVK

SEQ ID NO: 29
Gal1 (*S. cerevisiae* CAA84962.1)(others include
for example, KZV13090.1; EWH19436.1; EWG97615.1)
MTKSHSEEVI VPEFNSSAKE LPRPLAEKCP SIIKKFISAY

DAKPDFVARS PGRVNLIGEH IDYCDFSVLP LAIDFDMLCA

VKVLNEKNPS ITLINADPKF AQRKFDLPLD GSYVTIDPSV

SDWSNYFKCG LHVAHSFLKK LAPERFASAP LAGLQVFCEG

DVPTGSGLSS SAAFICAVAL AVVKANMGPG YHMSKQNLMR

ITVVAEHYVG VNNGGMDQAA SVCGEEDHAL YVEFKPQLKA

TPFKFPQLKN HEISFVIANT LVVSNKFETA PTNYNLRVVE

VTTAANVLAA TYGVVLLSGK EGSSTNKGNL RDFMNVYYAR

YHNISTPWNG DIESGIERLT KMLVLVEESL ANKKQGFSVD

DVAQSLNCSR EEFTRDYLTT SPVRFQVLKL YQRAKHVYSE

SLRVLKAVKL MTTASFTADE DFFKQFGALM NESQASCDKL

YECSCPEIDK ICSIALSNGS YGSRLTGAGW GGCTVHLVPG

GPNGNIEKVK EALANEFYKV KYPKITDAEL ENAIIVSKPA

LGSCLYEL

SEQ ID NO: 32
AraA polypeptide sequence UniParc P08202-1
MTIFDNYEVW FVIGSQHLYG PETLRQVTQH AEHVVNALNT
          60         70         80         90
EAKLPCKLVL KPLGTTPDEI TAICRDANYD DRCAGLVVWL -continued

```
           100        110        120        130
HTFSPAKMWI NGLTMLNKPL LQFHTQFNAA LPWDSIDMDF 140        150        160        170
MNLNQTAHGG REFGFIGARM RQQHAVVTGH WQDKQAHERI 180        190        200        210
GSWMRQAVSK QDTRHLKVCR FGDNMREVAV TDGDKVAAQI 220        230        240        250
KFGFSVNTWA VGDLVQVVNS ISDGDVNALV DEYESCYTMT 260        270        280        290
PATQIHGKKR QNVLEAARIE LGMKRFLEQG GFHAFTTTFE 300        310        320        330
DLHGLKQLPG LAVQRLMQQG YGFAGEGDWK TAALLRIMKV 340        350        360        370
MSTGLQGGTS FMEDYTYHFE KGNDLVLGSH MLEVCPSIAA 380        390        400        410
EEKPILDVQH LGIGGKDDPA RLIFNTQTGP AIVASLIDLG 420        430        440        450
DRYRLLVNCI DTVKTPHSLP KLPVANALWK AQPDLPTASE 460        470        480        490
AWILAGGAHH TVFSHALNLN DMRQFAEMHD IEITVIDNDT

500
RLPAFKDALR WNEVYYGFRR
```

TABLE I

Primers used in this study.

| Primers | Primer sequences | Source |
|---|---|---|
| Gal1-gU | aaaggaattaccaagaccatgtttagagctagaaatagcaag SEQ ID NO:23 | This study |
| Gal1-gD | atggtatggtaattcctttgatcatttatattcactgcgga SEQ ID NO:24 | This study |
| Gal1-Donnor-U | gtatcaacaaaaaattgttaatatacctctatactttaacgtcaaggaga aaaaactatagtatacttcttttttt SEQ ID NO:25 | This study |
| Gal1-Donnor-D | aagttatgagtagaaaaaaatgagaagttgttctgaacaaagtaaaaaaaa agaagtatactatagttttttctcc SEQ ID NO:26 | This study |
| Gal1-CK-U | ctgaaacgcagatgtgcctcg SEQ ID NO:27 | This study |
| Gal1-CK-D | ggtagtcatatcatgtcaag SEQ ID NO:28 | This study |

TABLE II

Plasmids used in this study

| Plasmids | Description | Source |
|---|---|---|
| pRS42K | pRS42K | (18) |
| pRS42H | pRS42H | (18) |
| pYS10 | pRS305 pTDH3-XYL1-tTDH3 | (19) |
| p42K-XR | pRS42K pTDH3-XYL1-tTDH3 | This study |
| p426-pGPD | pSR426 pTDH3-tCYC1 | (17) |
| p42K-pGPD | pRS42K pTDH3-tCYC1 | (15) |
| p42H-pGPD | pRS42H pTDH3-tCYC1 | This study |
| p42H-GDH | pRS42H pTDH3-GDH-tCYC1 | This study |
| CAS9-NAT | p414-TEF1p-Cas9-CYC1t-NAT1 | (15) |
| p42K-gCS8 | pRS42K carrying guide RNA for integration at CS8 locus | (15) |
| p42H-gCS6 | pRS42H carrying guide RNA for integration at CS6 locus | This study |

TABLE III

The engineered S. cerevisiae strains used in this study.

| Strains | Description | Source |
|---|---|---|
| EJ2 | Evolved strain of EJ1 (D452-2 leu2::LEU2 pRS405-gh1-1 ura3::URA3 pRS406-cdt-1) | (16) |
| EJ2g | EJ2 GAL1 deletion by Cas9 | This study |
| EJ2g (X) | EJ2g with p42K-XR | This study |
| EJ2g (XG) | EJ2g with p42K-XR and p42H-GDH | This study |
| EJ2g X | EJ2g with integrated pTDH3-XYL1-tTDH3 | This study |
| EJ2g G | EJ2g with integrated pTDH3-GDH-tCYC1 | This study |
| EJ2g XG | EJ2g with integrated pTDH3-XYL1-tTDH3 and pTDH3-GDH-tCYC1 | This study |
| EJ2g XG (X) | EJ2g XG with p42K-XR | This study |
| EJ2g XG (G) | EJ2g XG with p42H-GDH | This study |
| EJ2g XG (XG) | EJ2g XG with p42K-XR and p42H-GDH | This study |

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1. A Metabolic Design to Accumulate Intracellular Galactose in Engineered Yeast An engineered strain (EJ2) capable of utilizing cellobiose intracellularly through introduction of cellobiose transporter (Cdt-1) and beta-glucosidase (Gh1-1) was constructed. Interestingly, the engineered yeast was also able to utilize lactose intracellularly. This result suggests that Cdt-1 can transport lactose and Gh1-1 can hydrolyze lactose as well as cellobiose. In order to accumulate galactose intracellularly, GAL1 coding for galactose kinase was deleted, which is the first step of the Leloir pathway responsible for galactose assimilation in yeast and other eukaryotes. The GAL1 deleted strain (EJ2g) accumulated galactose during lactose utilization (FIG. 1), suggesting only glucose from lactose was consumed by yeast and intracellular accumulation of galactose led to secretion of galactose into fermentation medium. In contrast, the parental strain (EJ2) did not accumulate galactose during lactose utilization. This GAL1 deleted lactose-utilizing yeast strain (EJ2g) can be used as a host strain for intracellular conversion of galactose into other value added chemicals. Tagatose which is an isomer of galactose was produced. Tagatose can be used to replace sugar as a sweetener. In this case, glucose from lactose is utilized by yeast for the production of bioconversion enzymes, providing necessary cofactors, and cell maintenance energy and galactose is intracellularly converted into tagatose. If glucose and galactose is provided extracellularly, galactose cannot be transported into the cytosol when glucose is present because of glucose repression. Therefore, efficient conversion of galactose through the metabolic activities of glucose cannot achieved.

Figure 2:
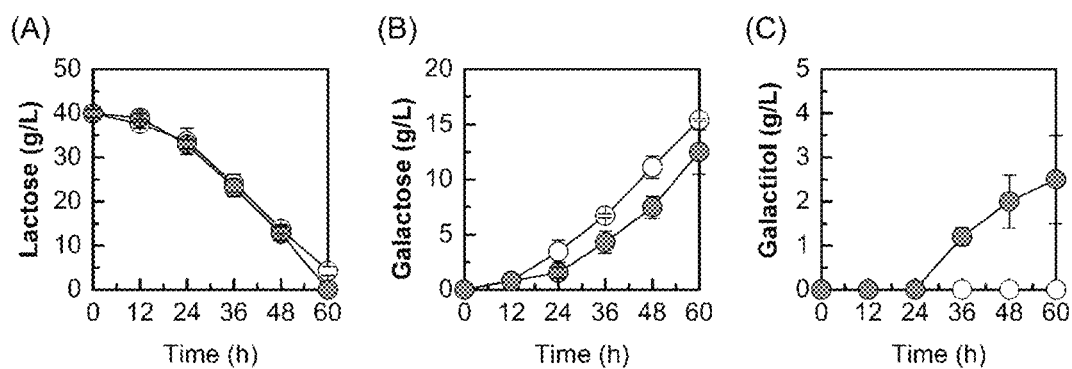
FIG. 2 panels A-C. Galactitol is produced by introducing xylose reductase (XR) in to the EJ2g strain. A: The fermentation profile of yeast strain expressing CDT-1 and GH1-1 with GAL1 deletion on YP with 40 g/L of lactose under micro-aerobic condition; B: The fermentation profile of yeast strain expressing CDT-1 and GH1-1 with GAL1 deletion and XR overexpression driven by TDH3 promoter on YP with 40 g/L of lactose under micro-aerobic condition. Data are presented as mean value and standard deviations of three independent biological replicates.
Figure 3:
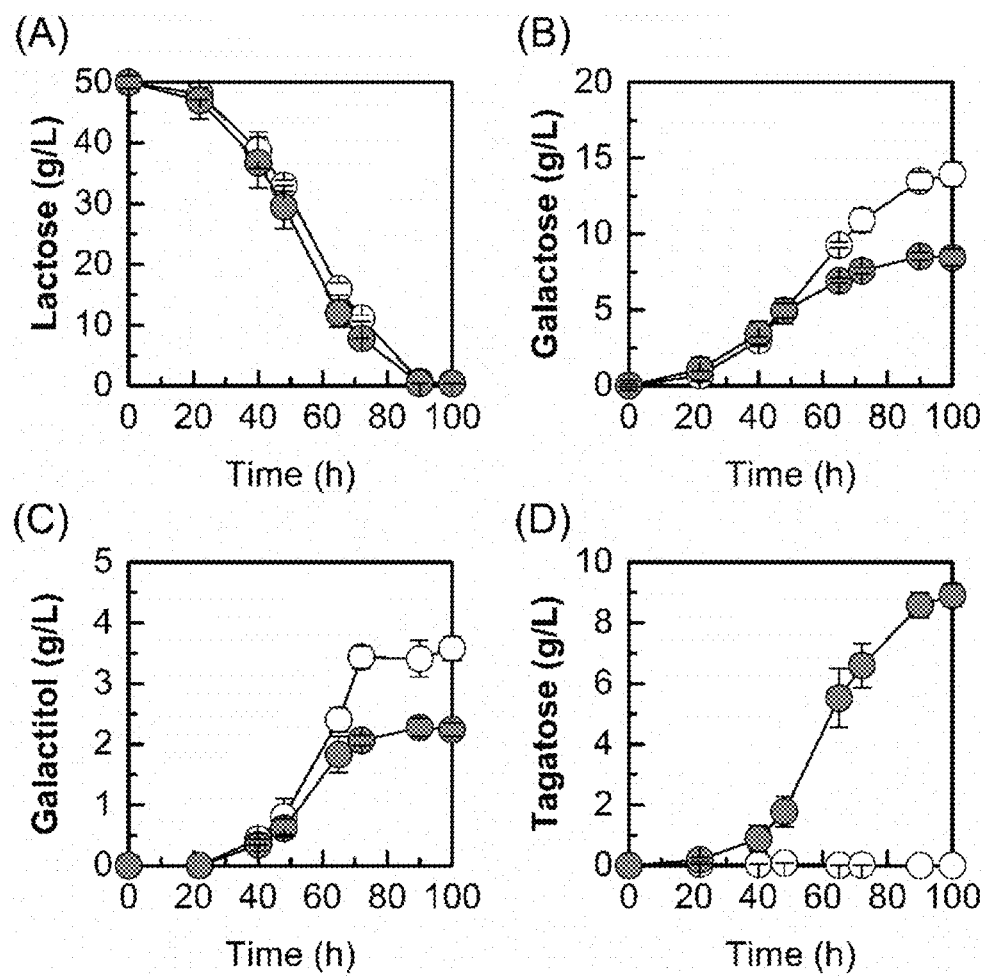
FIG. 3 panels A-D. Tagatose is detected by introducing galactitol 2-dehydrogenase (GDH) into EJ2 GAL1 XR background under aerobic condition. A: lactose consumption; B: galactose production; C: galactitol production; D: Tagatose production. Symbols: square: yeast strain expressing CDT-1 and GH1-1 with GAL1 deletion and XR overexpression; circle: yeast strain expressing CDT-1 and GH1-1 with GAL1 deletion and XR and GDH overexpression. Data are presented as mean value and standard deviations of three independent biological replicates.

Example 2. Two Step Oxidoreductase Reactions to Convert Galactose into Tagatose Intracellularly In order to achieve the isomerization reaction of galactose into tagatose over the limit of thermodynamic equilibrium, two oxidoreductase reactions for isomerizing galactose into tagatose intracellularly were introduced. The first reaction step was the NADPH-mediated reduction of galactose into galacitol by xylose reductase (XR). XR can reduce galactose into galactitol (11), so XR from Scheffersomyces *stipitis* was introduced into the EJ2g which can accumulate galactose during lactose utilization. When XYL1 coding for XR was overexpressed under the control of a strong promoter (TDH3 promoter) in a multicopy plasmid (pRS42K), the resulting strain (EJ2gX) produced substantial amounts of galactitol during lactose fermentation as designed (FIG. 2). The second reaction step was the NAD+-mediated oxidation of galactitol into tagatose by galactitol 2-dehydrogenase (Gdh). RlGDH from *Rhizobium legumenosarum* (12) was introduced into the galacitol producing strain (EJ2gX) for the conversion of the galactitol into tagatose in engineered yeast. Overexpression of GDH using a strong promoter (TDH3 promoter) in a multi-copy plasmid (pRS42H plasmid) in the EJ2gX strain led to 10 g/L of tagatose production from 50 g/L of lactose under aerobic conditions (FIG. 3). These results indicated that Gdh is functionally expressed in *S. cerevisiae* and can convert galactitol into tagatose in vivo.

Figure 4:
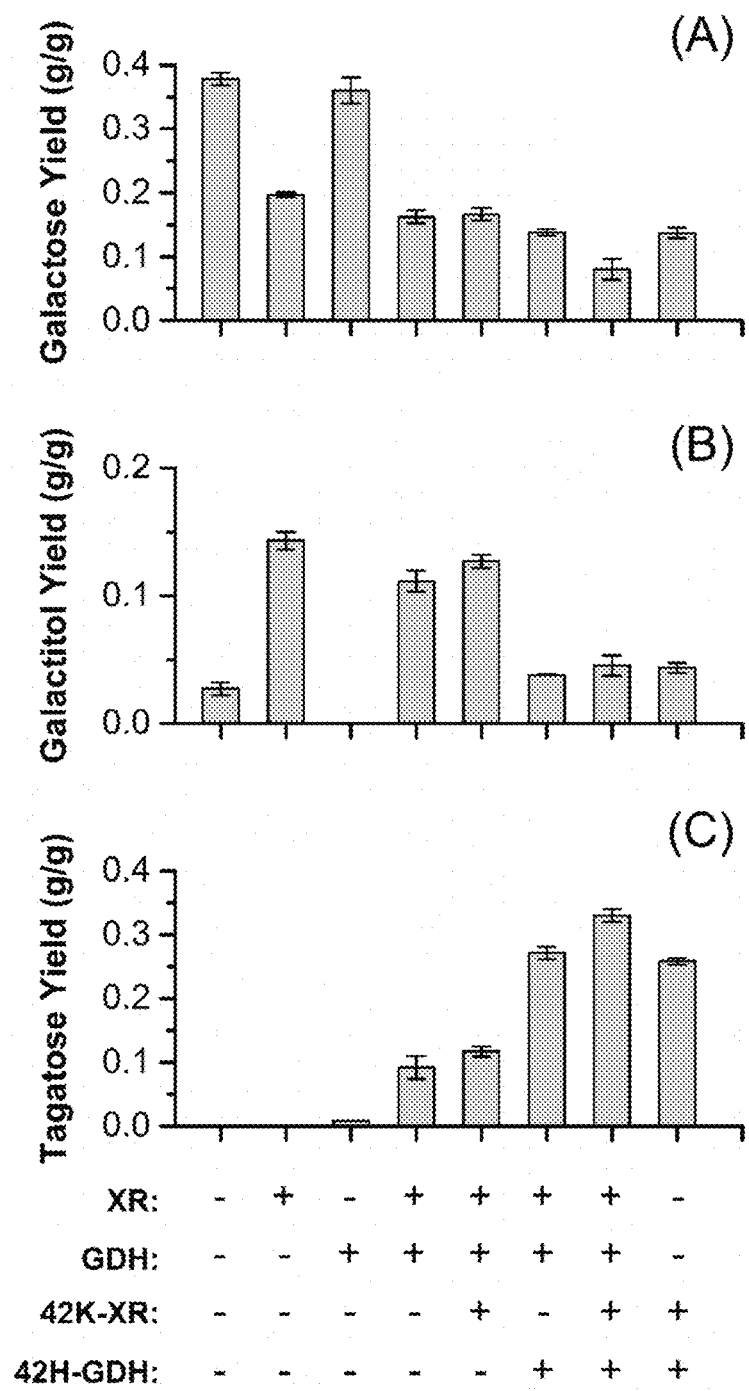
FIG. 4 panels A-C. The production of tagatose under different XR and GDH copy numbers.
Figure 5:
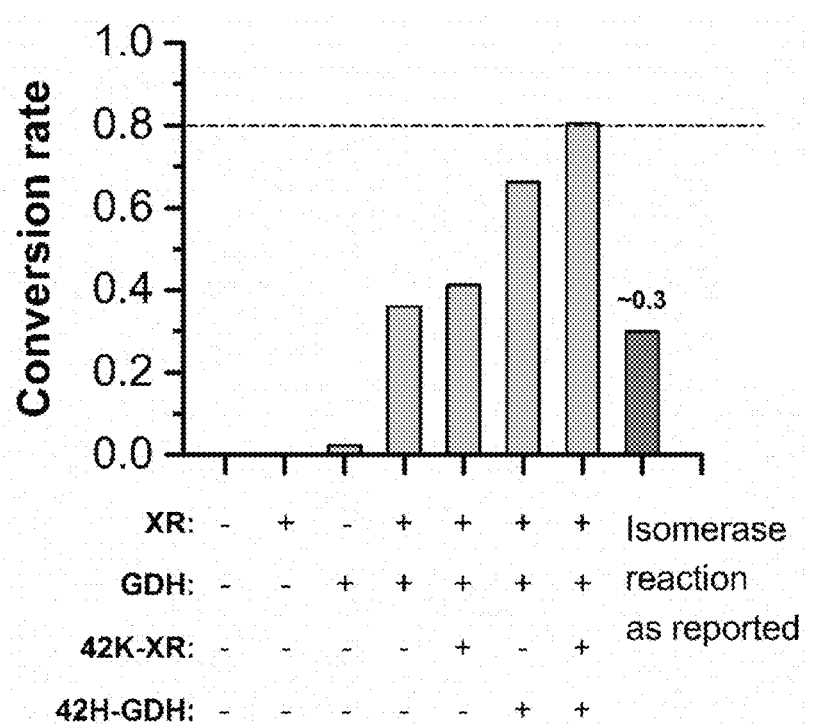
FIG. 5. The galactose-tagatose ratio can reach as high as 80% by using oxidoreductive pathway as compared to 30% through isomerase reaction at 30° C.
Figure 6:
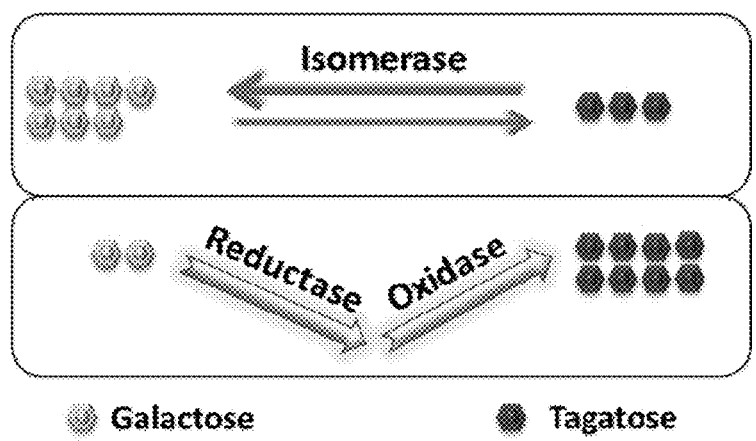
FIG. 6. Schematic of final status after reaction.

Example 3. Optimization of Expression Levels of XR and Gdh for Enhancing Tagatose Production by Engineered Yeast A genetically engineered yeast was able to produce tagatose from lactose directly, the production level of tagatose was only 40% of the theoretical maximum. Expression levels of XR and Gdh were optimized to minimize byproduct (galacitol) and maximize tagatose production. In order to understand the relationships among the production levels of galacitol and tagatose, and the expression levels of XR, and Gdh, three more engineered strains were constructed expressing additional copies of XR and Gdh through Cas9-based genome integration (13, 14). Tagatose production and galacitol accumulation was examined during the conversion of lactose by four engineered yeast strains. Additional overexpression of XR in the prototype strain led to more galactitol production and similar tagatose production whereas additional overexpression of GDH in the prototype strain led to less galactitol production and similar tagatose production as compared to the prototype strain. This result shows that expression levels of XR and GDH is important to control metabolic fluxes toward tagatose production. When both XR and GDH were additionally overexpressed in the prototype strain, the resulting strain produced less galactitol and had more tagatose production (FIG. 4). With simple modifications in the expression levels of XR and GDH, tagatose production from lactose was improved more than 50%.

Isomerase reaction and oxidoreductive reaction are the two parallel pathways developed along biological evolution. The former one is mainly adopted by prokaryotes and the latter one spreads widely in eukaryotes. Isomerase reactions have been well adopted for industrial production of various value-added chemicals through enzyme reaction, because isomerase always functions independently, allowing in vitro enzymatic conversion. However, two fundamental problems exist regarding isomerase-based enzymatic conversion. First, the inherent thermodynamic equilibrium between substrate and product leads to low conversion rate and creates difficulties for downstream products separation and purification. Second, the scale-up cost increases sharply, because the enzyme to be used is in direct proportion to the proposed reaction scale. For example, in rare sugar industry where rare sugars are mainly produced by enzymatic reactions followed by complicated separation process, the production costs are significant and therefore this industry met its waterloo against other sweetener industries.

Unlike the isomerase reaction, the oxidoreductive reaction requires two-step reactions (oxidative reaction and reductive reaction) and co-factors to achieve the same purpose, whereas this seemingly redundant mechanism always well prevents the futile reverse reaction from happening. Therefore, using galactose-tagatose conversion as an example, the oxidoreductive pathway was employed instead of the isomerase pathway, aiming for complete conversion of galactose into tagatose.

To implement oxidoreductive pathway for tagatose production, the in vivo bioconversion instead of in vitro enzymatic conversion is necessary due to the cofactor requirement. This is regarded as an advantage because an efficient self-sustained bioconversion system can significantly lower the scale-up cost. As such, a carbon partition strategy was developed that allows simultaneous cell maintenance and tagatose production. This strategy is not merely limited to the use for this study but can also serve as a general method for other practical use. When consuming disaccharides, the native pathway of one of the monosaccharide moiety can be optionally turned off and reprogrammed towards a target chemical, while leaving the other monosaccharide moiety for cell growth and maintenance.

In this study, lactose was used as sole carbon source. The galactose pathway was shut down to redirect galactose to tagatose through oxidoreductive pathway. In the meantime, the engineered yeast strain consumed glucose as energy source to sustain this cell factory. Because the two monosaccharides were released intracellularly, the glucose repression on galactose uptake was bypassed and thus allowed simultaneous co-utilization of the two monosaccharides. In this cell factory, the lactose to glucose and galactose, and subsequent galactose to tagatose conversion and separation were integrated and self-sustained, which dramatically reduced the processing cost. In other cases, for instance, if our target chemical is easier produced from glucose rather than galactose, we can turn off glucose pathway by disruption of hexose kinases (HXK1 and HXK2) and glucose kinase (GLK1) genes, and then introduce the target oxidoreductive pathway to allow glucose rerouting to the target chemical. In the meantime, the native galactose pathway is left functional for cell maintenance. In reality, other than lactose, quite a few of disaccharides such as sucrose, maltose and cellobiose are also cheap and abundant. Because engineered yeast strains capable of efficient and rapid consumption of these disaccharides have been well developed throughout the yeast community, target chemicals can be produced from these disaccharides as needed through the carbon partition strategy.

In the case of this study, as compared to previous industrial tagatose production, this strategy can lower the production cost at almost every node of the process. First, the majority of galactose is made from enzyme hydrolysis of lactose and followed by the separation of glucose and galactose. Therefore, direct consumption of lactose by an engineered yeast strain can significantly reduce the enzyme cost (β-galactosidase) and separation cost, not to mention that lactose is a rather abundant industrial by-product generated during cheese and Greek yogurt production. Next, the in vivo oxidoreductive conversion of galactose into tagatose eliminated the cost from purified L-arabinose isomerase. This beneficial effect magnifies when reaction scale becomes bigger because unlike direct proportionally increased enzyme cost, the engineered yeast replicates itself continuously regardless of the reaction scale. In the end, most importantly, the oxidoreductive reaction could allow near-complete conversion of galactose into tagatose. Therefore, we are not only able to obtain the maximum value from the substrate, but are also capable of separating products with less cost.

In general, following the presented novel strategy, we can envision the production of most of the chemicals of interest with fairly low cost using engineered yeast through bioconversion, as long as appropriate disaccharide-consuming yeast strain is chosen and oxidoreductive pathway enzymes are available.

Example 4. The Activity of L-Arabinose Isomerase from *Lactobacillus plantarum* in Yeast There are two different pathways existing in the nature, one is oxidoreductive reactions which consist of reduction and oxidation steps and the other is isomerase reaction which converts one molecule from one isoform to another. We showed above that oxidoreduction is working pretty well in yeast and the conversion rate of tagatose is as high as 80%. Below are some data about the activity of L-arabinose isomerase from *Lactobacillus plantarum* (6, 20). The bioconversion yield of D-galactose to D-tagatose by the purified I-AI NC8 after 6 h at 60 degrees C. was 30% (6).

Strains and Media

*Escherichia coli* Top10 was used for the construction and propagation of plasmids. *E. coli* was grown in Luria-Bertani medium (5 g/L yeast extract, 10 g/L tryptone, 10 g/L NaCl, pH 7.0) at 37° C., and ampicillin (100 μg/mL) was added for selection when required. Yeast strains were grown on YP medium (10 g/L yeast extract, 20 g/L peptone) containing 20 g/L glucose at 30° C. Yeast strains transformed with plasmids containing antibiotic markers were propagated on YPD (YP with 20 g/L glucose) plates supplemented with the corresponding antibiotics such as Hygromycin (300 μg/ml) and/or G418 (300 μg/ml).

Plasmids and Strains Construction

The guide RNA plasmid was amplified from gRNA-ura-HYB (14, 15) as template using primer pair Gal1-gU and Gal1-gD (Table 1) carrying 20 bp PAM sequence for GAL1 deletion. Donor DNA was amplified using primers Gal1-Donnor-U and Gal1-Donnor-D. GAL1 was deleted in the EJ2 strain (16) using CRISPR-Cas9 technology as described previously (14). Primers Gal1-CK-U and Gal1-CK-D (Table 1) were used for the confirmation of GAL1 deletion. pGPD-tCYC1 cassette from plasmid p426-pGPD (17) was double digested by SacI and KpnI and ligated with the same enzyme digested pRS42H (18), forming plasmid p42H-pGPD (Table. 1). Plasmid pYS10 (19)) was digested by SacI and XhoI and the pTDH3-XYL1-tTDH3 cassette was ligated with the same enzyme digested pRS42K to construct p42K-XR (Table. 1). The gBlocks gene fragment of GDH was synthesized (IDT Inc, Skokie, Ill.) and blunt-ligated with (15)).

Fermentation and Metabolite Analysis

The lactose fermentation was prepared by inoculating the overnight pre-culture (5 mL of YP medium containing 20 g/L of cellobiose) into 20 mL YPL50 (YP medium containing 50 g/L of lactose) in a 125 mL Erlenmeyer flask with an initial optical density at 600 nm ($OD_{600}$)=1.0 and incubated at 30° C. and 250 rpm. $OD_{600}$ was measured by the spectrophotometer (Biomate 5, Thermo, NY). Lactose, galactose, galactitol, and tagatose concentrations were determined by high performance liquid chromatography (HPLC, Agilent Technologies 1200 Series) equipped with a refractive index detector (RID), using a Rezex™ RCM-Monosaccharide Ca+2 (8%) column (Phenomenex Inc. Torrance, Calif.). The mobile phase is EPure water and was eluted at a flow rate of 0.6 mL/min at 80° C.

Psicose Production

Figure 11:
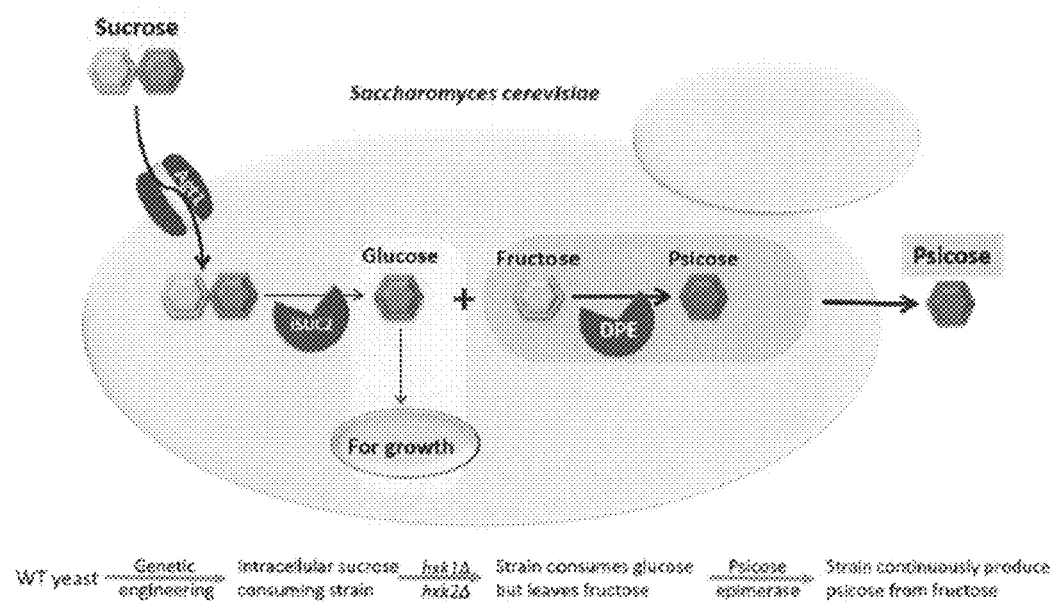
FIG. 11 panels A-C. The schematic diagram of bioconversion of sucrose to psicose (also known as allulose) by engineered yeast. Agt1: alpha-glucoside permease; iSuc2: truncated invertase; Dpe: D-psicose 3-epimerase.
Figure 12:
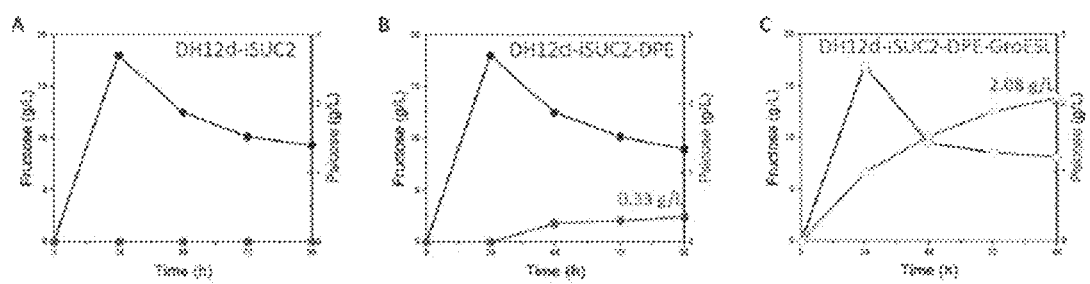
FIG. 12. The bioconversion of fructose from sucrose to psicose by engineered yeast. A: HXK1 and HXK2 deletion and intracellular sucrose hydrolyzation lead to accumulation of fructose; B: the introduction of Dpe converts fructose to psicose; C: chaperon GroESL (i.e., GroES and GroEL) expression enhanced the Dpe enzymatic activity, which is beneficial for psicose production.

As for psicose production from sucrose, a wild type yeast strain was firstly engineered to hydrolyze sucrose inside of the cell by deleting the N-terminal signal sequence of SUC2 encoding sucrose invertase and overexpressing an alpha-glucoside permease Agt1 p (FIG. 11). In order to provide fructose intracellularly for the bioconversion to psicose, HXK1 and HXK2 encoding hexose kinase, which are crucial for fructose utilization, were both deleted. As seen from FIG. 11A, the engineered strain used glucose for metabolism and accumulated high amounts of fructose. Psicose epimerase (DPE) was then introduced to the above strain and psicose was detected (FIG. 11B). Chaperon GroES and GroEL from *E. coli* can help heterologous protein folding in yeast and enhance the enzymatic activity (21). Later, GroES and GroEL was introduced to the strain with DPE, and psicose production was further improved (FIG. 11C).

REFERENCES

1. Lu Y, Levin G V, & Donner T W (2008) Tagatose, a new antidiabetic and obesity control drug. *Diabetes, obesity & metabolism* 10(2): 109-134.
2. Kim P (2004) Current studies on biological tagatose production using I-arabinose isomerase: a review and future perspective. *Appl Microbiol Biot* 65(3):243-249.
3. Leang K, et al. (2004) Novel reactions of I-rhamnose isomerase from *Pseudomonas stutzeri* and its relation with d-xylose isomerase via substrate specificity. *Biochimica et Biophysica Acta (BBA)—General Subjects* 1674(1):68-77.
4. Leang K, et al. (2004) A novel enzymatic approach to the massproduction of L-galactose from L-sorbose. *J Biosci Bioeng* 97(6):383-388.
5. Wanarska M & Kur J (2012) A method for the production of D-tagatose using a recombinant *Pichia pastoris* strain secreting beta-D-galactosidase from *Arthrobacter chlorophenolicus* and a recombinant L-arabinose isomerase from *Arthrobacter* sp. 22c. *Microb Cell Fact* 11:113.
6. Chouayekh H, et al. (2007) Characterization of an I-arabinose isomerase from the *Lactobacillus plantarum* NC8 strain showing pronounced stability at acidic pH. *FEMS Microbiol Lett* 277(2):260-267.
7. Staudigl P, Haltrich D, & Peterbauer C K (2014) L-Arabinose isomerase and D-xylose isomerase from *Lactobacillus reuteri*: characterization, coexpression in the food grade host *Lactobacillus plantarum*, and application in the conversion of D-galactose and D-glucose. *J Agric Food Chem* 62(7): 1617-1624.
8. Cheng L, Mu W, & Jiang B (2010) Thermostable L-arabinose isomerase from *Bacillus stearothermophilus* IAM 11001 for D-tagatose production: gene cloning, purification and characterisation. *J Sci Food Agric* 90(8):1327-1333.
9. Kim B-C, et al. (2002) Cloning, expression and characterization of L-arabinose isomerase from *Thermotoga neapolitana*: bioconversion of D-galactose to D-tagatose using the enzyme. *FEMS Microbiology Letters* 212(1): 121-126.
10. Lim B C, Kim H J, & Oh D K (2007) High production of D-tagatose by the addition of boric acid. *Biotechnol Prog* 23(4):824-828.
11. Seiboth B, Gamauf C, Pail M, Hartl L, & Kubicek C P (2007) The D-xylose reductase of *Hypocrea jecorina* is the major aldose reductase in pentose and D-galactose catabolism and necessary for beta-galactosidase and cellulase induction by lactose. *Mol Microbiol* 66(4):890-900.
12. Jagtap S S, Singh R, Kang Y C, Zhao H, & Lee J K (2014) Cloning and characterization of a galactitol 2-dehydrogenase from *Rhizobium legumenosarum* and its application in D-tagatose production. *Enzyme Microb Technol* 58-59:44-51.
13. DiCarlo J E, et al. (2013) Genome engineering in *Saccharomyces cerevisiae* using CRISPR-Cas systems. *Nucleic Acids Res* 41(7):4336-4343.
14. Zhang G C, et al. (2014) Construction of a quadruple auxotrophic mutant of an industrial polyploid *Saccharomyces cerevisiae* strain by using RNA-guided Cas9 nuclease. *Appl Environ Microbiol* 80(24):7694-7701.
15. Liu J J, et al. (2016) Metabolic Engineering of Probiotic *Saccharomyces boulardii*. *Appl Environ Microbiol* 82(8): 2280-2287.
16. Oh E J, et al. (2016) Gene amplification on demand accelerates cellobiose utilization in engineered *Saccharomyces cerevisiae*. *Appl Environ Microbiol*.
17. Mumberg D, Muller R, & Funk M (1995) Yeast vectors for the controlled expression of heterologous proteins in different genetic backgrounds. *Gene* 156(1):119-122.
18. Taxis C & Knop M (2006) System of centromeric, episomal, and integrative vectors based on drug resistance markers for *Saccharomyces cerevisiae*. *Biotechniques* 40(1):73-78.
19. Jin Y S & Jeffries T W (2003) Changing flux of xylose metabolites by altering expression of xylose reductase and xylitol dehydrogenase in recombinant *Saccharomyces cerevisiae*. *Appl Biochem Biotechnol* 105-108:277-286.
20. Wisselink H W, et al. (2007) Engineering of *Saccharomyces cerevisiae* for efficient anaerobic alcoholic fermentation of L-arabinose. *Appl Environ Microbiol* 73(15): 4881-4891.
21. Xia P F, et al. (2016) GroE chaperonins assisted functional expression of bacterial enzymes in *Saccharomyces cerevisiae*. *Biotechnol Bioeng*.

What is claimed is:

1. A recombinant yeast comprising heterologous polynucleotides encoding a *Neurospora crassa* or *Pichia stipitis* cellodextrin transporter (Cdt-1) polypeptide; a *Neurospora crassa* β-galactosidase (Gh1-1) polypeptide; a *Scheffersomyces stipites* a xylose reductase (XR) polypeptide; and a *Rhizobium leguminosarum* galactitol 2-dehydrogenase (Gdh) polypeptide or an *Escherichia coli, Thermotoga neapolitana, Psedothermotoga thermarum, Bacillus subtilis, Mycobacterium smegmatis, Bacillus licheniformis, Lactobacillus plantarum, Arthrobacter aurescens, Clavibacter michiganensis, Gramella forsetii, Bacteroides thetaiotamicron*, or *Thermotoga neapolitana* L-arabinose isomerase (AraA) polypeptide, wherein any enzyme activity of an endogenous Gal1 polypeptide is attenuated or eliminated.

2. A recombinant yeast for producing tagatose, wherein the recombinant yeast expresses: a) a heterologous *Neurospora crassa* or *Pichia stipitis* cellodextrin transporter (Cdt-1) polypeptide for transport of lactose into the recombinant yeast; b) a heterologous *Neurospora crassa* β-galactosidase (Gh1-1) polypeptide for converting lactose to glucose and galactose; c) a heterologous *Scheffersomyces stipites* xylose reductase (XR) polypeptide for conversion of galactose into galactitol; d) a heterologous *Rhizobium leguminosarum* galactitiol-2-dehydrogenase (Gdh) polypeptide to convert galactitol to tagatose, or a heterologous *Escherichia coli, Thermotoga neapolitana, Psedothermotoga thermarum, Bacillus subtilis, Mycobacterium smegmatis, Bacillus licheniformis, Lactobacillus plantarum, Arthrobacter aurescens, Clavibacter michiganensis, Gramella forsetii, Bacteroides thetaiotamicron*, or *Thermotoga neapolitana* L-arabinose isomerase (AraA) polypeptide to convert L-arabinose to L-ribulose, or both the heterologous Gdh polypeptide and the heterologous AraA polypeptide; and wherein any enzyme activity of an endogenous Gal1 polypeptide is attenuated or eliminated.

3. The recombinant yeast of claim 2, wherein the heterologous Cdt-1 polypeptide has at least 95% sequence identity to SEQ ID NO:5 and has cellodextrin transporter activity, the heterologous Gh1-1 polypeptide has at least 95% sequence identity to SEQ ID NO:6 and has β-galactosidase activity, the heterologous xylose reductase polypeptide has at least 95% sequence identity to SEQ ID NO:7 and has xylose reductase activity, and the heterologous Gdh polypeptide has at least 95% sequence identity to SEQ ID NO:8 and has galactitiol-2-dehydrogenase activity.

4. The recombinant yeast of claim 2, wherein any enzyme activity of an endogenous hexose kinase 1 (Hxk1), an endogenous hexose kinase 2 (Hxk2), or combinations thereof are attenuated or eliminated.

5. The recombinant yeast of claim 2, wherein the Cdt-1 polypeptide is encoded by a polynucleotide as set forth in SEQ ID NO:1, the Gh1-1 polypeptide is encoded by a polynucleotide as set forth in SEQ ID NO:2, the XR polypeptide is encoded by a polynucleotide as set forth in SEQ ID NO:3, and the Gdh polypeptide is encoded by a polynucleotide as set forth in SEQ ID NO:4, SEQ ID NO:30, or SEQ ID NO:31.

6. The recombinant yeast of claim 2, wherein a polynucleotide encoding the Cdt-1 polypeptide has at least 95% sequence identity to SEQ ID NO:1, wherein a polynucleotide encoding the Gh1-1 polypeptide has at least 95% sequence identity to SEQ ID NO:2, wherein a polynucleotide encoding the XR polypeptide has at least 95% sequence identity to SEQ ID NO:3, and wherein a polynucleotide encoding the Gdh polypeptide has at least 95% sequence identity to SEQ ID NO:4, SEQ ID NO:30, or SEQ ID NO:31.

7. The recombinant yeast of claim 2, wherein the Cdt-1 polypeptide has the amino acid sequence set forth in SEQ ID NO:5, the Gh1-1 polypeptide has the amino acid sequence set forth in SEQ ID NO:6, the XR polypeptide has the amino acid sequence set forth in SEQ ID NO:7, and the Gdh polypeptide has the amino acid sequence set forth in SEQ ID NO:8.

8. The recombinant yeast of claim 2, wherein the yeast is selected from Saccharomyceraceae sp., *Saccharomyces cerevisiae, Saccharomyces pastorianus, Saccharomyces beticus, Saccharomyces fermentati, Saccharomyces paradoxus, Saccharomyces uvarum Saccharomyces bay anus;* Schizosaccharomyces sp., *Schizosaccharomyces pombe, Schizosaccharomyces japonicus, Schizosaccharomyces octosporus, Schizosaccharomyces cryophilus,* Torulaspora sp., *Torulaspora delbrueckii,* Kluyveromyces sp., *Kluyveromyces marxianus,* Pichia sp., *Pichia stipitis, Pichia pastoris, Pichia angusta,* Zygosaccharomyces sp., *Zygosaccharomyces bailli,* Brettanomyces sp., *Brettanomyces inter medius, Brettanomyces bruxellensis, Brettanomyces anomalus, Brettanomyces custersianus, Brettanomyces naardenensis, Brettanomyces nanus, Dekkera bruxellensis, Dekkera anomala;* Metschmkowia sp., Issatchenkia sp., *Issatchenkia orientalis,* Kloeckera sp. *Kloeckera apiculate,* Aureobasidium sp., *Aureobasidium pullulans*, and *Corynebacterium glutamicum.*

9. The recombinant yeast of claim 2, wherein the yeast is *Saccharomyces cerevisiae*.

10. A method for producing tagatose comprising culturing the recombinant yeast of claim 2 with a substrate under suitable fermentation conditions to produce the tagatose.

11. The method of claim 10, wherein the substrate comprises lactose.

12. A method of treating acid whey comprising contacting the recombinant yeast of claim 2 with the acid whey under suitable fermentation conditions such that the acid whey is treated.

13. The method of claim 11, wherein the substrate contains 20% or more lactose.

14. The method of claim 12, wherein the acid whey contains 20% or more lactose.

15. The method of claim 12, wherein treatment reduces the amount of lactose, galactose, or both lactose and galactose in the acid whey by 30% or more than the acid whey contained prior to the treatment.

16. The method of claim 12, wherein the treatment reduces acidity of the acid whey by 30% or more as compared to the acidity prior to the treatment.

* * * * *

```
                        SEQUENCE LISTING

<160> NUMBER OF SEQ ID NOS: 32

<210> SEQ ID NO 1
<211> LENGTH: 1740
<212> TYPE: DNA
<213> ORGANISM: Neurospora crassa

<400> SEQUENCE: 1
atgtcgtctc acggctccca tgacggggcc agcaccgaga agcatcttgc tactcatgac      60
```

```
attgcgccca cccacgacgc catcaagata gtgcccaagg gccatggcca gacagccaca      120
aagcccggtg cccaagagaa ggaggtccgc aacgccgccc tatttgcggc catcaaggag      180
tccaatatca agccctggag caaggagtcc atccacctct atttcgccat cttcgtcgcc      240
ttttgttgtg catgcgccaa cggttacgat ggttcactca tgaccggaat catcgctatg      300
gacaagttcc agaaccaatt ccacactggt gacactggtc ctaaagtctc tgtcatcttt      360
tctctctata ccgttggtgc catggttgga gctcccttcg ctgctatcct ctctgatcgt      420
tttggccgta agaagggcat gttcatcggt ggtatcttta tcattgtcgg ctccattatt      480
gttgctagct cctccaagct cgctcagttt gtcgttggcc gcttcgttct tggcctcggt      540
atcgccatca tgaccgttgc tgccccggcc tactccatcg aaatcgcccc tcctcactgg      600
cgcggccgct gcactggctt ctacaactgc ggttggttcg gaggttcgat tcctgccgcc      660
tgcatcacct atggctgcta cttcattaag agcaactggt catggcgtat ccccttgatc      720
cttcaggctt tcacgtgcct tatcgtcatg tcctccgtct tcttcctccc agaatcccct      780
cgcttcctat ttgccaacgg ccgcgacgct gaggctgttg cctttcttgt caagtatcac      840
ggcaacggcg atcccaattc caagctggtg ttgctcgaga ctgaggagat gagggacggt      900
atcaggaccg acggtgtcga caaggtctgg tgggattacc gcccgctctt catgacccac      960 agcgccgct ggcgcatggc ccaggtgctc atgatctcca tctttggcca gttctccggc     1020
aacggtctcg gttacttcaa taccgtcatc ttcaagaaca ttggtgtcac cagcacctcc     1080
caacagctcg cctacaacat cctcaactcc gtcatctccg ctatcggtgc cttgaccgcc     1140
gtctccatga ctgatcgtat gccccgccgc gcggtgctca ttatcggtac cttcatgtgc     1200
gccgctgctc ttgccaccaa ctcgggtctt tcggctactc tcgacaagca gactcaaaga     1260
ggcacgcaaa tcaacctgaa ccagggtatg aacgagcagg atgccaagga caacgcctac     1320
ctccacgtcg acagcaacta cgccaagggt gccctggccg cttacttcct cttcaacgtc     1380
atcttctcct tcacctacac tcccctccag ggtgttattc ccaccgaggc tctcgagacc     1440
accatccgtg gcaagggtct tgccctttcc ggcttcattg tcaacgccat gggcttcatc     1500
aaccagttcg ctggccccat cgctctccac aacattggct acaagtacat ctttgtcttt     1560
gtcggctggg atcttatcga gaccgtcgct tggtacttct ttggtgtcga atcccaaggc     1620
cgtaccctcg agcagctcga atgggtctac gaccagccca accccgtcaa ggcctcccta     1680
aaagtcgaaa aggtcgtcgt ccaggccgac ggccatgtgt ccgaagctat cgttgcttag     1740
```

<210> SEQ ID NO 2
<211> LENGTH: 1430
<212> TYPE: DNA
<213> ORGANISM: Neurospora crassa

<400> SEQUENCE: 2

```
atgtctcttc ctaaggattt cctctggggc ttcgctactg cggcctatca gattgagggt       60
gctatccacg ccgacggccg tggcccctct atctgggata ctttctgcaa cattcccggt      120
aaaatcgccg acggcagctc tggtgccgtc gcctgcgact cttacaaccg caccaaggag      180
gacattgacc tcctcaagtc tctcggcgcc accgcctacc gcttctccat ctcctggtct      240
cgcatcatcc ccgttggtgg tcgcaacgac cccatcaacc agaagggcat cgaccactat      300
gtcaagtttg tcgatgacct gctcgaggct ggtattaccc cctttatcac cctcttccac      360
tgggatcttc ccgatggtct cgacaagcgc tacggcggtc ttctgaaccg tgaagagttc      420
```

-continued

```
cccctcgact ttgagcacta cgcccgcact atgttcaagg ccattcccaa gtgcaagcat      480
ggatcacctt caacgagccc tggtgcagct ccatcctcgg ctacaactcg ggctactttg      540
cccctggcca cacctccgac cgtaccaagt cacccgttgg tgacagcgct cgcgagccct      600
ggatcgtcgg ccataacctg ctcatcgctc acgggcgtgc cgtcaaggtg taccgagaag      660
acttcaagcc cacgcagggc ggcgagatcg gtatcacctt gaacggcgac gccactcttc      720
cctgggatcc agaggacccc ttggacgtcg aggcgtgcga ccgcaagatt gagttcgcca      780
tcagctggtt cgcagacccc atctactttg aaagtaccc cgactcgatg cgcaaacagc      840
tcggtgaccg gctgcccgag tttacgcccg aggaggtggc gcttgtcaag ggttccaacg      900
acttctacgg catgaaccac tacacagcca actacatcaa gcacaagaag ggcgtccctc      960
ccgaggacga cttcctcggc aacctcgaga cgctcttcta caacaagaag gtaactgca     1020 tcgggcccga gacccagtcg ttctggctcc ggccgcacgc ccagggcttc cgcgacctgc     1080
tcaactggct cagcaagcgc tacgatacc ccaagatcta cgtgaccgag aacgggacca     1140
gtctcaaggg cgagaacgcc atgccgctca agcaaattgt cgaggacgac ttccgcgtca     1200
agtacttcaa cgactacgtc aacgccatgg ccaaggcgca tagcgaggac ggcgtcaacg     1260
tcaagggata tcttgcctgg agcttgatgg acaactttga gtgggccgag ggctatgaga     1320
cgcggttcgg cgttacctat gtcgactatg agaacgacca aagaggtac cccaagaaga     1380 gcgccaagag cttgaagccg ctctttgact ctttgatcaa gaaggactaa                1430
```

<210> SEQ ID NO 3
<211> LENGTH: 957
<212> TYPE: DNA
<213> ORGANISM: Scheffersomyces stipites

<400> SEQUENCE: 3

```
atgccttcta ttaagttgaa ctctggttac gacatgccag ccgtcggttt cggctgttgg      60
aaagtcgacg tcgacacctg ttctgaacag atctaccgtg ctatcaagac cggttacaga     120
ttgttcgacg gtgccgaaga ttacgccaac gaaaagttag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca gaaccctttc tgacttgcaa     300
gttgactacg ttgacttgtt cttgatccac ttcccagtca ccttcaagtt cgttccatta     360
gaagaaaagt acccaccagg attctactgt ggtaagggtg acaacttcga ctacgaagat     420
gttccaattt tagagacctg gaaggctctt gaaaagttgg tcaaggccgg taagatcaga     480
tctatcggtg tttctaactt cccaggtgct tgctcttgg acttgttgag aggtgctacc     540
atcaagccat ctgtcttgca agttgaacac caccccatact gcaacaacc aagattgatc     600 gaattcgctc aatcccgtgg tattgctgtc accgcttact cttcgttcgg tcctcaatct     660
ttcgttgaat tgaaccaagg tagagctttg aacacttctc cattgttcga gaacgaaact     720
atcaaggcta tcgctgctaa gcacggtaag tctccagctc aagtcttgtt gagatggtct     780
tcccaaagag gcattgccat cattccaaag tccaacactg tcccaagatt gttggaaaac     840
aaggacgtca acagcttcga cttggacgaa caagatttcg ctgacattgc caagttggac     900
atcaacttga gattcaacga cccatgggac tgggacaaga ttcctatctt cgtctaa       957
```

<210> SEQ ID NO 4
<211> LENGTH: 774
<212> TYPE: DNA
<213> ORGANISM: Artificial Sequence

```
<220> FEATURE:
<223> OTHER INFORMATION: Yeast-codon optimized nucleotide sequence for
      GDH

<400> SEQUENCE: 4
atgtcttatc agcaaaagtt tcgtttagat ggtgaaaggg ctgtggttac aggaggcggc      60
agagcaattg gtctttgttg tactgaggct ttggctgaag caggtgccgc tgttgttgta     120
atagagaggt ctgaagctga cgctgaacaa gctctagcac ttagaaacag aggatacgat     180
gttgaagtca gagttggtga tgttactgat gcggcaagga tggacgctat agctactgaa     240
ttagctgacg gtggtcgtcc agcaacaatc ctggttaaca acgctggtat cggtcagagt     300
gggattcctg cgcaagatct aacagacgca gattggttga gaatgatgga tgttaatctg     360
aatggtgttt tttggtgttc ccgtgctttc ggaagaagta tgatttccat gaaacgtggt     420
gcgattgtca acttagggtc aatgtcaggt acgatctgca acagaccaca accacaaact     480
gcatataacg taagtaaggc tgcggtccat catttgacca gatccttagc tgctgagtgg     540
gcacatcatg aatcagggt gaatgctgtc gctcctacat acatcgagac ccctatggtg     600
gtcgctgttg aagcaaatag ggaaaggatt cctttatggt tagccgatac tccaatggca     660
cgtatgggca cacccgaaga ggtagcctcc gcggtactat ttctggcatc aggtgctgca     720
tctttaatga cgggagccat agttaatgtt gacgcaggct tcacatgttg gtaa           774

<210> SEQ ID NO 5
<211> LENGTH: 579
<212> TYPE: PRT
<213> ORGANISM: Neurospora crassa

<400> SEQUENCE: 5

Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

Phe Cys Cys Ala Cys Ala Asn Gly Tyr Asp Gly Ser Leu Met Thr Gly
                85                  90                  95

Ile Ile Ala Met Asp Lys Phe Gln Asn Gln Phe His Thr Gly Asp Thr
            100                 105                 110

Gly Pro Lys Val Ser Val Ile Phe Ser Leu Tyr Thr Val Gly Ala Met
        115                 120                 125

Val Gly Ala Pro Phe Ala Ala Ile Leu Ser Asp Arg Phe Gly Arg Lys
    130                 135                 140

Lys Gly Met Phe Ile Gly Gly Ile Phe Ile Val Gly Ser Ile Ile
145                 150                 155                 160

Val Ala Ser Ser Ser Lys Leu Ala Gln Phe Val Val Gly Arg Phe Val
                165                 170                 175

Leu Gly Leu Gly Ile Ala Ile Met Thr Val Ala Ala Pro Ala Tyr Ser
            180                 185                 190

Ile Glu Ile Ala Pro Pro His Trp Arg Gly Arg Cys Thr Gly Phe Tyr
        195                 200                 205
```

Asn Cys Gly Trp Phe Gly Gly Ser Ile Pro Ala Ala Cys Ile Thr Tyr
210                 215                 220

Gly Cys Tyr Phe Ile Lys Ser Asn Trp Ser Trp Arg Ile Pro Leu Ile
225                 230                 235                 240

Leu Gln Ala Phe Thr Cys Leu Ile Val Met Ser Ser Val Phe Leu
        245                 250                 255

Pro Glu Ser Pro Arg Phe Leu Phe Ala Asn Gly Arg Asp Ala Glu Ala
        260                 265                 270

Val Ala Phe Leu Val Lys Tyr His Gly Asn Gly Asp Pro Asn Ser Lys
            275                 280                 285

Leu Val Leu Leu Glu Thr Glu Met Arg Asp Gly Ile Arg Thr Asp
290                 295                 300

Gly Val Asp Lys Val Trp Trp Asp Tyr Arg Pro Leu Phe Met Thr His
305                 310                 315                 320

Ser Gly Arg Trp Arg Met Ala Gln Val Leu Met Ile Ser Ile Phe Gly
                325                 330                 335

Gln Phe Ser Gly Asn Gly Leu Gly Tyr Phe Asn Thr Val Ile Phe Lys
                340                 345                 350

Asn Ile Gly Val Thr Ser Thr Ser Gln Gln Leu Ala Tyr Asn Ile Leu
            355                 360                 365

Asn Ser Val Ile Ser Ala Ile Gly Ala Leu Thr Ala Val Ser Met Thr
370                 375                 380

Asp Arg Met Pro Arg Arg Ala Val Leu Ile Ile Gly Thr Phe Met Cys
385                 390                 395                 400

Ala Ala Ala Leu Ala Thr Asn Ser Gly Leu Ser Ala Thr Leu Asp Lys
                405                 410                 415

Gln Thr Gln Arg Gly Thr Gln Ile Asn Leu Asn Gln Gly Met Asn Glu
                420                 425                 430

Gln Asp Ala Lys Asp Asn Ala Tyr Leu His Val Asp Ser Asn Tyr Ala
            435                 440                 445

Lys Gly Ala Leu Ala Ala Tyr Phe Leu Phe Asn Val Ile Phe Ser Phe
        450                 455                 460

Thr Tyr Thr Pro Leu Gln Gly Val Ile Pro Thr Glu Ala Leu Glu Thr
465                 470                 475                 480

Thr Ile Arg Gly Lys Gly Leu Ala Leu Ser Gly Phe Ile Val Asn Ala
                485                 490                 495

Met Gly Phe Ile Asn Gln Phe Ala Gly Pro Ile Ala Leu His Asn Ile
                500                 505                 510

Gly Tyr Lys Tyr Ile Phe Val Phe Val Gly Trp Asp Leu Ile Glu Thr
        515                 520                 525

Val Ala Trp Tyr Phe Phe Gly Val Glu Ser Gln Gly Arg Thr Leu Glu
530                 535                 540

Gln Leu Glu Trp Val Tyr Asp Gln Pro Asn Pro Val Lys Ala Ser Leu
545                 550                 555                 560

Lys Val Glu Lys Val Val Val Gln Ala Asp Gly His Val Ser Glu Ala
                565                 570                 575

Ile Val Ala

<210> SEQ ID NO 6
<211> LENGTH: 476
<212> TYPE: PRT
<213> ORGANISM: Neurospora crassa

<400> SEQUENCE: 6

-continued

```
Met Ser Leu Pro Lys Asp Phe Leu Trp Gly Phe Ala Thr Ala Ala Tyr
1               5                   10                  15

Gln Ile Glu Gly Ala Ile His Ala Asp Gly Arg Gly Pro Ser Ile Trp
            20                  25                  30

Asp Thr Phe Cys Asn Ile Pro Gly Lys Ile Ala Asp Gly Ser Ser Gly
            35                  40                  45

Ala Val Ala Cys Asp Ser Tyr Asn Arg Thr Lys Glu Asp Ile Asp Leu
        50                  55                  60

Leu Lys Ser Leu Gly Ala Thr Ala Tyr Arg Phe Ser Ile Ser Trp Ser
65                  70                  75                  80

Arg Ile Ile Pro Val Gly Gly Arg Asn Asp Pro Ile Asn Gln Lys Gly
                    85                  90                  95

Ile Asp His Tyr Val Lys Phe Val Asp Asp Leu Leu Glu Ala Gly Ile
                100                 105                 110

Thr Pro Phe Ile Thr Leu Phe His Trp Asp Leu Pro Asp Gly Leu Asp
                115                 120                 125

Lys Arg Tyr Gly Gly Leu Leu Asn Arg Glu Glu Phe Pro Leu Asp Phe
            130                 135                 140

Glu His Tyr Ala Arg Thr Met Phe Lys Ala Ile Pro Lys Cys Lys His
145                 150                 155                 160

Trp Ile Thr Phe Asn Glu Pro Trp Cys Ser Ser Ile Leu Gly Tyr Asn
                    165                 170                 175

Ser Gly Tyr Phe Ala Pro Gly His Thr Ser Asp Arg Thr Lys Ser Pro
                180                 185                 190

Val Gly Asp Ser Ala Arg Glu Pro Trp Ile Val Gly His Asn Leu Leu
            195                 200                 205

Ile Ala His Gly Arg Ala Val Lys Val Tyr Arg Glu Asp Phe Lys Pro
210                 215                 220

Thr Gln Gly Gly Glu Ile Gly Ile Thr Leu Asn Gly Asp Ala Thr Leu
225                 230                 235                 240

Pro Trp Asp Pro Glu Asp Pro Leu Asp Val Glu Ala Cys Asp Arg Lys
                    245                 250                 255

Ile Glu Phe Ala Ile Ser Trp Phe Ala Asp Pro Ile Tyr Phe Gly Lys
                260                 265                 270

Tyr Pro Asp Ser Met Arg Lys Gln Leu Gly Asp Arg Leu Pro Glu Phe
            275                 280                 285

Thr Pro Glu Glu Val Ala Leu Val Lys Gly Ser Asn Asp Phe Tyr Gly
        290                 295                 300

Met Asn His Tyr Thr Ala Asn Tyr Ile Lys His Lys Lys Gly Val Pro
305                 310                 315                 320

Pro Glu Asp Asp Phe Leu Gly Asn Leu Glu Thr Leu Phe Tyr Asn Lys
                    325                 330                 335

Lys Gly Asn Cys Ile Gly Pro Glu Thr Gln Ser Phe Trp Leu Arg Pro
                340                 345                 350

His Ala Gln Gly Phe Arg Asp Leu Leu Asn Trp Leu Ser Lys Arg Tyr
            355                 360                 365

Gly Tyr Pro Lys Ile Tyr Val Thr Glu Asn Gly Thr Ser Leu Lys Gly
        370                 375                 380

Glu Asn Ala Met Pro Leu Lys Gln Ile Val Glu Asp Asp Phe Arg Val
385                 390                 395                 400

Lys Tyr Phe Asn Asp Tyr Val Asn Ala Met Ala Lys Ala His Ser Glu
                    405                 410                 415

Asp Gly Val Asn Val Lys Gly Tyr Leu Ala Trp Ser Leu Met Asp Asn
```

```
            420             425             430
Phe Glu Trp Ala Glu Gly Tyr Glu Thr Arg Phe Gly Val Thr Tyr Val
        435             440             445

Asp Tyr Glu Asn Asp Gln Lys Arg Tyr Pro Lys Lys Ser Ala Lys Ser
    450             455             460

Leu Lys Pro Leu Phe Asp Ser Leu Ile Lys Lys Asp
465             470             475

<210> SEQ ID NO 7
<211> LENGTH: 318
<212> TYPE: PRT
<213> ORGANISM: Scheffersomyces stipites

<400> SEQUENCE: 7

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 8
<211> LENGTH: 257
<212> TYPE: PRT
<213> ORGANISM: Rhizobium leguminosarum

<400> SEQUENCE: 8

Met Ser Tyr Gln Gln Lys Phe Arg Leu Asp Gly Glu Arg Ala Val Val
1               5                   10                  15

Thr Gly Gly Gly Arg Ala Ile Gly Leu Cys Cys Thr Glu Ala Leu Ala
            20                  25                  30

Glu Ala Gly Ala Ala Val Val Val Ile Glu Arg Ser Glu Ala Asp Ala
        35                  40                  45

Glu Gln Ala Leu Ala Leu Arg Asn Arg Gly Tyr Asp Val Glu Val Arg
    50                  55                  60

Val Gly Asp Val Thr Asp Ala Ala Arg Met Asp Ala Ile Ala Thr Glu
65                  70                  75                  80

Leu Ala Asp Gly Gly Arg Pro Ala Thr Ile Leu Val Asn Asn Ala Gly
                85                  90                  95

Ile Gly Gln Ser Gly Ile Pro Ala Gln Asp Leu Thr Asp Ala Asp Trp
            100                 105                 110

Leu Arg Met Met Asp Val Asn Leu Asn Gly Val Phe Trp Cys Ser Arg
        115                 120                 125

Ala Phe Gly Arg Ser Met Ile Ser Met Lys Arg Gly Ala Ile Val Asn
    130                 135                 140

Leu Gly Ser Met Ser Gly Thr Ile Cys Asn Arg Pro Gln Pro Gln Thr
145                 150                 155                 160

Ala Tyr Asn Val Ser Lys Ala Ala Val His His Leu Thr Arg Ser Leu
                165                 170                 175

Ala Ala Glu Trp Ala His His Gly Ile Arg Val Asn Ala Val Ala Pro
            180                 185                 190

Thr Tyr Ile Glu Thr Pro Met Val Val Ala Val Glu Ala Asn Arg Glu
        195                 200                 205

Arg Ile Pro Leu Trp Leu Ala Asp Thr Pro Met Ala Arg Met Gly Thr
    210                 215                 220

Pro Glu Glu Val Ala Ser Ala Val Leu Phe Leu Ala Ser Gly Ala Ala
225                 230                 235                 240

Ser Leu Met Thr Gly Ala Ile Val Asn Val Asp Ala Gly Phe Thr Cys
                245                 250                 255

Trp

<210> SEQ ID NO 9
<211> LENGTH: 1851
<212> TYPE: DNA
<213> ORGANISM: Saccharomyces cerevisiae

<400> SEQUENCE: 9

| | | |
|---|---|---|
| atgaaaaata tcatttcatt ggtaagcaag aagaaggctg cctcaaaaaa tgaggataaa | 60 |
| aacatttctg agtcttcaag agatattgta aaccaacagg aggttttcaa tactgaagat | 120 |
| tttgaagaag ggaaaaagga tagtgccttt gagctagacc acttagagtt caccaccaat | 180 |
| tcagcccagt taggagattc tgacgaagat aacgagaatg tgattaatga gatgaacgct | 240 |
| actgatgatg caaatgaagc taacagcgag gaaaaaagca tgactttgaa gcaggcgttg | 300 |
| ctaaatatc caaaagcagc cctgtggtcc atattagtgt ctactaccct ggttatggaa | 360 |
| ggttatgata ccgcactact gagcgcactg tatgccctgc cagttttca gagaaaattc | 420 |

```
ggtactttga acggggaggg ttcttacgaa attacttccc aatggcagat tggtttaaac    480
atgtgtgtcc tttgtggtga gatgattggt ttgcaaatca cgactatat ggttgaattt    540
atggggaatc gttatacgat gattacagca cttggtttgt taactgctta tatctttatc   600
ctctactact gtaaaagttt agctatgatt gctgtgggac aaattctctc agctatacca   660
tggggttgtt ccaaagtttt ggctgttact tatgcttcgg aagtttgccc tttagcatta   720
agatattaca tgaccagtta ctccaacatt tgttggttat ttggtcaaat cttcgcctct   780
ggtattatga aaaactcaca agagaattta gggaactccg acttgggcta taaattgcca   840
tttgctttac aatggatttg gcctgctcct ttaatgatcg gtatcttttt cgctcctgag   900
tcgccctggt ggttggtgag aaaggatagg gtcgctgagg caagaaaatc tttaagcaga   960
attttgagtg gtaaaggcgc cgagaaggac attcaagttg atcttacttt aaagcagatt  1020
gaattgacta ttgaaaaaga aagactttta gcatctaaat caggatcatt ctttaattgt  1080
ttcaagggag ttaatggaag aagaacgaga cttgcatgtt taacttgggt agctcaaaat  1140
agtagcggtg ccgttttact tggttactcg acatattttt ttgaaagagc aggtatggcc  1200
accgacaagg cgtttacttt ttctctaatt cagtactgtc ttgggttagc gggtacactt  1260
tgctcctggg taatatctgg ccgtgttggt agatggacaa tactgaccta tggtcttgca  1320
tttcaaatgg tctgcttatt tattattggt ggaatgggtt ttggttctgg aagcagcgct  1380
agtaatggtg ccggtggttt attgctggct ttatcattct tttacaatgc tggtatcggt  1440
gcagttgttt actgtatcgt tgctgaaatt ccatcagcgg agttgagaac taagactata  1500
gtgctggccc gtatttgcta caatctcatg ccgttatta acgctatatt aacgccctat   1560
atgctaaacg tgagcgattg gaactggggt gccaaaactg gtctatactg gggtggtttc  1620
acagcagtca ctttagcttg ggtcatcatc gatctgcctg agacaactgg tagaaccttc  1680
agtgaaatta tgaacttttt caaccaaggg gttcctgcca gaaaatttgc atctactgtg  1740
gttgatccat tcggaaaggg gaaaaactca acatgattcgc tagctgatga gagtatcagt  1800
cagtcctcaa gcataaaaca gcgagaatta aatgcagctg ataaatgtta a           1851
```

<210> SEQ ID NO 10
<211> LENGTH: 870
<212> TYPE: DNA
<213> ORGANISM: Agrobacterium tumefaciens

<400> SEQUENCE: 10

```
atgaaacacg gcatctatta ttcctactgg gaacatgagt ggagcgccaa gttcggtccc    60
tatatcgaga aggtcgccaa gctcggtttc gacatcatcg aagtcgccgc ccaccatatc   120
aacgaataca gcgacgccga actcgcgacc atcaggaaga gcgcgaagga taacggcatc   180
atcctcaccg ccggcatcgg tccgtcgaaa accaagaacc tgtcgtcgga agatgctgcg   240
gtgcgtgcgg ccggcaaggc gttctttgaa agaacccttt cgaacgtcgc caagctcgat   300
atccacacca tcggcggcgc attgcattcc tattggccaa tcgattattc gcagcccgtc   360
gacaaggcag gcgattatgc gcgcggcgtc gagggtatca acggcattgc cgatttcgcc   420
aatgatctcg gcatcaacct gtgcatcgaa gtcctcaacc gctttgaaaa ccacgtcctc   480
aacacggcgg cggaaggcgt cgcttttgtg aaggatgtcg gcaagaacaa tgtgaaagtc   540
atgctggata ccttccacat gaacatcgag gaagacagtt cggtgacgc catccgcacg   600
gccggcccgc ttctggggca cttccatacc ggtgaaagca atcgccgcgt accgggcaag   660
```

-continued

```
ggcagaatgc cgtggcacga atcggcctt gcgctgcgtg atatcaacta caccggcgcg      720
gtaatcatgg agcctttcgt caagacaggc ggcaccatcg gctcggatat caaggtgtgg     780
cgcgacctga gcggtggcgc cgacatcgcg aaaatggatg aagatgcccg caatgcgctg     840
gcattctccc gtttcgtcct tggcggctga                                      870
```

<210> SEQ ID NO 11
<211> LENGTH: 600
<212> TYPE: PRT
<213> ORGANISM: Saccharomyces cerevisiae

<400> SEQUENCE: 11

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Lys Ser Leu Ser Arg
305                 310                 315                 320

Ile Leu Ser Gly Lys Gly Ala Lys Asp Ile Gln Val Asp Leu Thr
                325                 330                 335
```

```
Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ser Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Val Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser
        595                 600

<210> SEQ ID NO 12
<211> LENGTH: 289
<212> TYPE: PRT
<213> ORGANISM: Agrobacterium tumefaciens

<400> SEQUENCE: 12

Met Lys His Gly Ile Tyr Tyr Ser Tyr Trp Glu His Glu Trp Ser Ala
1               5                   10                  15

Lys Phe Gly Pro Tyr Ile Glu Lys Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Leu Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110
```

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 13
<211> LENGTH: 97
<212> TYPE: PRT
<213> ORGANISM: Escherichia coli

<400> SEQUENCE: 13

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 14
<211> LENGTH: 294
<212> TYPE: DNA
<213> ORGANISM: Escherichia coli

<400> SEQUENCE: 14
atgaatattc gtccattgca tgatcgcgtg atcgtcaagc gtaaagaagt tgaaactaaa       60
tctgctggcg gcatcgttct gaccggctct gcagcggcta atccacccg cggcgaagtg       120 ctggctgtcg gcaatggccg tatccttgaa aatggcgaag tgaagccgct ggatgtgaaa       180
gttggcgaca tcgttatttt caacgatggc tacggtgtga atctgagaa gatcgacaat       240

```
gaagaagtgt tgatcatgtc cgaaagcgac attctggcaa ttgttgaagc gtaa          294
```

<210> SEQ ID NO 15
<211> LENGTH: 548
<212> TYPE: PRT
<213> ORGANISM: Escherichia coli

<400> SEQUENCE: 15

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365
```

```
Val Ala Lys Leu Ala Gly Gly Val Ala Val Ile Lys Val Gly Ala Ala
        370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545
```

<210> SEQ ID NO 16
<211> LENGTH: 1647
<212> TYPE: DNA
<213> ORGANISM: Escherichia coli

<400> SEQUENCE: 16

```
atggcagcta aagacgtaaa attcggtaac gacgctcgtg tgaaaatgct gcgcggcgta      60
aacgtactgg cagatgcagt gaaagttacc ctcggtccaa aaggccgtaa cgtagttctg     120
gataaatctt tcggtgcacc gaccatcacc aaagatggtg tttccgttgc tcgtgaaatc     180
gaactggaag acaagttcga aaatatgggt gcgcagatgg tgaaagaagt tgcctctaaa     240
gcaaacgacg ctgcaggcga cggtaccacc actgcaaccg tactggctca ggctatcatc     300
actgaaggtc tgaaagctgt tgctgcgggc atgaacccga tggacctgaa acgtggtatc     360
gacaaagcgg ttaccgctgc agttgaagaa ctgaaagcgc tgtccgtacc atgctctgac     420
tctaaagcga ttgctcaggt tggtaccatc tccgctaact ccgacgaaac cgtaggtaaa     480
ctgatcgctg aagcgatgga caaagtcggt aaagaaggcg ttatcaccgt tgaagacggt     540
accggtctgc aggacgaact ggacgtggtt gaaggtatgc agttcgaccg tggctacctg     600
tctccttact tcatcaacaa gccggaaact ggcgcagtag aactgaaaag cccgttcatc     660
ctgctggctg acaagaaaat ctccaacatc gcgaaatgc tgccggttct ggaagctgtt     720
gccaaagcag caaaccgct gctgatcatc gctgaagatg tagaaggcga agcgctggca     780
actctggttt taacaccat gcgtggcatc gtgaaagtcg ctgcgttaa gcaccgggc      840 ttcggcgatc gtcgtaaagc tatgctgcag gatatcgcaa ccctgactgg cggtaccgtg     900
atctctgaag atcggtat ggagctggaa aaagcaaccc tggaagacct gggtcaggct     960
aaacgtgttg tgatcaacaa agacaccacc actatcatcg atggcgtggg tgaagaagct    1020
```

```
gcaatccagg gccgtgttgc tcagatccgt cagcagattg aagaagcaac ttctgactac   1080
gaccgtgaaa aactgcagga acgcgtagcg aaactggcag gcggcgttgc agttatcaaa   1140
gtgggtgctg ctaccgaagt tgaaatgaaa gagaaaaaag cacgcgttga agatgccctg   1200
cacgcgaccc gtgctgcggt agaagaaggc gtggttgctg gtggtggtgt tgcgctgatc   1260
cgcgtagcgt ctaaactggc tgacctgcgt ggtcagaacg aagaccagaa cgtgggtatc   1320
aaagttgcac tgcgtgcaat ggaagctccg ctgcgtcaga tcgtattgaa ctgcggcgaa   1380
gaaccgtctg ttgttgctaa caccgttaaa ggcggcgacg gcaactacgg ttacaacgca   1440
gcaaccgaag aatacggcaa catgatcgac atgggtatcc tggatccaac caaagtaact   1500
cgttctgctc tgcagtacgc agcttctgtg gctggcctga tgatcaccac cgaatgcatg   1560
gttaccgacc tgccgaaaaa cgatgcagct gacttaggcg ctgctggcgg tatgggcggc   1620
atgggtggca tgggcggcat gatgtaa                                      1647

<210> SEQ ID NO 17
<211> LENGTH: 1458
<212> TYPE: DNA
<213> ORGANISM: Saccharomyces cerevisiae

<400> SEQUENCE: 17
atggttcatt taggtccaaa gaaaccacag gctagaaagg gttccatggc tgatgtgccc     60
aaggaattga tggatgaaat tcatcagttg gaagatatgt ttacagttga cagcgagacc    120
ttgagaaagg ttgttaagca ctttatcgac gaattgaata aaggtttgac aaagaaggga    180
ggtaacattc caatgattcc cggttgggtc atggaattcc caacaggtaa agaatctggt    240
aactatttgg ccattgattt gggtggtact aacttaagag tcgtgttggt caagttgagc    300
ggtaaccata cctttgacac cactcaatcc aagtataaac taccacatga catgagaacc    360
actaagcacc aagaggagtt atggtccttt attgccgact cttttgaagga ctttatggtc    420 gagcaagaat tgctaaacac caaggacacc ttaccattag gtttcacctt ctcgtaccca    480
gcttcccaaa acaagattaa cgaaggtatt ttgcaaagat ggaccaaggg tttcgatatt    540
ccaaatgtcg aaggccacga tgtcgtccca ttgctacaaa acgaaatttc caagagagag    600
ttgcctattg aaattgtagc attgattaat gatactgttg gtactttaat tgcctcatac    660
tacactgacc cagagactaa gatgggtgtg atttttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt ttgtggtatt   1200
gccgctattt gccaaagag aggttacaag actggtcaca ttgccgctga cggttctgtc   1260
tataacaaat acccaggttt caaggaagcc gccgctaagg gtttgagaga tatctatgga   1320
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                1458
```

<210> SEQ ID NO 18
<211> LENGTH: 480
<212> TYPE: PRT
<213> ORGANISM: Saccharomyces cerevisiae

<400> SEQUENCE: 18

Met Val His Leu Gly Pro Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
    290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
        355                 360                 365

Phe Gly Val Lys Thr Thr Leu Pro Glu Arg Lys Leu Ile Arg Arg Leu

```
                370            375            380
Cys Glu Leu Ile Gly Thr Arg Ala Ala Arg Leu Ala Val Cys Gly Ile
385              390              395              400

Ala Ala Ile Cys Gln Lys Arg Gly Tyr Lys Thr Gly His Ile Ala Ala
                405              410              415

Asp Gly Ser Val Tyr Asn Lys Tyr Pro Gly Phe Lys Glu Ala Ala Ala
                420              425              430

Lys Gly Leu Arg Asp Ile Tyr Gly Trp Thr Gly Asp Ala Ser Lys Asp
                435              440              445

Pro Ile Thr Ile Val Pro Ala Glu Asp Gly Ser Gly Ala Gly Ala Ala
                450              455              460

Val Ile Ala Ala Leu Ser Glu Lys Arg Ile Ala Glu Gly Lys Ser Leu
465              470              475              480

<210> SEQ ID NO 19
<211> LENGTH: 1461
<212> TYPE: DNA
<213> ORGANISM: Saccharomyces cerevisiae

<400> SEQUENCE: 19
```

| | | |
|---|---|---|
| atggttcatt taggtccaaa aaaccacaa gccagaaagg gttccatggc cgatgtgcca | 60 |
| aaggaattga tgcaacaaat tgagaatttt gaaaaattt tcactgttcc aactgaaact | 120 |
| ttacaagccg ttaccaagca cttcatttcc gaattggaaa agggtttgtc caagaagggt | 180 |
| ggtaacattc aatgattcc aggttgggtt atggatttcc caactggtaa ggaatccggt | 240 |
| gatttcttgg ccattgattt gggtggtacc aacttgagag ttgtcttagt caagttgggc | 300 |
| ggtgaccgta cctttgacac cactcaatct aagtacagat accagatgc tatgagaact | 360 |
| actcaaaatc cagacgaatt gtgggaattt attgccgact cttttgaaagc ttttattgat | 420 |
| gagcaattcc cacaaggtat ctctgagcca attccattgg gtttcacctt ttctttccca | 480 |
| gcttctcaaa acaaaatcaa tgaaggtatc ttgcaaagat ggactaaagg ttttgatatt | 540 |
| ccaaacattg aaaaccacga tgttgttcca atgttgcaaa agcaaatcac taagaggaat | 600 |
| atcccaattg aagttgttgc tttgataaac gacactaccg gtactttggt tgcttcttac | 660 |
| tacactgacc cagaaactaa gatgggtgtt atcttcggta ctggtgtcaa tggtgcttac | 720 |
| tacgatgttt gttccgatat cgaaaagcta caaggaaaac tatctgatga cattccacca | 780 |
| tctgctccaa tggccatcaa ctgtgaatac ggttccttcg ataatgaaca tgtcgttttg | 840 |
| ccaagaacta aatacgatat caccattgat gaagaatctc caagaccagg ccaacaaacc | 900 |
| tttgaaaaaa tgtcttctgg ttactactta ggtgaaattt tgcgtttggc cttgatggac | 960 |
| atgtacaaac aaggtttcat cttcaagaac caagacttgt ctaagttcga caagcctttc | 1020 |
| gtcatggaca cttcttaccc agccagaatc gaggaagatc cattcgagaa cctagaagat | 1080 |
| accgatgact tgttccaaaa tgagttcggt atcaacacta ctgttcaaga cgtaaattg | 1140 |
| atcagacgtt tatctgaatt gattggtgct agagctgcta gattgtccgt ttgtggtatt | 1200 |
| gctgctatct gtcaaagag aggttacaag accggtcaca tcgctgcaga cggttccgtt | 1260 |
| tacaacagat acccaggttt caagaaaag gctgccaatg cttttgaagga catttacggc | 1320 |
| tggactcaaa cctcactaga cgactaccca atcaagattg ttcctgctga agatggttcc | 1380 |
| ggtgctggtg ccgctgttat tgctgctttg gcccaaaaaa gaattgctga aggtaagtcc | 1440 |
| gttggtatca tcggtgctta a | 1461 |

<210> SEQ ID NO 20
<211> LENGTH: 486
<212> TYPE: PRT
<213> ORGANISM: Saccharomyces cerevisiae

<400> SEQUENCE: 20

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365

Phe Gly Ile Asn Thr Thr Val Gln Glu Arg Lys Leu Ile Arg Arg Leu
    370                 375                 380
```

```
Ser Glu Leu Ile Gly Ala Arg Ala Ala Arg Leu Ser Val Cys Gly Ile
385                 390                 395                 400
Ala Ala Ile Cys Gln Lys Arg Gly Tyr Lys Thr Gly His Ile Ala Ala
            405                 410                 415
Asp Gly Ser Val Tyr Asn Arg Tyr Pro Gly Phe Lys Glu Lys Ala Ala
            420                 425                 430
Asn Ala Leu Lys Asp Ile Tyr Gly Trp Thr Gln Thr Ser Leu Asp Asp
        435                 440                 445
Tyr Pro Ile Lys Ile Val Pro Ala Glu Asp Gly Gly Ala Gly Ala
    450                 455                 460
Ala Val Ile Ala Ala Leu Ala Gln Lys Arg Ile Ala Glu Gly Lys Ser
465                 470                 475                 480
Val Gly Ile Ile Gly Ala
            485

<210> SEQ ID NO 21
<211> LENGTH: 1599
<212> TYPE: DNA
<213> ORGANISM: Saccharomyces cerevisiae

<400> SEQUENCE: 21
atgcttttgc aagctttcct tttccttttg ctggttttg cagccaaaat atctgcatca      60
atgacaaacg aaactagcga tagacctttg gtccacttca cacccaacaa gggctggatg    120
aatgacccaa atgggttgtg gtacgatgaa aaagatgcca atggcatct gtactttcaa    180 tacaacccaa atgacaccgt atggggtacg ccattgtttt ggggccatgc tacttccgat    240
gatttgacta attgggaaga tcaacccatt gctatcgctc caagcgtaa cgattcaggt    300 gctttctctg ctccatggt ggttgattac aacaacacga gtgggttttt caatgatact    360
attgatccaa gacaaagatg cgttgcgatt tggacttata cactcctga agtgaagag    420 caatacatta gctattctct tgatggtggt tacacttta ctgaatacca aaagaaccct    480
gttttagctg ccaactccac tcaattcaga gatccaaagg tgttctggta tgaaccttct    540
caaaaatgga ttatgacggc tgccaaatca caagactaca aaattgaaat ttactcctct    600
gatgacttga agtcctggaa gctagaatct gcatttgcca atgaaggttt cttaggctac    660
caatacgaat gtccaggttt gattgaagtc ccaactgagc aagatccttc caaatcttat    720
tgggtcatgt ttatttctat caacccaggt gcacctgctg gcggttcctt caaccaatat    780
tttgttggat ccttcaatgg tactcatttt gaagcgtttg acaatcaatc tagagtggta    840
gattttggta aggactacta tgccttgcaa actttcttca cactgaccc aacctacggt    900 tcagcattag gtattgcctg ggcttcaaac tgggagtaca gtgcctttgt cccaactaac    960
ccatggagat catccatgtc tttggtccgc aagtttcctt tgaacactga atatcaagct   1020
aatccagaga ctgaattgat caatttgaaa gccgaaccaa tattgaacat tagtaatgct   1080
ggtccctggt ctcgttttgc tactaacaca actctaacta aggccaattc ttacaatgtc   1140
gatttgagca actcgactgg taccctagag tttgagttgg tttacgctgt aacaccaca   1200 caaaccatat ccaaatccgt ctttgccgac ttatcacttt ggttcaaggg tttagaagat   1260
cctgaagaat atttgagaat gggttttgaa gtcagtgctt cttccttctt tttggaccgt   1320
ggtaactcta aggtcaagtt tgtcaaggag aacccatatt tcacaaacag aatgtctgtc   1380
aacaaccaac cattcaagtc tgagaacgac ctaagttact ataaagtgta cggcctactg   1440
gatcaaaaca tcttggaatt gtacttcaac gatggagatg tggtttctac aaataccac    1500
```

-continued

```
ttcatgacca ccggtaacgc tctaggatct gtgaacatga ccactggtgt cgataatttg    1560
ttctacattg acaagttcca agtaagggaa gtaaaatag                           1599
```

<210> SEQ ID NO 22
<211> LENGTH: 532
<212> TYPE: PRT
<213> ORGANISM: Saccharomyces cerevisiae

<400> SEQUENCE: 22

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
```

-continued

```
                355                 360                 365
Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530
```

<210> SEQ ID NO 23
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 23
aaaggaatta ccaagaccat gttttagagc tagaaatagc aag            43

<210> SEQ ID NO 24
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 24
atggtcttgg taattccttt gatcatttat ctttcactgc gga            43

<210> SEQ ID NO 25
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 25
gtatcaacaa aaaattgtta atatacctct atactttaac gtcaaggaga aaaaactata    60
gtatacttct ttttt                                                    75

<210> SEQ ID NO 26
<211> LENGTH: 75
<212> TYPE: DNA
<213> ORGANISM: Artificial Sequence
<220> FEATURE:

<223> OTHER INFORMATION: Synthetic oligonucleotide

<400> SEQUENCE: 26
aagttatgag tagaaaaaaa tgagaagttg ttctgaacaa agtaaaaaaa agaagtatac    60
tatagttttt tctcc    75

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
ctgaaacgca gatgtgcctc g    21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
ggtagtcata tcatgtcaag    20

<210> SEQ ID NO 29
<211> LENGTH: 528
<212> TYPE: PRT
<213> ORGANISM: Saccharomyces cerevisiae

<400> SEQUENCE: 29

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
            245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
            275                 280                 285

Ala Ala Thr Tyr Gly Val Val Leu Leu Ser Gly Lys Glu Gly Ser Ser
290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
            325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
            355                 360                 365

Ser Arg Glu Glu Phe Thr Arg Asp Tyr Leu Thr Thr Ser Pro Val Arg
370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Ala Ser Phe
            405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
            435                 440                 445

Asp Lys Ile Cys Ser Ile Ala Leu Ser Asn Gly Ser Tyr Gly Ser Arg
            450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
            485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
515                 520                 525

<210> SEQ ID NO 30
<211> LENGTH: 774
<212> TYPE: DNA
<213> ORGANISM: Artificial Sequence
<220> FEATURE:
<223> OTHER INFORMATION: Yeast codon optimized sequence of GDH

<400> SEQUENCE: 30
atgtcctatc aacagaagtt caggcttgat ggtgaaaggg ctgttgttac tggtggtgga      60
agagcaattg ggttgtgctg caccgaagct ttagctgaag cgggcgccgc tgttgtagtt     120
atagaaaggt ccgaagcgga cgccgaacaa gctcttgccc tgagaaatag gggctatgac     180
gttgaggttc gtgtcgggga cgttactgat gcggctagga tggatgcaat tgctaccgaa     240
ttggcggatg gaggaagacc tgctacaatt ctggtgaaca acgcaggtat tggccaaagt     300

```
ggtataccag cacaagactt aacggacgca gattggctta gaatgatgga tgtaaatcta    360
aacggcgtct tttggtgttc cagagctttt ggacgttcca tgatttccat gaagagaggc    420
gccatcgtta atctaggttc aatgtctggt acaatttgca ataggcccca acctcaaacc    480
gcgtataatg tatctaaggc tgcagtccat catcttacca gaagtttggc tgccgaatgg    540
gctcatcacg gcattcgtgt gaatgctgtt gccccaactt atattgagac tcctatggta    600
gtcgccgtag aagccaacag agaaaggatt cccctatggt tggcagacac tcctatggct    660
agaatgggaa ctccagaaga ggtggccagt gctgttctat ttcttgctag tggagcggct    720
tccttgatga cggggggcaat tgtcaacgtc gatgccgggt tcacgtgttg gtaa          774
```

<210> SEQ ID NO 31
<211> LENGTH: 771
<212> TYPE: DNA
<213> ORGANISM: Rhizobium leguminosarum

<400> SEQUENCE: 31

```
atgagctacc agcagaaatt tcgcctcgac ggcgaacgtg cggtggtcac aggcggaggg     60
cgggcgatcg gtctctgctg caccgaggcg ctggcggagg cgggcgccgc cgtcgtcgtc    120
atcgaacgca gcgaggccga cgctgagcaa gcgcttgctc tccggaatag aggctacgac    180
gtcgaagtcc gggtcggtga tgtcaccgac gcggcccgaa tggacgcgat cgcaaccgag    240
cttgccgatg gcgggcggcc ggcgaccatc ctggtcaaca atgccggaat tggccagagc    300
ggcatcccgg cgcaggatct cactgacgcc gattggctgc gcatgatgga cgtcaatctc    360
aacggcgtct tctggtgctc gcgcgccttt ggtcgttcca tgatttcgat gaaacgcggc    420
gccatcgtca acctcggctc gatgtcgggg acgatctgca accggcccca acctcagacg    480
gcctataacg tctccaaggc ggcggtccat cacctcacgc gctcgttggc cgccgagtgg    540
gcccatcacg gcatcagggt aaacgccgtc gcgcccacct acatcgagac gccgatggtg    600
gtggccgtcg aagccaatcg ggagcgtatc ccgctctggc tcgccgacac gccgatggcg    660
cggatgggaa cgccggaaga ggttgcaagc gccgtcctct cctcgcatc gggcgccgcc    720 agcctcatga ccggggcgat cgtcaacgtc gatgctgggt tcacctgctg g             771
```

<210> SEQ ID NO 32
<211> LENGTH: 500
<212> TYPE: PRT
<213> ORGANISM: Escherichia coli

<400> SEQUENCE: 32

```
Met Thr Ile Phe Asp Asn Tyr Glu Val Trp Phe Val Ile Gly Ser Gln
1               5                  10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
        35                  40                  45

Val Leu Lys Pro Leu Gly Thr Thr Pro Asp Glu Ile Thr Ala Ile Cys
    50                  55                  60

Arg Asp Ala Asn Tyr Asp Asp Arg Cys Ala Gly Leu Val Val Trp Leu
65                  70                  75                  80

His Thr Phe Ser Pro Ala Lys Met Trp Ile Asn Gly Leu Thr Met Leu
                85                  90                  95

Asn Lys Pro Leu Leu Gln Phe His Thr Gln Phe Asn Ala Ala Leu Pro
            100                 105                 110
```

```
Trp Asp Ser Ile Asp Met Asp Phe Met Asn Leu Asn Gln Thr Ala His
        115                 120                 125
Gly Gly Arg Glu Phe Gly Phe Ile Gly Ala Arg Met Arg Gln Gln His
    130                 135                 140
Ala Val Val Thr Gly His Trp Gln Asp Lys Gln Ala His Glu Arg Ile
145                 150                 155                 160
Gly Ser Trp Met Arg Gln Ala Val Ser Lys Gln Asp Thr Arg His Leu
                165                 170                 175
Lys Val Cys Arg Phe Gly Asp Asn Met Arg Glu Val Ala Val Thr Asp
            180                 185                 190
Gly Asp Lys Val Ala Ala Gln Ile Lys Phe Gly Phe Ser Val Asn Thr
        195                 200                 205
Trp Ala Val Gly Asp Leu Val Gln Val Val Asn Ser Ile Ser Asp Gly
    210                 215                 220
Asp Val Asn Ala Leu Val Asp Glu Tyr Glu Ser Cys Tyr Thr Met Thr
225                 230                 235                 240
Pro Ala Thr Gln Ile His Gly Lys Lys Arg Gln Asn Val Leu Glu Ala
                245                 250                 255
Ala Arg Ile Glu Leu Gly Met Lys Arg Phe Leu Glu Gln Gly Gly Phe
            260                 265                 270
His Ala Phe Thr Thr Thr Phe Glu Asp Leu His Gly Leu Lys Gln Leu
        275                 280                 285
Pro Gly Leu Ala Val Gln Arg Leu Met Gln Gln Gly Tyr Gly Phe Ala
    290                 295                 300
Gly Glu Gly Asp Trp Lys Thr Ala Ala Leu Leu Arg Ile Met Lys Val
305                 310                 315                 320
Met Ser Thr Gly Leu Gln Gly Gly Thr Ser Phe Met Glu Asp Tyr Thr
                325                 330                 335
Tyr His Phe Glu Lys Gly Asn Asp Leu Val Leu Gly Ser His Met Leu
            340                 345                 350
Glu Val Cys Pro Ser Ile Ala Ala Glu Glu Lys Pro Ile Leu Asp Val
        355                 360                 365
Gln His Leu Gly Ile Gly Gly Lys Asp Pro Ala Arg Leu Ile Phe
    370                 375                 380
Asn Thr Gln Thr Gly Pro Ala Ile Val Ala Ser Leu Ile Asp Leu Gly
385                 390                 395                 400
Asp Arg Tyr Arg Leu Leu Val Asn Cys Ile Asp Thr Val Lys Thr Pro
                405                 410                 415
His Ser Leu Pro Lys Leu Pro Val Ala Asn Ala Leu Trp Lys Ala Gln
            420                 425                 430
Pro Asp Leu Pro Thr Ala Ser Glu Ala Trp Ile Leu Ala Gly Gly Ala
        435                 440                 445
His His Thr Val Phe Ser His Ala Leu Asn Leu Asn Asp Met Arg Gln
    450                 455                 460
Phe Ala Glu Met His Asp Ile Glu Ile Thr Val Ile Asp Asn Asp Thr
465                 470                 475                 480
Arg Leu Pro Ala Phe Lys Asp Ala Leu Arg Trp Asn Glu Val Tyr Tyr
                485                 490                 495
Gly Phe Arg Arg
            500
```